US010173998B2

(12) United States Patent
Hoekstra et al.

(10) Patent No.: US 10,173,998 B2
(45) Date of Patent: Jan. 8, 2019

(54) ANTIFUNGAL COMPOUND PROCESS

(71) Applicants: Mycovia Pharmaceuticals, Inc., Durham, NC (US); The United States of America, as represented by the Secretary, Department of Health and Human Services, Washington, DC (US)

(72) Inventors: William J. Hoekstra, Durham, NC (US); Christopher M. Yates, Raleigh, NC (US); Mark Behnke, Poolesville, MD (US); Asaf Alimardanov, North Bethesda, MD (US); Scott A. David, Huntsburg, OH (US); Douglas Franklin Fry, Euclid, OH (US)

(73) Assignees: Mycovia Pharmaceuticals, Inc., Durham, NC (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/126,402

(22) PCT Filed: Mar. 19, 2015

(86) PCT No.: PCT/US2015/021491
§ 371 (c)(1),
(2) Date: Feb. 22, 2017

(87) PCT Pub. No.: WO2015/143172
PCT Pub. Date: Sep. 24, 2015

(65) Prior Publication Data
US 2017/0088539 A1 Mar. 30, 2017

Related U.S. Application Data

(60) Provisional application No. 61/955,615, filed on Mar. 19, 2014.

(51) Int. Cl.
C07D 401/06 (2006.01)
C07D 213/26 (2006.01)
C07D 405/06 (2006.01)
C07D 213/38 (2006.01)

(52) U.S. Cl.
CPC ......... C07D 401/06 (2013.01); C07D 213/26 (2013.01); C07D 213/38 (2013.01); C07D 405/06 (2013.01)

(58) Field of Classification Search
CPC .................................................. C07D 401/06
USPC ..................................................... 546/268.4
See application file for complete search history.

(56) References Cited

U.S. PATENT DOCUMENTS

| 4,426,531 A | 1/1984 | Bison et al. |
|---|---|---|
| 8,236,962 B2 | 8/2012 | Hoekstra et al. |
| 8,748,461 B2 | 6/2014 | Hoekstra et al. |
| 8,754,227 B2 | 6/2014 | Hoekstra et al. |
| 8,796,001 B2 | 8/2014 | Hoekstra et al. |
| 8,809,378 B2 | 8/2014 | Hoekstra et al. |
| 8,883,797 B2 | 11/2014 | Hoekstra et al. |
| 8,901,121 B2 | 12/2014 | Hoekstra et al. |
| 8,940,735 B2 | 1/2015 | Hoekstra et al. |
| 9,220,265 B2 | 12/2015 | Hoekstra et al. |
| 9,221,791 B2 | 12/2015 | Hoekstra et al. |
| 9,309,273 B2 | 4/2016 | Hoekstra et al. |
| 9,414,596 B2 | 8/2016 | Hoekstra et al. |
| 9,447,073 B2 | 9/2016 | Hoekstra et al. |
| 9,556,143 B2 | 1/2017 | Hoekstra et al. |
| 8,796,001 C1 | 3/2017 | Hoekstra et al. |
| 9,663,488 B2 | 5/2017 | Hoekstra et al. |
| 9,688,671 B2 | 6/2017 | Hoekstra et al. |
| 9,802,914 B2 | 10/2017 | Hoekstra et al. |
| 9,840,492 B2 | 12/2017 | Hoekstra et al. |
| 2009/0318436 A1 | 12/2009 | Albrecht et al. |
| 2011/0306644 A1 | 12/2011 | Hoekstra et al. |
| 2012/0329788 A1 | 12/2012 | Hoekstra et al. |
| 2012/0329802 A1 | 12/2012 | Hoekstra et al. |
| 2013/0005719 A1 | 1/2013 | Hoekstra et al. |
| 2013/0005729 A1 | 1/2013 | Hoekstra et al. |
| 2013/0005752 A1 | 1/2013 | Hoekstra et al. |
| 2013/0005776 A1 | 1/2013 | Hoekstra et al. |
| 2013/0012503 A1 | 1/2013 | Hoekstra et al. |
| 2014/0288107 A1 | 9/2014 | Hoekstra et al. |
| 2014/0350003 A1 | 11/2014 | Hoekstra et al. |
| 2015/0004666 A1 | 1/2015 | Hoekstra et al. |
| 2015/0024938 A1 | 1/2015 | Hoekstra et al. |
| 2015/0099750 A1 | 4/2015 | Hoekstra et al. |
| 2016/0214959 A1 | 7/2016 | Hoekstra et al. |
| 2017/0081285 A1 | 3/2017 | Hoekstra et al. |

(Continued)

FOREIGN PATENT DOCUMENTS

| JP | 2000-344744 A | 12/2000 |
|---|---|---|
| WO | WO 2014-193974 A1 | 12/2004 |
| WO | WO 2009/020323 A2 | 2/2009 |
| WO | WO 2010/146113 A1 | 12/2010 |
| WO | WO 2010/147302 A2 | 12/2010 |
| WO | WO 2011/133875 A2 | 10/2011 |
| WO | WO 2012/177603 A2 | 12/2012 |
| WO | WO 2012/177608 A1 | 12/2012 |
| WO | WO 2012/177635 A1 | 12/2012 |
| WO | WO 2012/177725 A1 | 12/2012 |
| WO | WO 2012/177728 A1 | 12/2012 |
| WO | WO 2013/109998 A1 | 7/2013 |

(Continued)

OTHER PUBLICATIONS

Partial Supplementary European Search Report and Search Opinion dated Jul. 13, 2017 for EP Application No. 15765715.6.

(Continued)

Primary Examiner — Patricia L Morris
(74) Attorney, Agent, or Firm — Brinks Gilson & Lione

(57) ABSTRACT

The present invention relates to a process for preparing compound 1 that is useful as an antifungal agent. In particular, the invention seeks to provide new methodology for preparing compound 1 and substituted derivatives thereof.

16 Claims, No Drawings

(56) References Cited

U.S. PATENT DOCUMENTS

| | | |
|---|---|---|
| 2017/0081309 A1 | 3/2017 | Hoekstra et al. |
| 2017/0081310 A1 | 3/2017 | Hoekstra et al. |
| 2017/0081316 A1 | 3/2017 | Hoekstra et al. |
| 2017/0088540 A1 | 3/2017 | Hoekstra et al. |
| 2017/0096410 A1 | 4/2017 | Hoekstra et al. |
| 2017/0121307 A1 | 5/2017 | Hoekstra et al. |
| 2017/0144990 A1 | 5/2017 | Hokestra et al. |
| 2017/0144991 A1 | 5/2017 | Hoekstra et al. |
| 2017/0158667 A1 | 6/2017 | Hoekstra et al. |

FOREIGN PATENT DOCUMENTS

| | | |
|---|---|---|
| WO | WO 2013/110002 A1 | 7/2013 |
| WO | WO 2014/043376 A1 | 3/2014 |
| WO | WO 2014/165861 A1 | 10/2014 |
| WO | WO 2015/143154 A1 | 9/2015 |
| WO | WO 2015/143162 A1 | 9/2015 |
| WO | WO 2015/143184 A1 | 9/2015 |
| WO | WO 2015/143192 A1 | 9/2015 |
| WO | WO 2016/187201 A2 | 11/2016 |
| WO | WO 2017/049080 A1 | 3/2017 |
| WO | WO 2017/049096 A1 | 3/2017 |
| WO | WO 2017/049196 A1 | 3/2017 |
| WO | WO 2017/087592 A1 | 5/2017 |
| WO | WO 2017/087597 A1 | 5/2017 |
| WO | WO 2017/087619 A1 | 5/2017 |
| WO | WO 2017/087643 A1 | 5/2017 |
| WO | WO 2017/117393 A1 | 7/2017 |

OTHER PUBLICATIONS

Extended European Search Report and Search Opinion dated Aug. 1, 2017 for EP Application No. 15764570.6.
Partial Supplementary European Search Report and Search Opinion dated Jul. 19, 2017 for EP Application No. 15764259.6.
Extended European Search Report and Search Opinion dated Jul. 3, 2017 for EP Application No. 15764654.8.
Extended European Search Report and Search Opinion dated Aug. 1, 2017 for EP Application No. 15764368.5.
Extended European Search Report and Search Opinion dated Jul. 21, 2017 for EP Application No. 15764743.9.
Extended European Search Report and Search Opinion dated Jul. 21, 2017 for EP Application No. 15764771.0.
Extended European Search Report and Search Opinion dated Jul. 13, 2017 for EP Application No. 15765307.2.
International Search Report and Written Opinion dated Feb. 3, 2017 for Application No. PCT/US2016/032877.
Biju, New Methodology for the Synthesis of $\alpha,\alpha$-difluoroketones. Syn. Comm. 2008; 38(12):1940-5. http://dx.doi.org/10.1080/00397910801997637.
Eto et al., New antifungal 1,2,4-triazoles with difluoro(heteroaryl)methyl moiety. Chem Pharm Bull (Tokyo). Jul. 2000;48(7):982-90.
Kolb et al., Catalytic Asymmetric Dihydroxylation. Chemical Reviews 1994;94(8):2483-2547. doi: 10.1021/cr00032a009.
Shimizu et al., Efficient method for preparation of N-methoxy-N-methyl amides by reaction of lactones or esters with Me2AlCl MeONHMe•HCl. Tetrahedron Letters. Apr. 1997;38(15):2685-8. https://doi.org/10.1016/S0040-4039(97)00429-2.
Uemura et al., Enantioselective Cyanosilylation of Ketones with Amino Acid/BINAP/Ruthenium(II)-Lithium Phenoxide Catalyst System. Advanced Synthesis & Catalysis. Jul. 2012;354(10):2023-30. doi: 10.1002/adsc.201200027.
International Search Report and Written Opinion dated Jun. 25, 2015 for Application No. PCT/US2015/021436.
International Search Report and Written Opinion dated Jun. 29, 2015 for Application No. PCT/US2015/021445.
International Search Report and Written Opinion dated Jun. 26, 2015 for Application No. PCT/US2015/021519.
International Search Report and Written Opinion dated Jun. 29, 2015 for Application No. PCT/US2015/021527.
International Search Report and Written Opinion dated Jul. 14, 2015 for Application No. PCT/US2015/021464
International Search Report and Written Opinion dated Jul. 14, 2015 for Application No. PCT/US2015/021476.
International Search Report and Written Opinion dated Jul. 10, 2015 for Application No. PCT/US2015/021484.
International Search Report and Written Opinion dated Jun. 24, 2015 for Application No. PCT/US2015/021491.
International Search Report and Written Opinion dated Jun. 26, 2015 for Application No. PCT/US2015/021504.
International Search Report and Written Opinion dated Jun. 24, 2015 for Application No. PCT/US2015/021511.
Extended European Search Report and Search Opinion dated Nov. 13, 2017 for EP Application No. 15765715.6.
Partial Supplementary European Search Report and Search Opinion dated Aug. 3, 2017 for EP Application No. 15764600.1.
Extended European Search Report and Search Opinion dated Nov. 13, 2017 for EP Application No. 15764600.1.
Extended European Search Report and Search Opinion dated Aug. 23, 2017 for EP Application No. 15765402.1.
Extended European Search Report and Search Opinion dated Oct. 24, 2017 for EP Application No. 15764259.6.

ANTIFUNGAL COMPOUND PROCESS

CROSS REFERENCE TO RELATED APPLICATIONS

This application is the U.S. National Stage, pursuant to 35 U.S.C. § 371, of International Application No. PCT/US2015/021491, filed Mar. 19, 2015, which claims the benefit of U.S. Provisional Patent Application Ser. No. 61/955,615 filed Mar. 19, 2014, the entire disclosures of which are incorporated by reference herein.

STATEMENT OF GOVERNMENT SUPPORT

This invention was created in the performance of a Cooperative Research and Development Agreement with the National Institutes of Health, an Agency of the Department of Health and Human Services. The Government of the United States has certain rights in this invention.

The present invention relates to a process for preparing compound 1 that is useful as an antifungal agent. In particular, the invention seeks to provide a new methodology for preparing compound 1 and substituted derivatives thereof.

BACKGROUND

Living organisms have developed tightly regulated processes that specifically import metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the azole antifungal agents fluconazole and voriconazole contain a 1-(1,2,4-triazole) group that binds to the heme iron present in the active site of the target enzyme lanosterol demethylase and thereby inactivates the enzyme.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymes. One example of such clinical toxicity is the unintended inhibition of human drug metabolizing enzymes such as CYP2C9, CYP2C19 and CYP3A4 by the currently-available azole antifungal agents such as fluconazole and voriconazole. It is believed that this off-target inhibition is caused primarily by the indiscriminate binding of the currently utilized 1-(1,2,4-triazole) to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders and symptoms thereof. Similarly, methods of synthesizing such therapeutic agents on the laboratory and, ultimately, commercial scale is needed. Addition of metal-based nucleophiles (Zn, Zr, Ce, Ti, Mg, Mn, Li) to azole-methyl substituted ketones have been effected in the synthesis of voriconazole (M. Butters, *Org. Process Res. Dev.* 2001, 5, 28-36). The nucleophile in these examples was an ethyl-pyrimidine substrate. Similarly, optically active azole-methyl epoxide has been prepared as precursor electrophile toward the synthesis of ravuconazole (A. Tsuruoka, *Chem. Pharm. Bull.* 1998, 46, 623-630). Despite this, the development of methodology with improved efficiency and selectivity is desirable.

BRIEF SUMMARY OF THE INVENTION

The invention is directed toward methods of synthesis of 1 or 1a. The methods can comprise the compounds herein. A first aspect of the invention relates to a process for preparing a compound of formula 1, or a pharmaceutically acceptable salt, hydrate, solvate, complex or prodrug thereof.

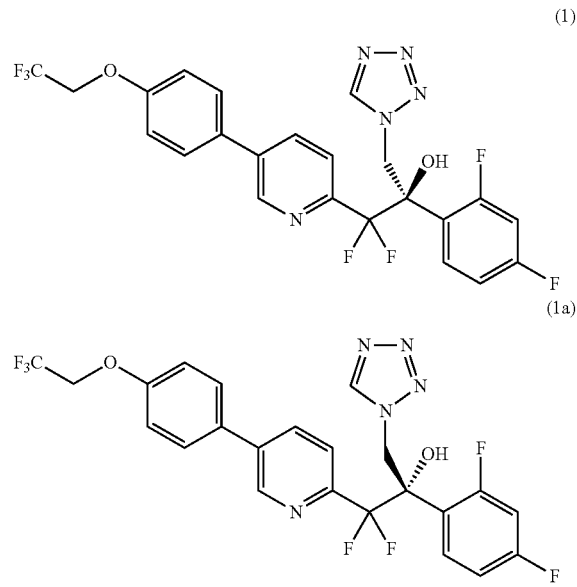

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson John Wiley & Sons Inc; 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In the following aspects, reference is made to the schemes and compounds herein, including the reagents and reaction conditions delineated herein. Other aspects include any of the compounds, reagents, transformations or methods thereof delineated in the examples herein (in whole or in part), including as embodiments with single elements (e.g., compounds or transformations) or embodiments including multiple elements (e.g., compounds or transformations).

In one aspect, the invention provides a process to prepare a compound of formula II:

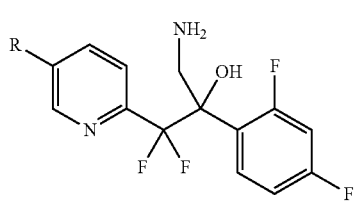

II comprising epoxide opening of a compound of formula I:

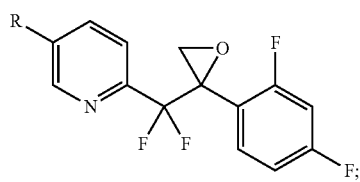

I to provide a compound of formula II;
wherein R is

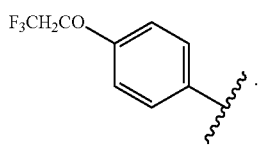

In another aspect, the invention provides a process to prepare amino-alcohol 1-6 or 1-7, or a mixture thereof:

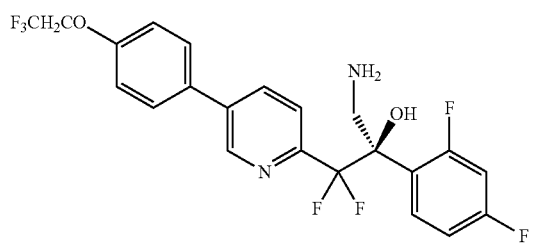

1-6

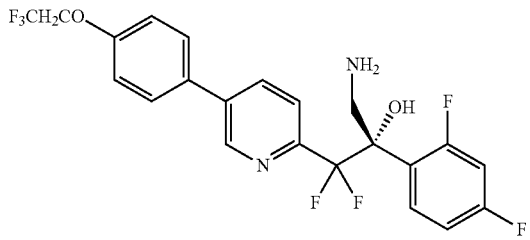

1-7 comprising arylation of substituted pyridine 4b or 4c, or a mixture thereof:

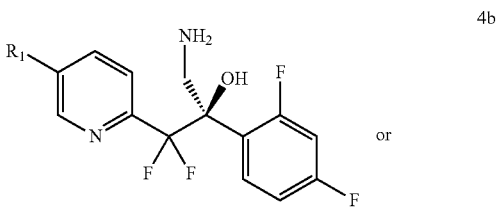

4b or

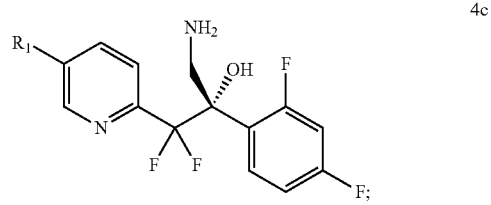

4c to provide compound 1-6 or 1-7, or a mixture thereof;
wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)— aryl, or —O(SO$_2$)-substituted aryl.

In another embodiment, the invention provides a process of enriching the enantiomeric purity of an enantiomeric compound mixture, comprising:

(i) crystallizing said enantiomeric compound mixture with a chiral acid in a suitable solvent or solvent mixture, wherein:

the suitable solvent or solvent mixture is selected from acetonitrile, isopropanol, ethanol, water, methanol, or combinations thereof; and the enantiomeric compound mixture comprises

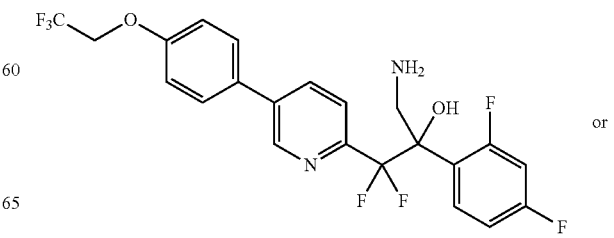

or

-continued

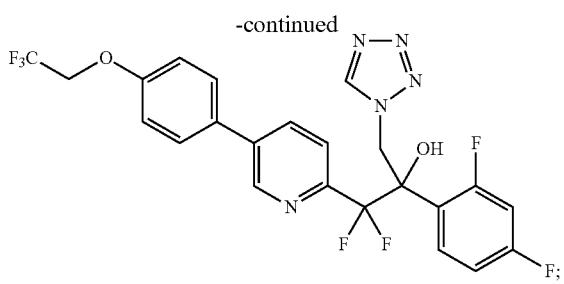

and
(ii) isolating the enantio-enriched compound mixture
(iii) reslurrying the enantio-enriched chiral salt mixture in a slurrying solvent or slurrying solvent mixture; and
(iv) free-basing the enantio-enriched chiral salt mixture to provide the enantio-enriched compound mixture.

In another embodiment, the invention provides a process of enriching the enantiomeric purity of an enantiomeric compound mixture, comprising:
(i) crystallizing said enantiomeric compound mixture with a chiral acid in a suitable solvent or solvent mixture, wherein:
the suitable solvent or solvent mixture is selected from acetonitrile, isopropanol, ethanol, water, methanol, or combinations thereof; and
the enantiomeric compound mixture comprises

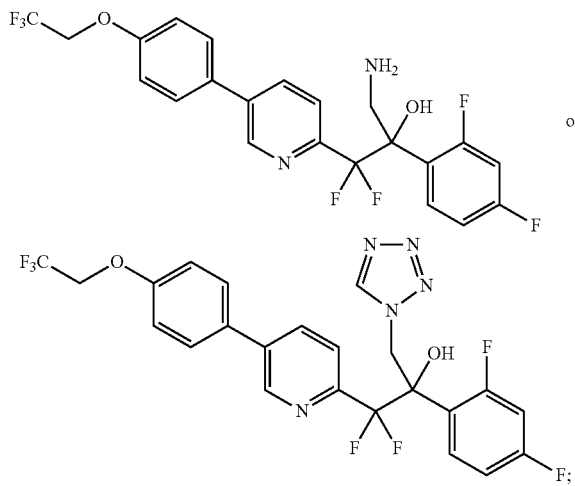

and
(ii) isolating the enantio-enriched compound mixture; and
(iii) free-basing the enantio-enriched chiral salt mixture to provide the enantio-enriched compound mixture.

In another aspect, the chiral acid from any embodiment presented herein is selected from the group consisting of tartaric acid, di-benzoyltartaric acid, malic acid, camphoric acid, camphorsulfonic acid, ascorbic acid, and di-p-toluoyl-tartaric acid;

In another aspect, the suitable solvent or solvent mixture from any embodiments presented herein is 1-propanol, 1-butanol, ethyl acetate, tetrahydrofuran, 2-methyltetrahydrofuran, toluene, methyl tert-butylether, diethyl ether, dichloromethane, 1,4-dioxane, 1,2-dimethoxyethane, isopropyl acetate, heptane, hexane, cyclohexane, or octane, or combinations thereof.

In another aspect, the slurrying solvent or slurrying solvent mixture from any embodiments presented herein is 1-propanol, 1-butanol, ethyl acetate, tetrahydrofuran, 2-methyltetrahydrofuran, toluene, methyl tert-butylether, diethyl ether, dichloromethane, 1,4-dioxane, 1,2-dimethoxyethane, isopropyl acetate, heptane, hexane, cyclohexane, or octane, or combinations thereof.

In another aspect, the suitable solvent or solvent mixture from any embodiments presented herein is a) acetonitrile or b) a mixture of acetonitrile and isopropanol. Alternatively, another aspect is where the mixture of acetonitrile and methanol comprises 80-90% acetonitrile and 10-20% isopropanol.

In another aspect, the slurrying solvent or slurrying solvent mixture from any embodiments presented herein is a) acetonitrile or b) a mixture of acetonitrile and isopropanol. Alternatively, another aspect is where the mixture of acetonitrile and isopropanol comprises 80-90% acetonitrile and 10-20% isopropanol.

In another aspect, the invention provides a process to prepare compound 1 or 1a, or a mixture thereof:

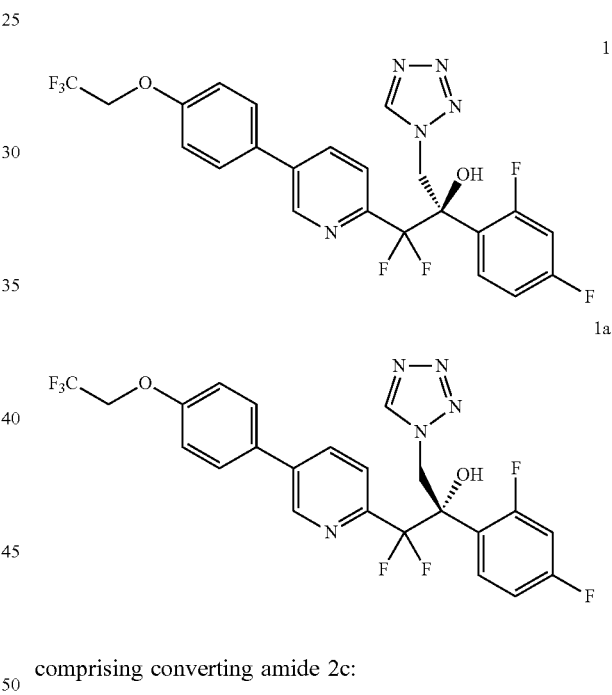

comprising converting amide 2c:

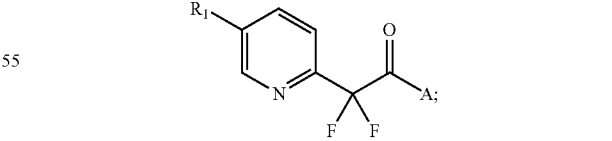

to compound 1 or 1a, or mixtures thereof;
wherein $R_1$ is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl;

A is N(OMe)Me, NR$_8$R$_9$, or

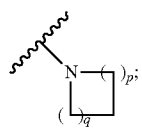

p is 1, 2, 3, or 4;
q is 1, 2, 3, or 4;
each R$_8$ and R$_9$ are each independently H, alkyl, substituted alkyl, aryl, substituted aryl, heteroaryl, or substituted heteroaryl.

In another aspect, the invention provides a process to prepare compound 1 or 1a, or a mixture thereof:

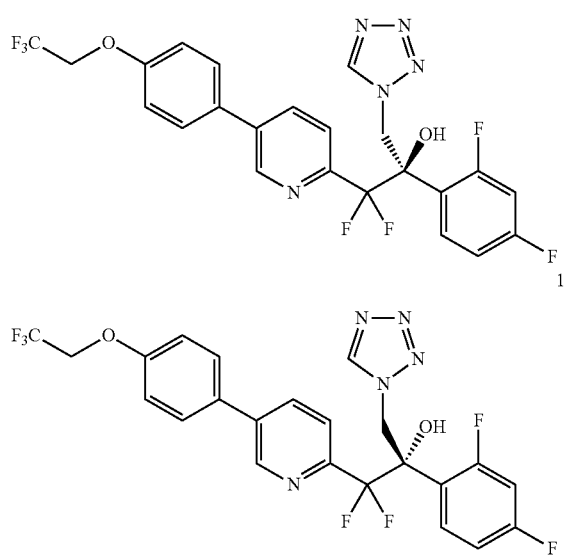

comprising converting amide 2c:

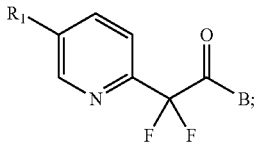

to compound 1 or 1a, or mixtures thereof;
wherein R$_1$ is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl;
B is N(OMe)Me, NR$_8$R$_9$, or

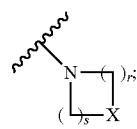

X is O, NR$_8$, or S;
r is 2, 3, or 4;
s is 2, 3, or 4;
each R$_8$ and R$_9$ are each independently H, alkyl, substituted alkyl, aryl, substituted aryl, heteroaryl, or substituted heteroaryl.

In another aspect, the invention provides a process to prepare compound 1 or 1a, or a mixture thereof:

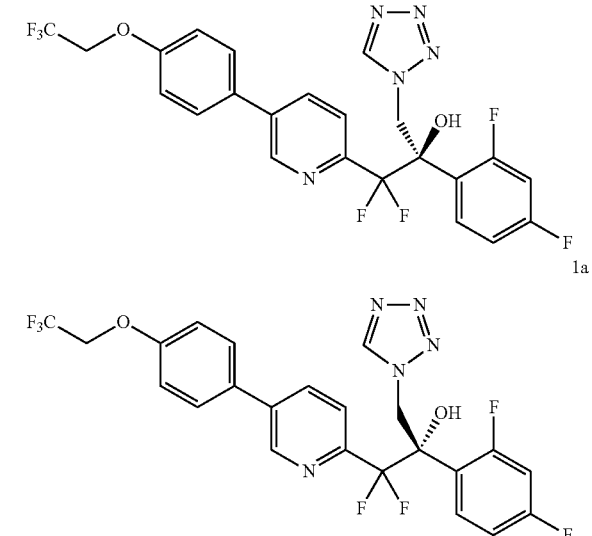

comprising converting morpholine amide 2b:

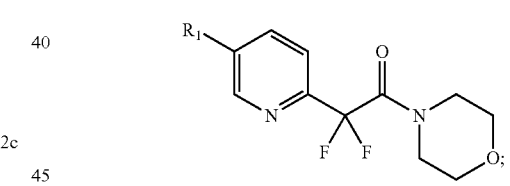

to compound 1 or 1a, or mixtures thereof;
wherein R$_1$ is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process comprising reacting morpholine amide 2b:

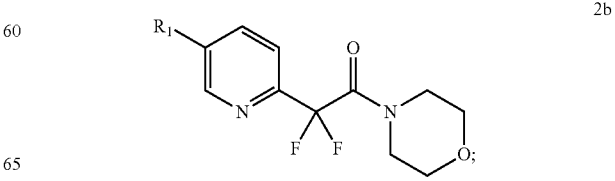

with

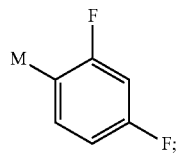

wherein M is Mg or MgX; and X is halogen;
to provide compound 1 or 1a, or a mixture thereof:

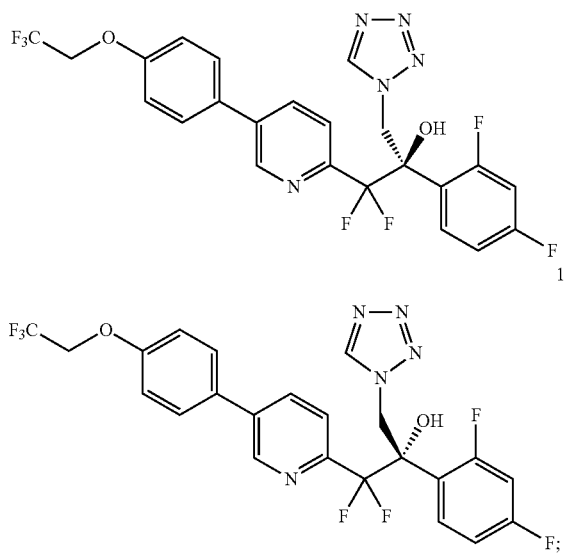

wherein R$_1$ is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process comprising reacting morpholine amide 2b:

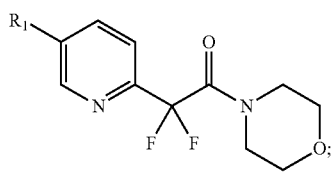

with

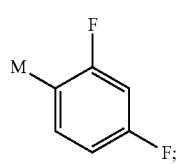

wherein M is Mg or MgX, Li, AlX$_2$; and X is halogen, alkyl, or aryl;
to provide compound 1 or 1a, or a mixture thereof:

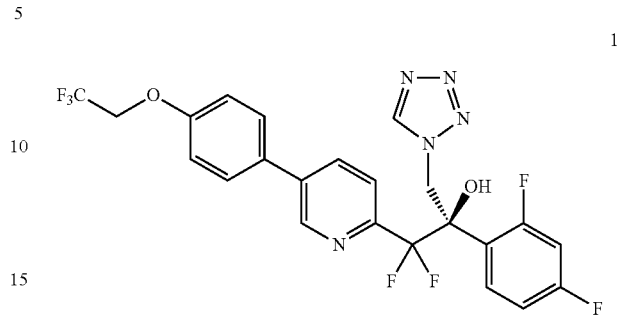

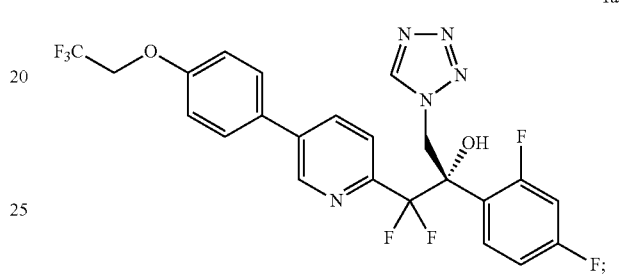

wherein R$_1$ is halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)-aryl, or —O(SO$_2$)-substituted aryl.

In another aspect, any of the embodiments presented herein may comprise amidation of ester 2:

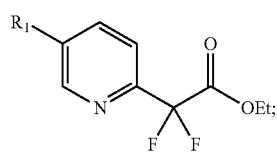

to provide morpholine amide 2b:

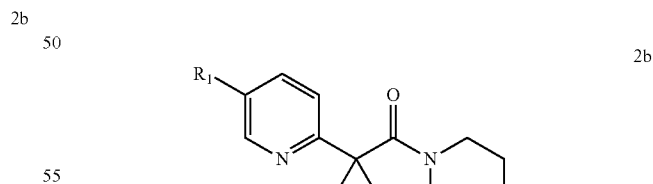

wherein each R$_1$ is independently halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)-aryl, or —O(SO$_2$)-substituted aryl.

In another aspect, any of the embodiments presented herein may comprise amidation of ester 2d:

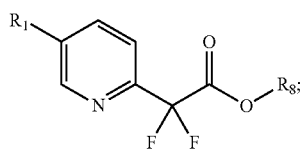

2d to provide morpholine amide 2b:

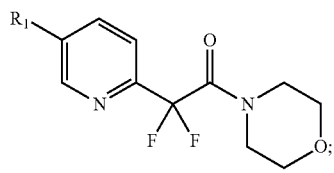

2b wherein each $R_1$ is independently halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)— aryl, or —O(SO$_2$)-substituted aryl; and $R_8$ is H, alkyl, substituted alkyl, aryl, substituted aryl, heteroaryl, or substituted heteroaryl.

In another aspect, any of the embodiments presented herein may comprise reacting ester 2:

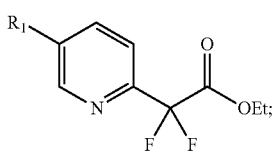

2 with morpholine to provide morpholine amide 2b:

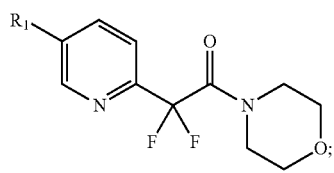

2b wherein each $R_1$ is independently halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO$_2$)-alkyl, —O(SO$_2$)-substituted alkyl, —O(SO$_2$)— aryl, or —O(SO$_2$)-substituted aryl.

In another aspect, any of the embodiments presented herein may comprise:

(i) displacing the morpholino portion of morpholine amide 2b,

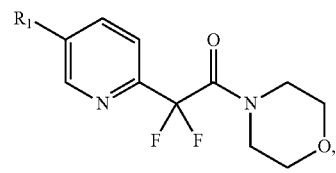

5 to provide ketone 3,

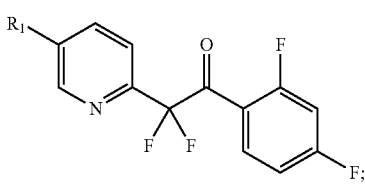

3

(ii) arylating ketone 3,

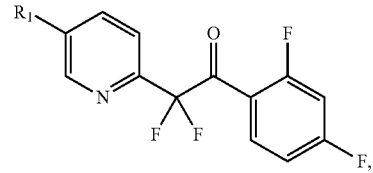

to provide aryl-pyridine 1-4,

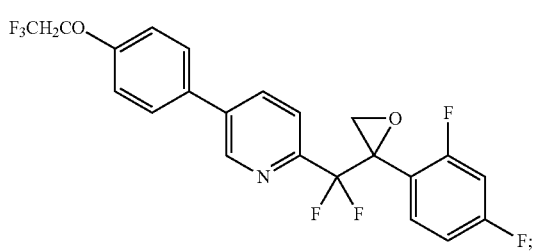

1-4

(iii) forming the epoxide of aryl-pyridine 1-4, to provide epoxide 5, (iv) ring-opening epoxide 5,

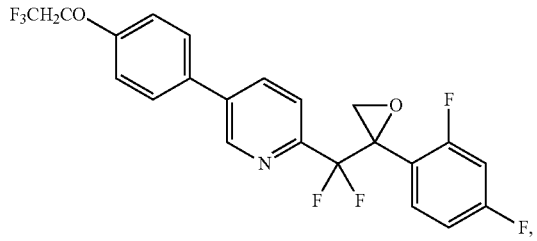

to provide amino-alcohol ±1-6,

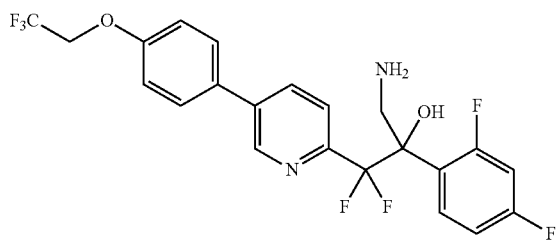

(v) enriching the enantiomeric purity of amino-alcohol ±1-6,

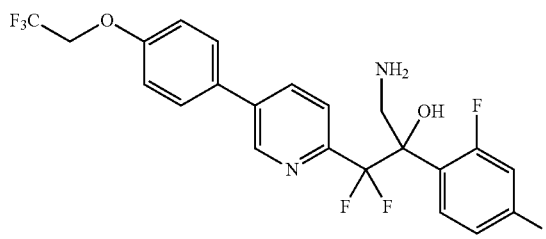

to provide enantio-enriched amino-alcohol 1-6* or 1-7*,

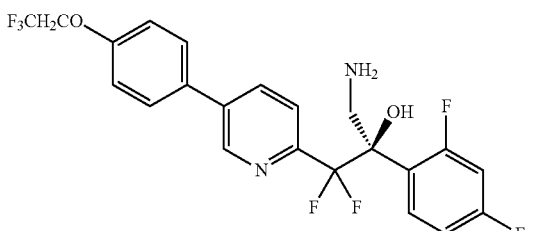

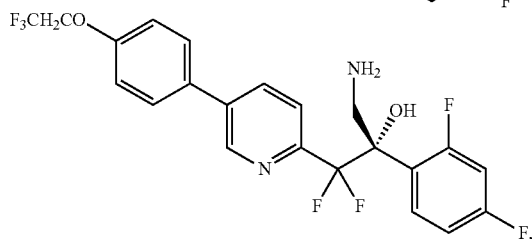

or a mixture thereof; and
(vi) forming the tetrazole of enantio-enriched amino-alcohol 1-6* or 1-7*,

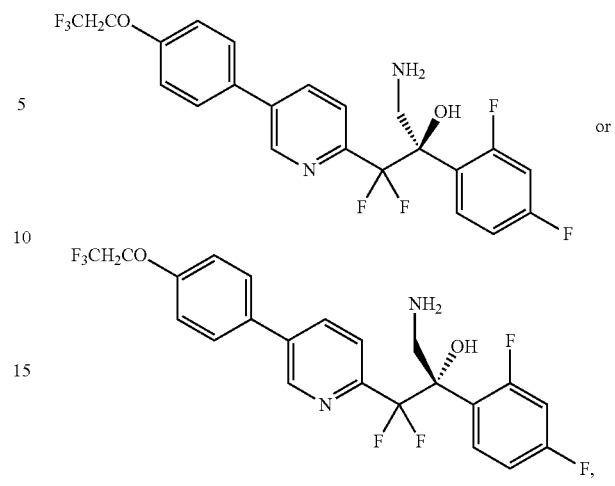

or a mixture thereof, to provide compound 1 or 1a,

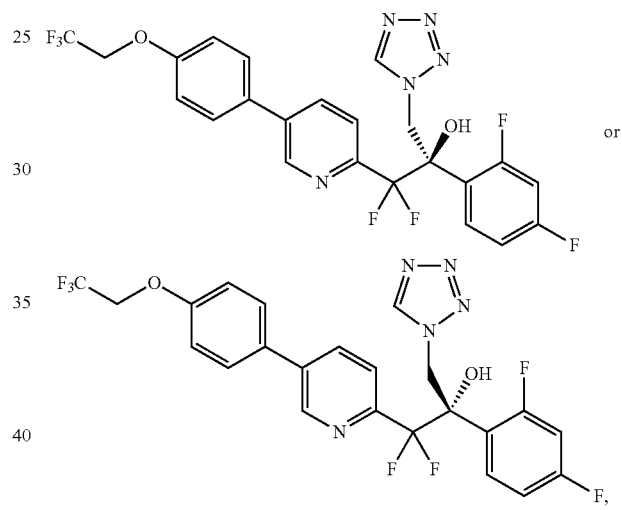

or a mixture thereof;
wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a compound of 1-6* or 1-7*,

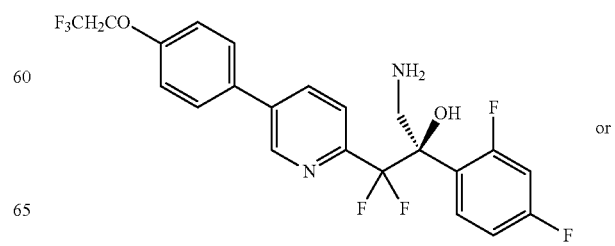

-continued

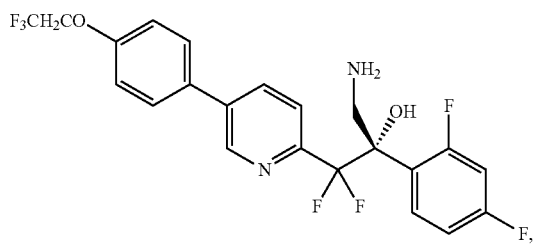

or a mixture thereof.

In another aspect, the invention provides a process to prepare enantio-enriched aryl-pyridine 1-6* or 1-7*, enantio-enriched amino-alcohol 1-6* or 1-7*,

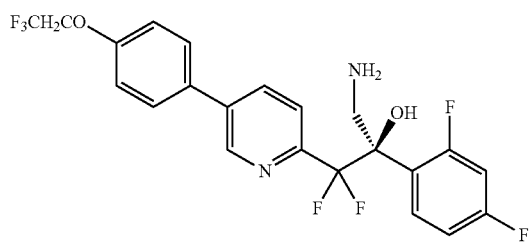

or

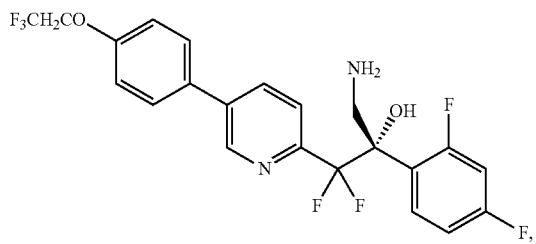

or a mixture thereof, the method comprising:

(i) displacing the morpholino portion of morpholine amide 2b,

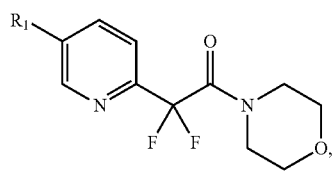

to provide ketone 3,

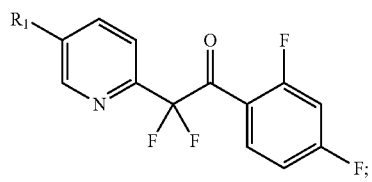

(ii) arylating ketone 3,

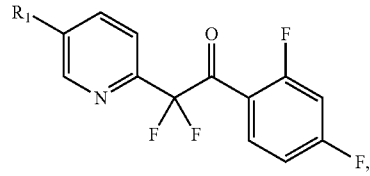

to provide aryl-pyridine 1-4,

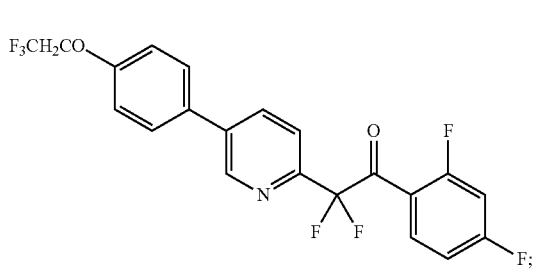

(iii) forming the epoxide of aryl-pyridine 1-4,

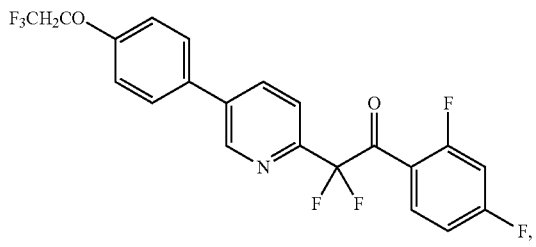

to provide epoxide 5,

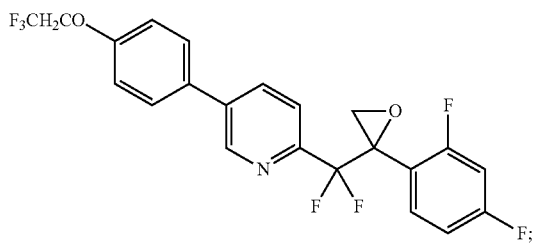

(iv) ring-opening epoxide 5,

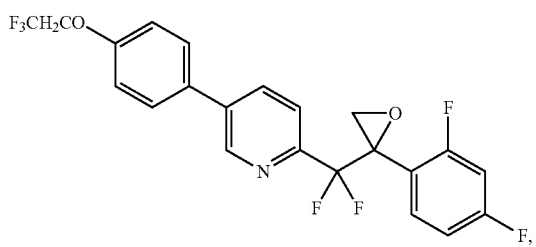

to provide amino-alcohol ±1-6,

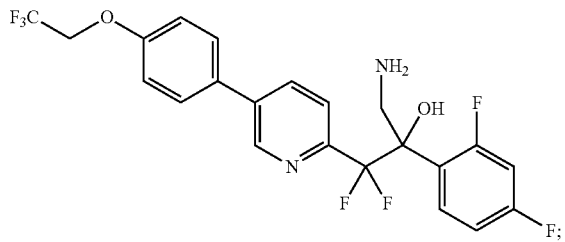 [SMILES: NCC(O)(c1ccc(F)cc1F)C(F)(F)c1ccc(-c2ccc(OCC(F)(F)F)cc2)cn1]

and (v) enriching the enantiomeric purity of amino-alcohol ±1-6,

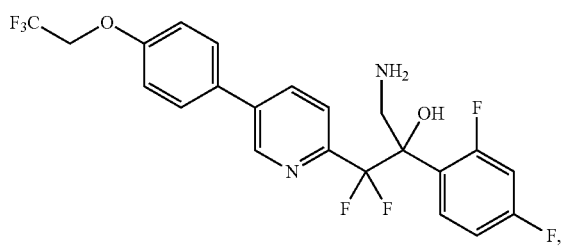 [SMILES: NCC(O)(c1ccc(F)cc1F)C(F)(F)c1ccc(-c2ccc(OCC(F)(F)F)cc2)cn1]

to provide enantio-enriched amino-alcohol 1-6* or 1-7*,

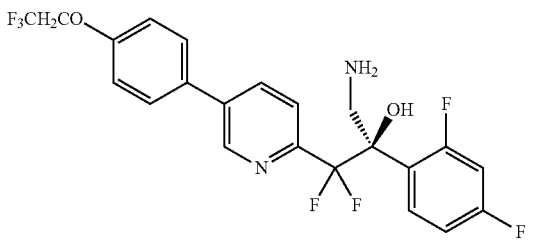

or

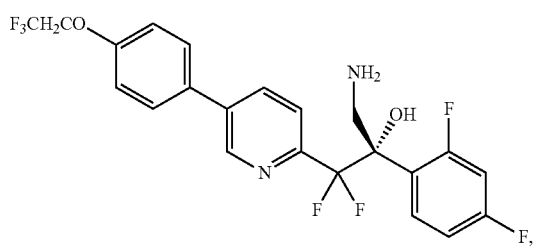

or a mixture thereof;

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare enantio-enriched aryl-pyridine 1-6* or 1-7*, enantio-enriched amino-alcohol 1-6* or 1-7*,

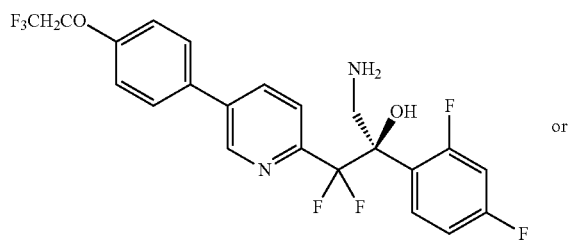

or

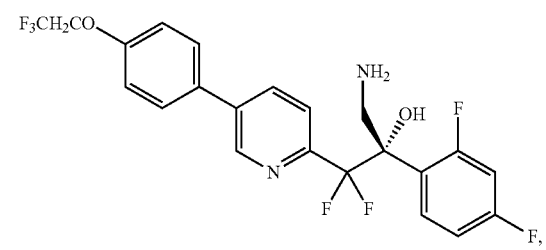

or a mixture thereof, the method comprising:

(i) ring-opening epoxide 5,

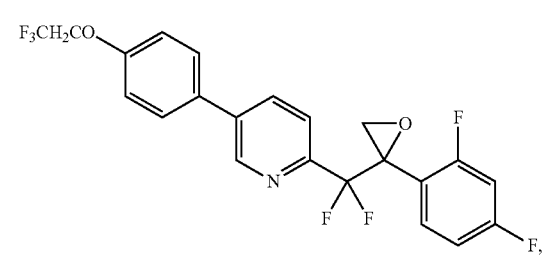

to provide amino-alcohol ±1-6,

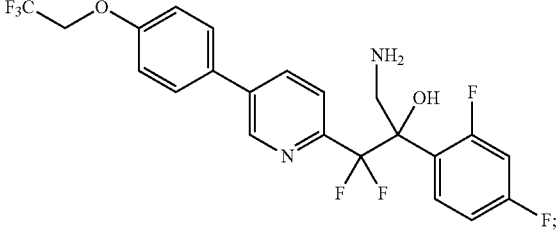

and (ii) enriching the enantiomeric purity of amino-alcohol ±1-6,

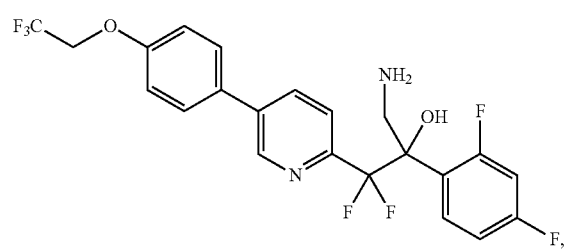

to provide enantio-enriched amino-alcohol 1-6* or 1-7*,

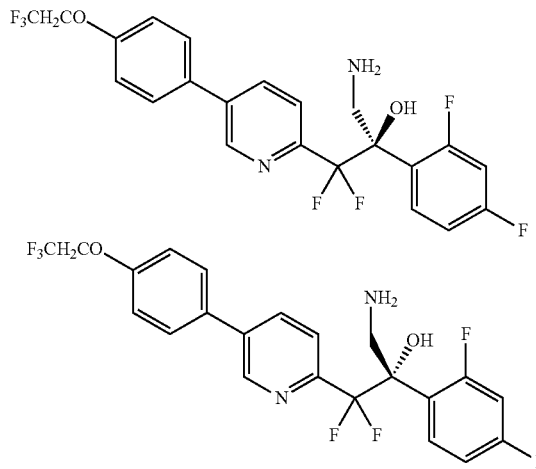

or a mixture thereof;

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare epoxide 5,

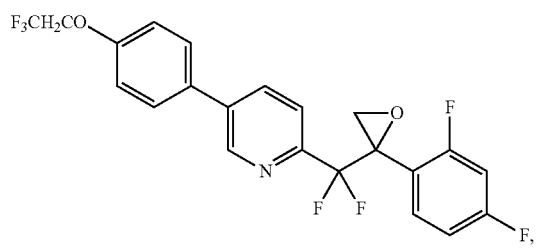

the method comprising:
(i) displacing the morpholino portion of morpholine amide 2b,

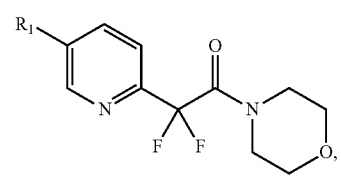

to provide ketone 3,

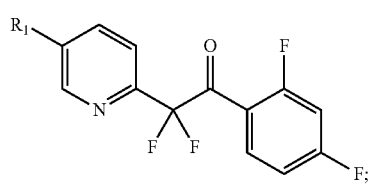

(ii) arylating ketone 3,

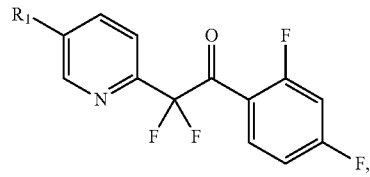

to provide aryl-pyridine 1-4,

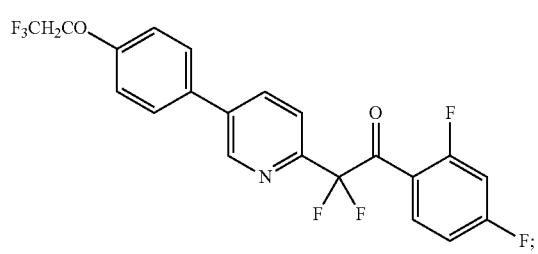

and
(iii) forming the epoxide of aryl-pyridine 1-4,

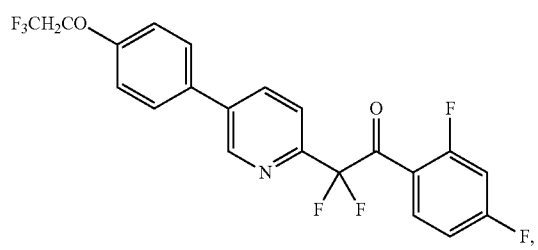

to provide epoxide 5,

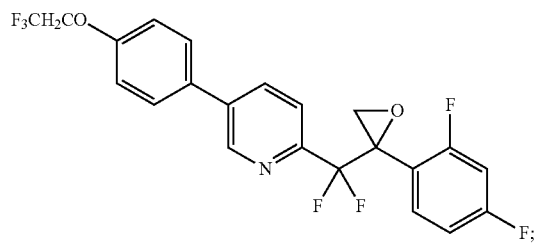

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare epoxide 5,

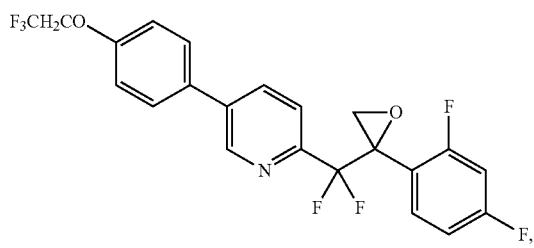

the method comprising:

(i) forming the epoxide of aryl-pyridine 1-4,

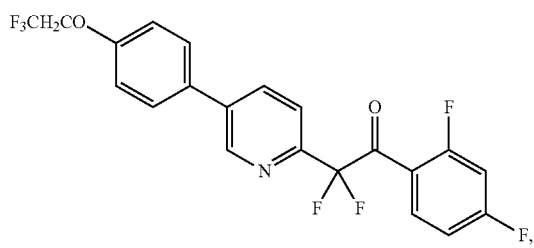

to provide epoxide 5,

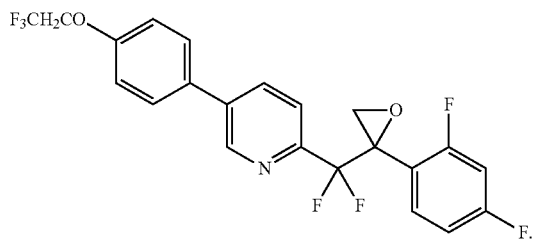

In another aspect, any of the embodiments presented herein may comprise:

(i) displacing the morpholino portion of morpholine amide 2b,

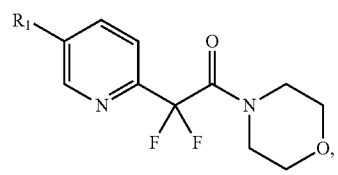

to provide ketone 3,

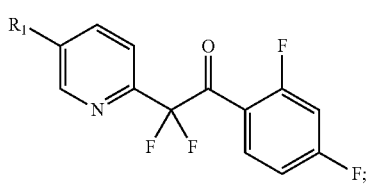

(ii) forming the epoxide of ketone 3,

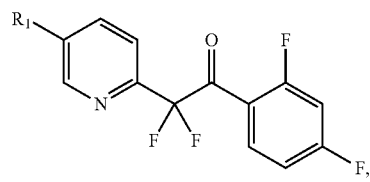

to provide epoxide 4,

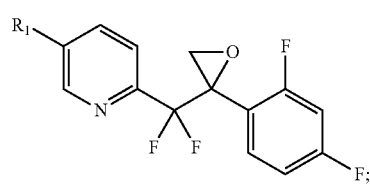

(iii) ring-opening epoxide 4,

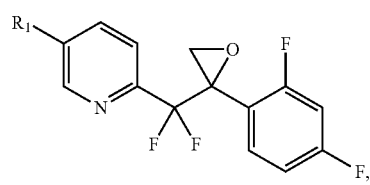

to provide amino-alcohol ±4b,

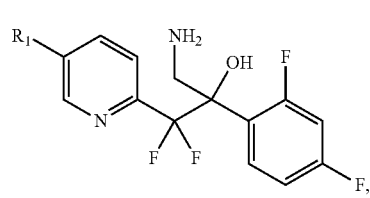

(iv) enriching the enantiomeric purity of amino-alcohol ±4b,

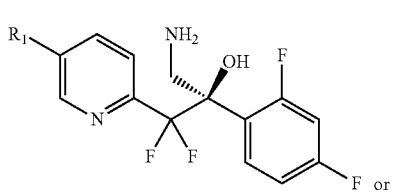

to provide enantio-enriched amino-alcohol 4b or 4c:

-continued

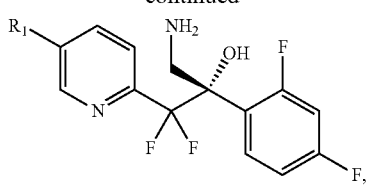

or a mixture thereof;

(v) forming the tetrazole of enantio-enriched amino-alcohol 4b or 4c:

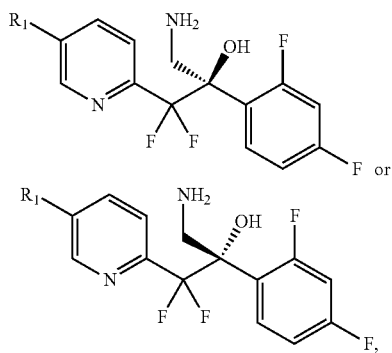

or a mixture thereof, to provide tetrazole 6 or 6a,

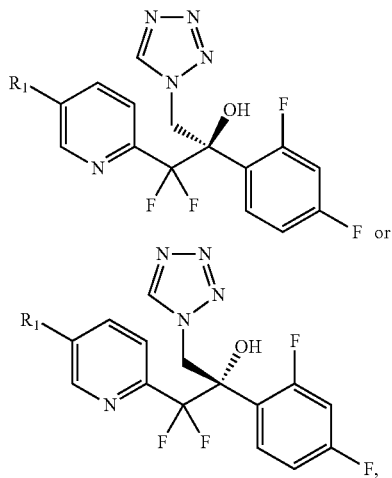

or a mixture thereof; and (vi) arylating tetrazole 6 or 6a,

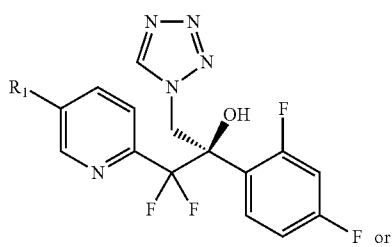

-continued

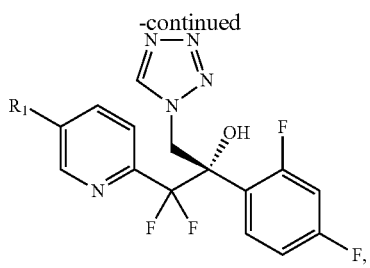

or a mixture thereof, to provide compound 1 or 1a,

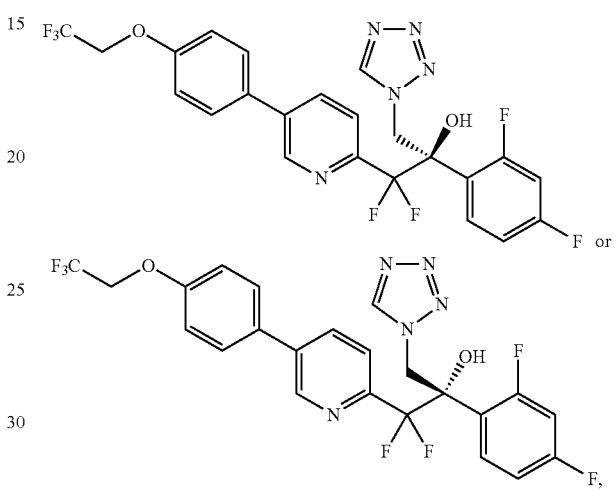

or a mixture thereof;
wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, any of the embodiments presented herein may comprise:

(i) displacing the morpholino portion of morpholine amide 2b,

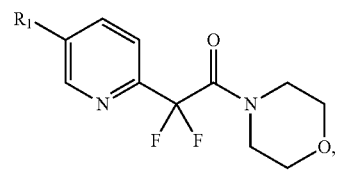

to provide ketone 3,

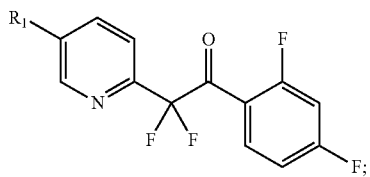

(ii) forming the epoxide of ketone 3,

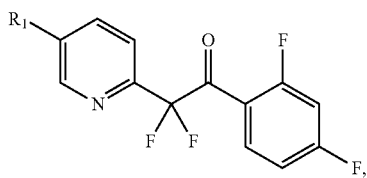

to provide epoxide 4,

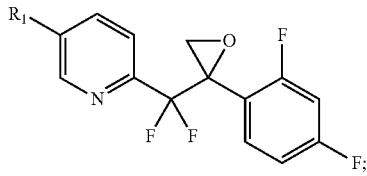

(iii) ring-opening epoxide 4,

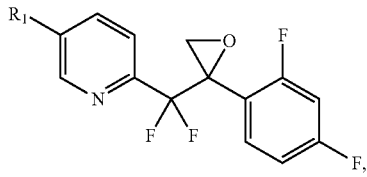

to provide amino-alcohol ±4b,

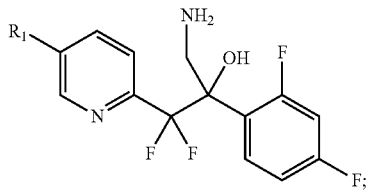

(iv) enriching the enantiomeric purity of amino-alcohol ±4b,

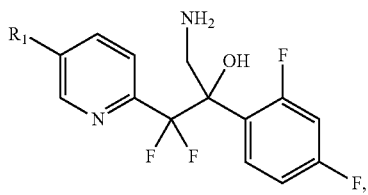

to provide enantio-enriched amino-alcohol 4b or 4c:

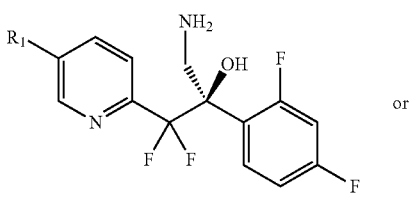

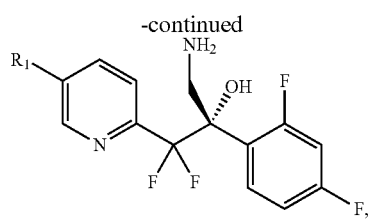

or a mixture thereof;
(v) arylating enantio-enriched amino-alcohol 4b or 4c,

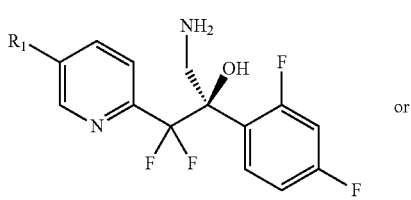

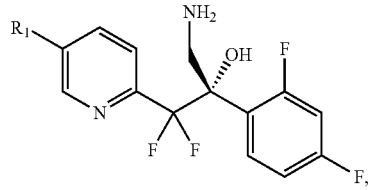

or a mixture thereof, to provide enantio-enriched aryl-pyridine 1-6* or 1-7*,

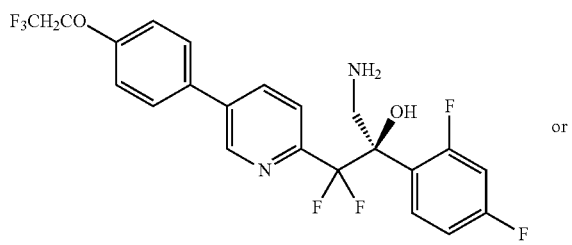

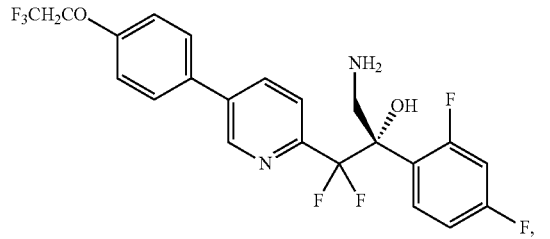

or a mixture thereof; and
(vi) forming the tetrazole of enantio-enriched aryl-pyridine 1-6* or 1-7*,

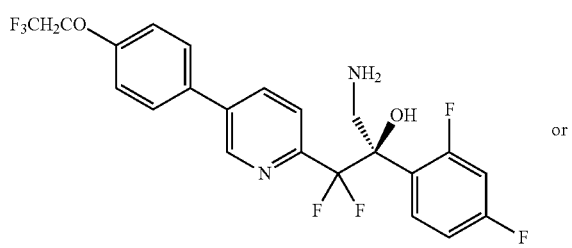

27

-continued

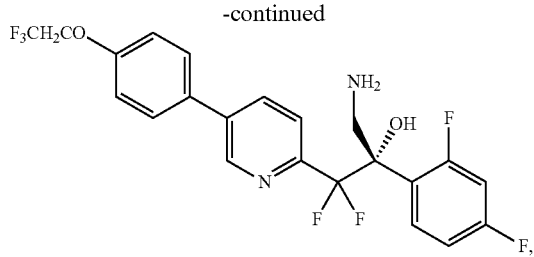

or a mixture thereof, to provide compound 1 or 1a,

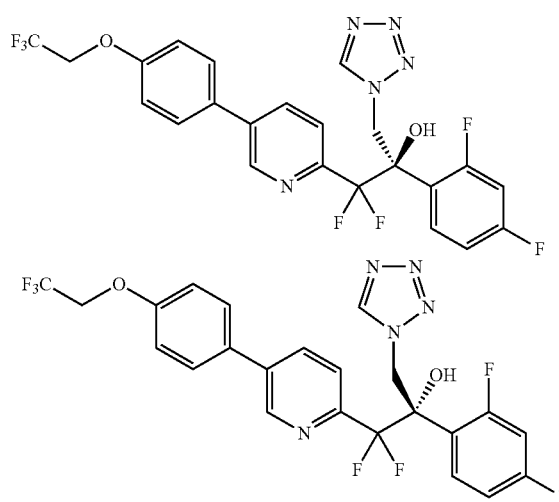

or a mixture thereof;

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare enantio-enriched aryl-pyridine 1-6* or 1-7*, enantio-enriched amino-alcohol 1-6* or 1-7*,

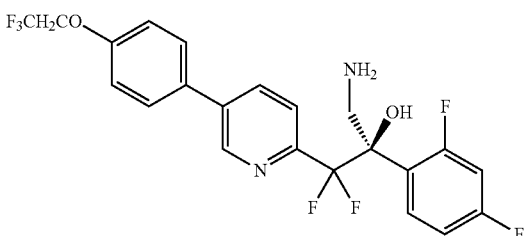

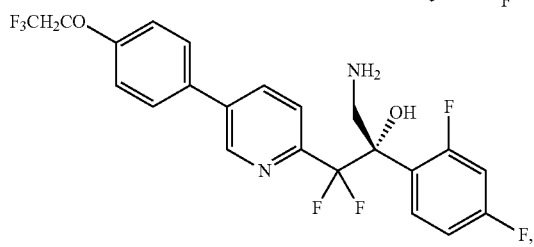

28 or a mixture thereof, the method comprising:

(i) displacing the morpholino portion of morpholine amide 2b,

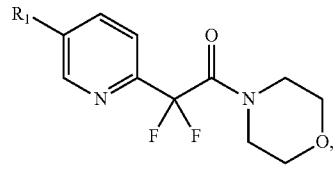

to provide ketone 3,

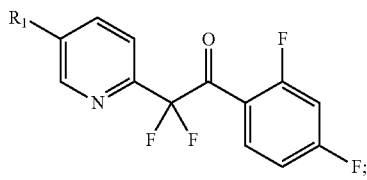

(ii) forming the epoxide of ketone 3,

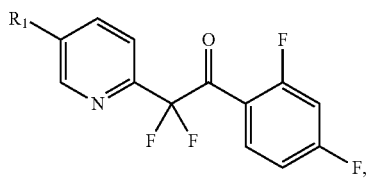

to provide epoxide 4,

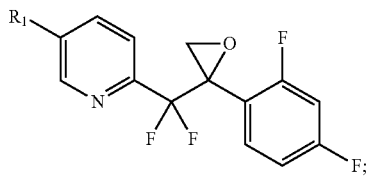

(iii) ring-opening epoxide 4,

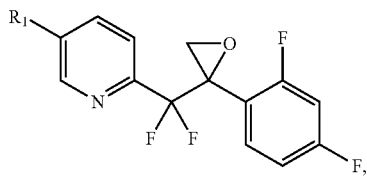

to provide amino-alcohol ±4b,

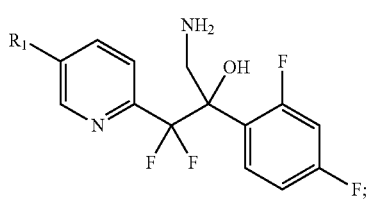

(iv) enriching the enantiomeric purity of amino-alcohol ±4b,

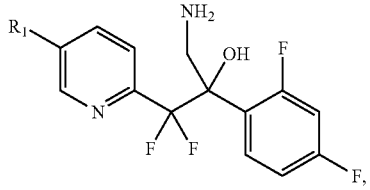

to provide enantio-enriched amino-alcohol 4b or 4c:

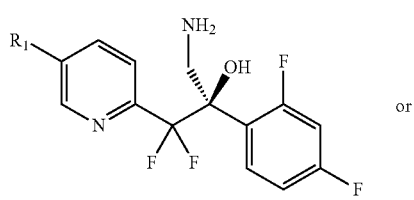

or

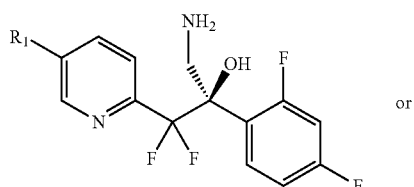

or a mixture thereof; and (v) arylating enantio-enriched amino-alcohol 4b or 4c,

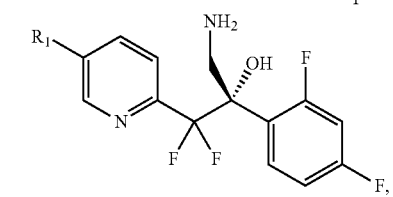

or

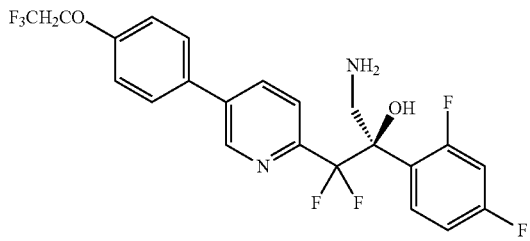

or a mixture thereof, to provide enantio-enriched aryl-pyridine 1-6* or 1-7*,

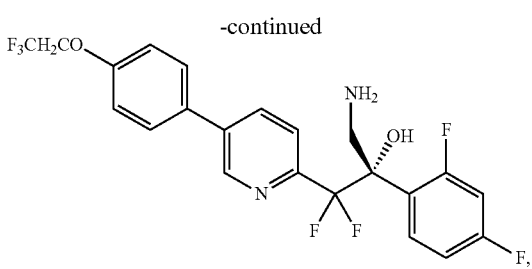

or

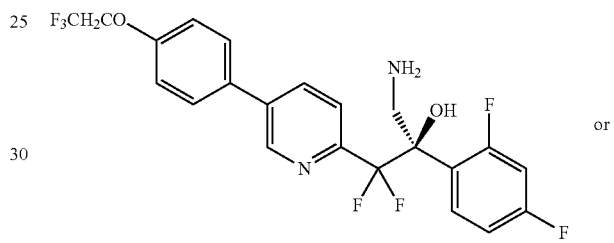

or a mixture thereof;

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare enantio-enriched aryl-pyridine 1-6* or 1-7*, enantio-enriched amino-alcohol 1-6* or 1-7*,

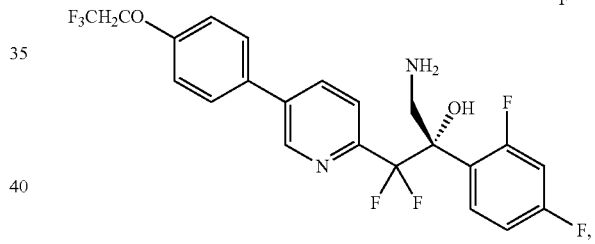

or a mixture thereof, the method comprising:

(i) ring-opening epoxide 4,

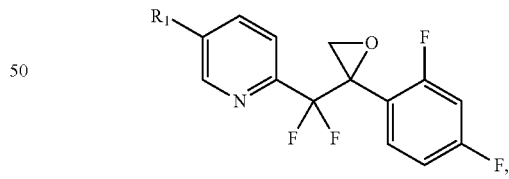

to provide amino-alcohol ±4b,

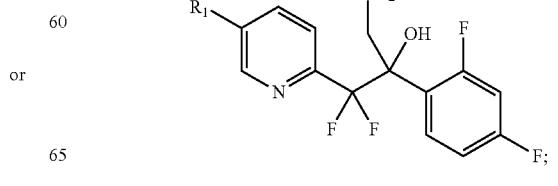

(ii) enriching the enantiomeric purity of amino-alcohol ±4b,

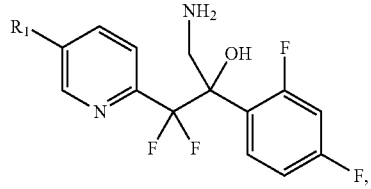

to provide enantio-enriched amino-alcohol 4b or 4c:

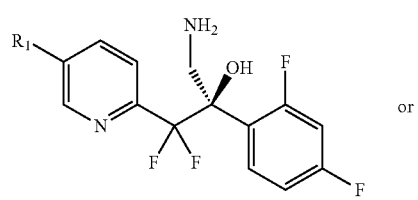

or

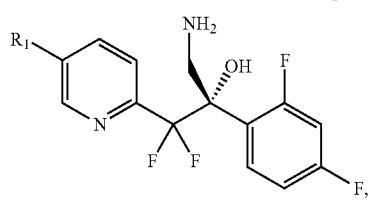

or a mixture thereof; and (iii) arylating enantio-enriched amino-alcohol 4b or 4c,

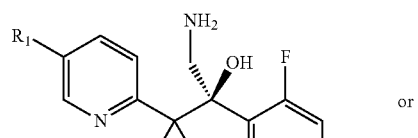

or

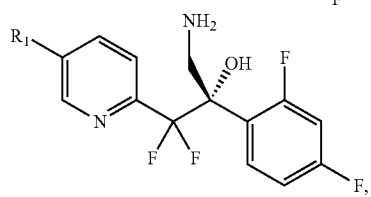

or a mixture thereof, to provide enantio-enriched aryl-pyridine 1-6* or 1-7*,

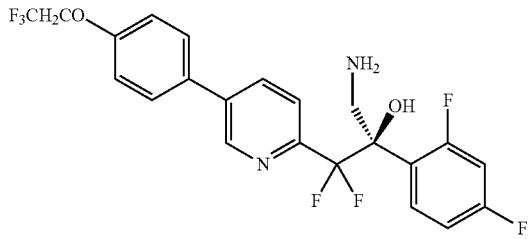

or

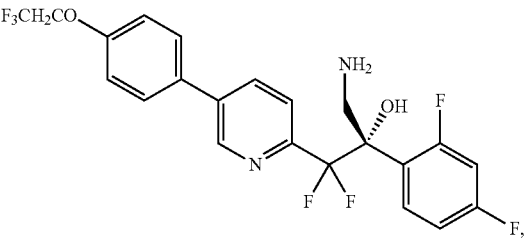

or a mixture thereof;

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare enantio-enriched amino-alcohol 4b or 4c:

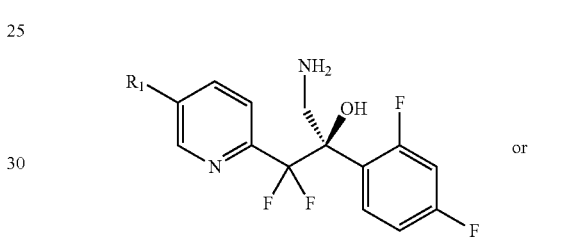

or a mixture thereof, the method comprising:

(i) displacing the morpholino portion of morpholine amide 2b,

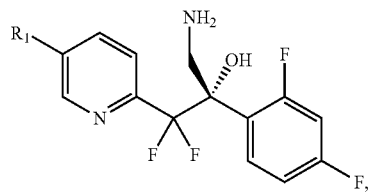

to provide ketone 3,

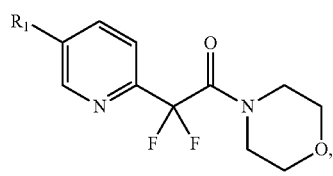

(ii) forming the epoxide of ketone 3,

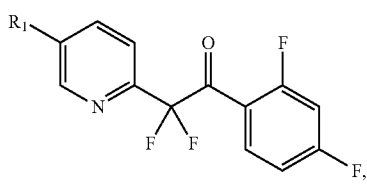

to provide epoxide 4,

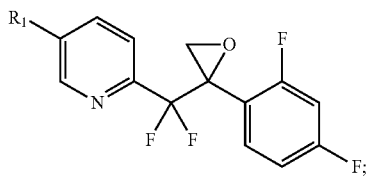

(iii) ring-opening epoxide 4,

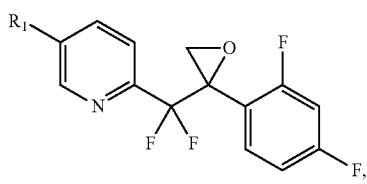

to provide amino-alcohol ±4b,

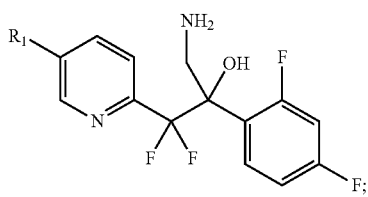

and
(iv) enriching the enantiomeric purity of amino-alcohol ±4b,

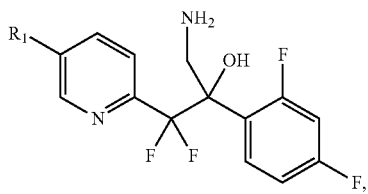

to provide enantio-enriched amino-alcohol 4b or 4c:

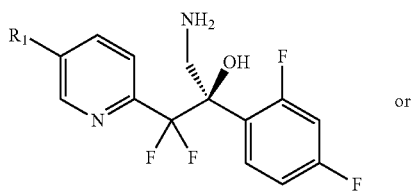

or

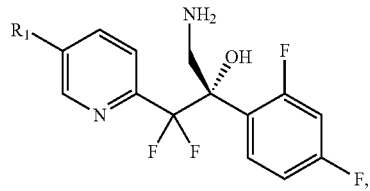

or a mixture thereof;

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare enantio-enriched amino-alcohol 4b or 4c:

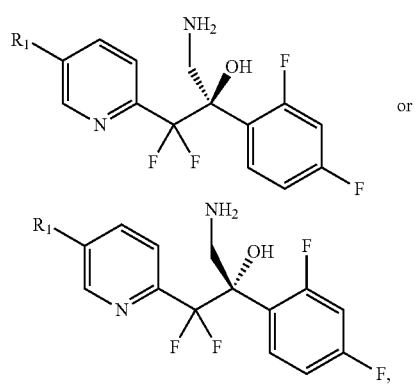

or a mixture thereof, the method comprising:
(i) ring-opening epoxide 4,

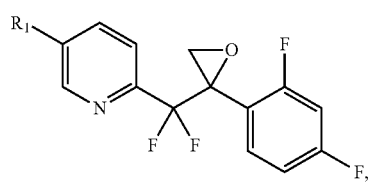

to provide amino-alcohol ±4b,

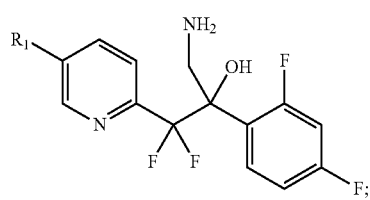

and
(ii) enriching the enantiomeric purity of amino-alcohol ±4b,

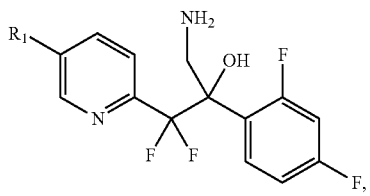

to provide enantio-enriched amino-alcohol 4b or 4c:

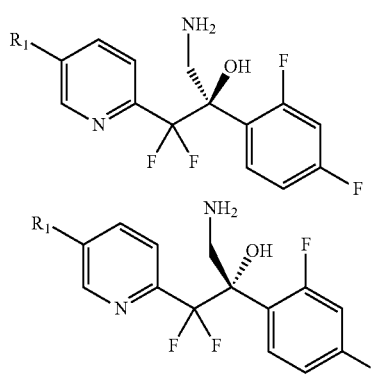

or a mixture thereof;
wherein each R$_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare enantio-enriched amino-alcohol 4b or 4c:

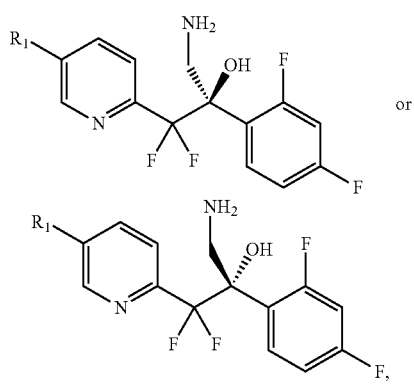

or a mixture thereof, the method comprising:
(i) enriching the enantiomeric purity of amino-alcohol ±4b,

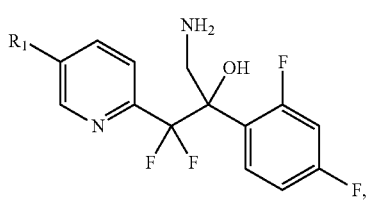

to provide enantio-enriched amino-alcohol 4b or 4c:

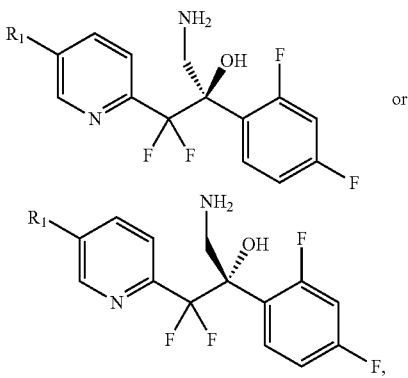

or a mixture thereof;
wherein each R$_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare compound 1 or 1a, or a mixture thereof:

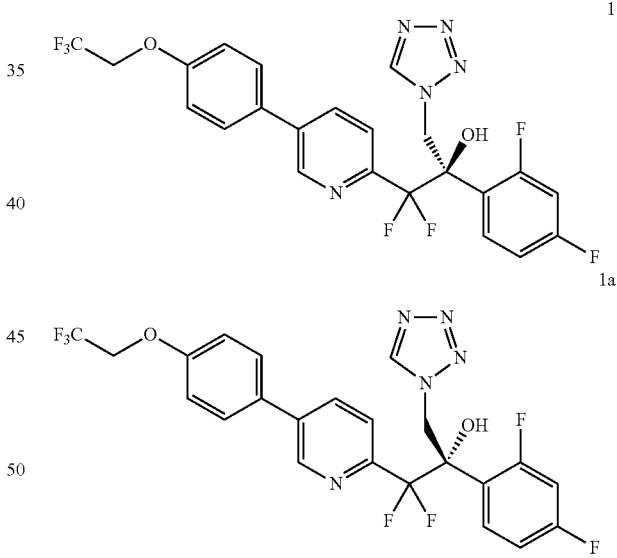

comprising epoxide-opening of a compound of formula I, VII or VIIa:

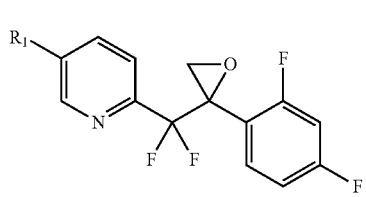

-continued

VII
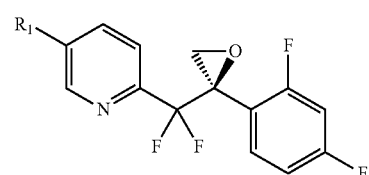

VIIa
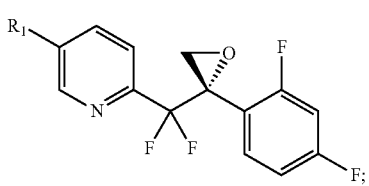

1
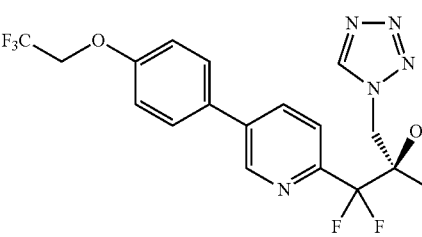

to provide a compound of formula II, VIII or VIIIa:

II
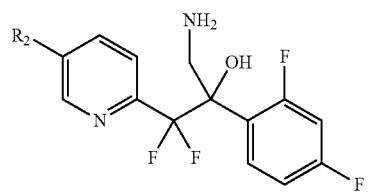

1a
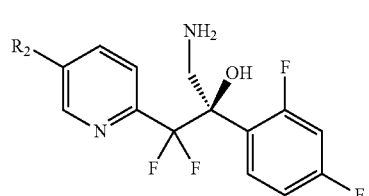

comprising forming the tetrazole of substituted-pyridine 4d or 4e, or a mixture thereof:

VIII
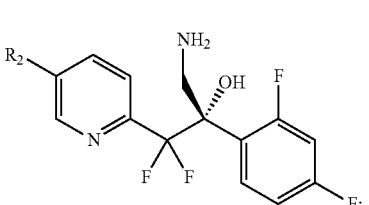

4d
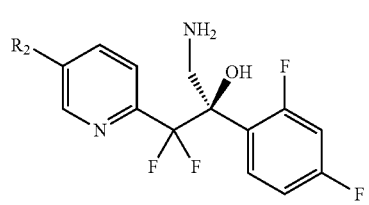

VIIIa
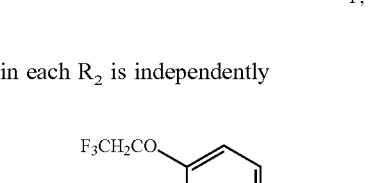

4e
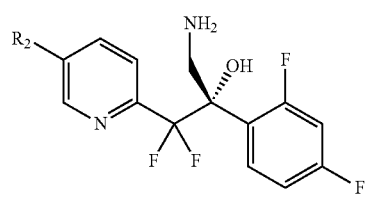

wherein each R₂ is independently

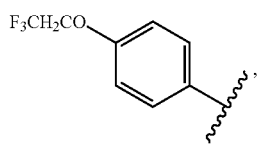

to tetrazole 6c or 6d, halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In another aspect, the invention provides a process to prepare compound 1 or 1a, or mixtures thereof:

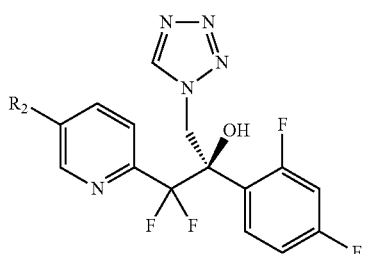

or

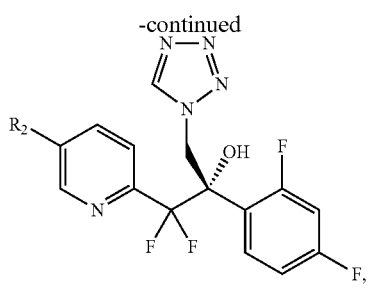

or a mixture thereof;
wherein each $R_2$ is independently

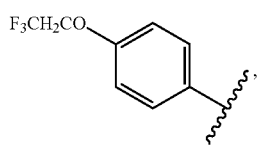

halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare compound 1 or 1a, or a mixture thereof:

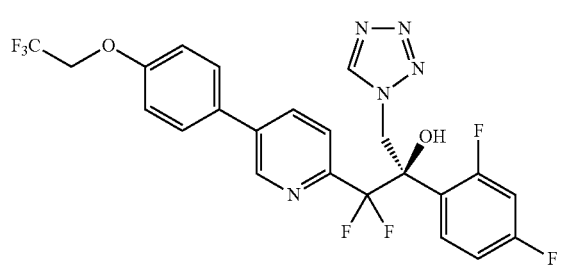

comprising the arylation of amino-alcohol 4b or 4c,

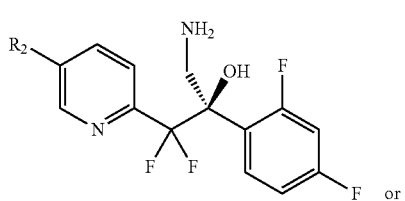

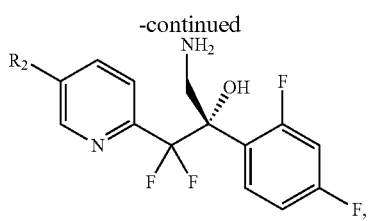

or a mixture thereof, to amino aryl-pyridine 1-6* or 1-7*,

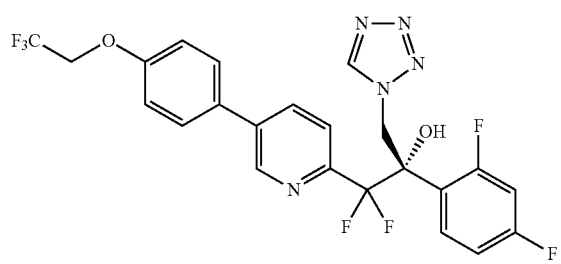

or a mixture thereof;
wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare compound 1 or 1a, or a mixture thereof:

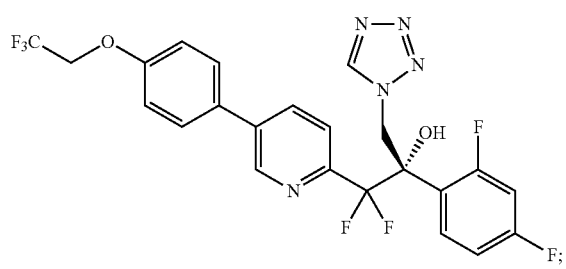

comprising converting a compound of formula 15:

![Formula 15: A pyridine ring with R₁ substituent, connected via CF₂ to a carbonyl group attached to 2,4-difluorophenyl]

to compound 1 or 1a;

wherein R₁ is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

In another aspect, the invention provides a compound of formula IX or IXa, or a mixture thereof:

![Formula IX]

![Formula IXa]

wherein each Z is independently aryl, substituted aryl, alkyl, or substituted alkyl.

In another aspect, the invention provides a compound of formula XI or XIa, or a mixture thereof:

![Formula XI]

![Formula XIa]

wherein:

each $R_{10}$ is independently H, optionally substituted alkyl, optionally substituted aryl, optionally substituted heteroaryl, optionally substituted cycloalkyl, optionally substituted heterocyclyl, optionally substituted arylalkyl, or optionally substituted heteroarylalkyl;

each $R_{11}$ is independently H, OH, optionally substituted alkyl, optionally substituted alkoxy, or OC(O)$R_{14}$;

each $R_{12}$ is independently H, optionally substituted alkyl, optionally substituted aryl, optionally substituted heteroaryl, optionally substituted cycloalkyl, optionally substituted heterocyclyl, optionally substituted arylalkyl, or optionally substituted heteroarylalkyl;

each $R_{13}$ is independently H, OH, optionally substituted alkyl, optionally substituted alkoxy, or OC(O)$R_{14}$;

each $R_{14}$ is independently H, optionally substituted alkyl, optionally substituted aryl, optionally substituted heteroaryl, optionally substituted cycloalkyl, optionally substituted heterocyclyl, optionally substituted arylalkyl, or optionally substituted heteroarylalkyl; and each t is independently 0, 1, 2, or 3.

In another aspect, $R_{10}$ is H and t is 1.
In another aspect, $R_{12}$ is H and t is 1.
In another aspect, $R_{10}$ is H, $R_{12}$ is H, and t is 1.
In another aspect, $R_{11}$ is OH or OC(O)$R_{14}$ (preferably, OC(O)-p-tolyl) and t is 1.
In another aspect, $R_{13}$ is OH or OC(O)$R_{14}$ (preferably, OC(O)-p-tolyl) and t is 1.
In another aspect, $R_{11}$ is OH or OC(O)$R_{14}$ (preferably, OC(O)-p-tolyl), $R_{13}$ is OH or OC(O)$R_{14}$ (preferably, OC(O)-p-tolyl), and t is 1.
In another aspect, $R_{10}$ is H, $R_{11}$ is OH or OC(O)$R_{14}$ (preferably, OC(O)-p-tolyl), $R_{12}$ is H, $R_{13}$ is H, OH, or OC(O)$R_{14}$ (preferably, OC(O)-p-tolyl), and t is 1.

In another aspect, $R_{10}$ is H, $R_{11}$ is OH or $OC(O)R_{14}$ (preferably, OC(O)-p-tolyl), $R_{12}$ is H, $R_{13}$ is OH or $OC(O)R_{14}$ (preferably, OC(O)-p-tolyl), and t is 1.

In another aspect, $R_{10}$ is H, $R_{11}$ is $OC(O)R_{14}$ (preferably, OC(O)-p-tolyl), $R_{12}$ is H, $R_{13}$ is $OC(O)R_{14}$ (preferably, OC(O)-p-tolyl), and t is 1.

In another aspect, $R_{10}$ is H, $R_{11}$ is $OC(O)R_{14}$, $R_{12}$ is H, $R_{13}$ is $OC(O)R_{14}$, each $R_{14}$ is independently optionally substituted arylalkyl, and t is 1. In another aspect, each $R_{14}$ is p-tolyl.

In another aspect, $R_{11}$ is OH, $R_{13}$ is H, and t is 1.

In another aspect, $R_{10}$ is H, $R_{11}$ is OH, $R_{12}$ is H, $R_{13}$ is H, and t is 1.

In another aspect, the invention provides a process to prepare a compound of formula IX or IXa, or a mixture thereof, comprising:

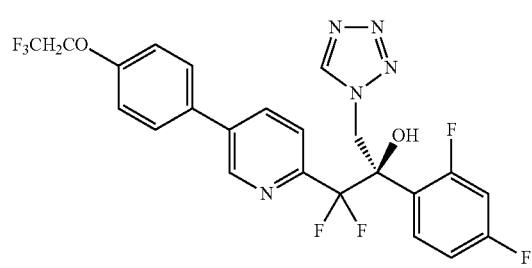

IX

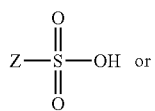

or

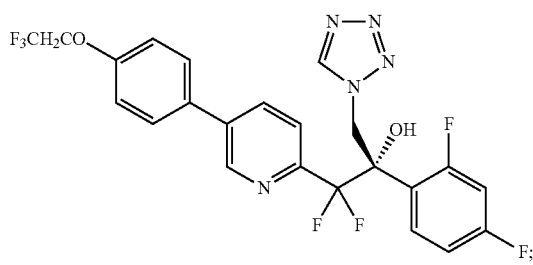

IXa

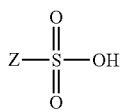

(i) combining compound 1 or 1a,

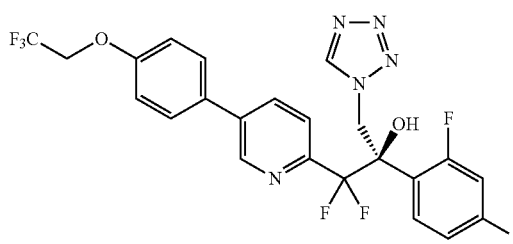

or

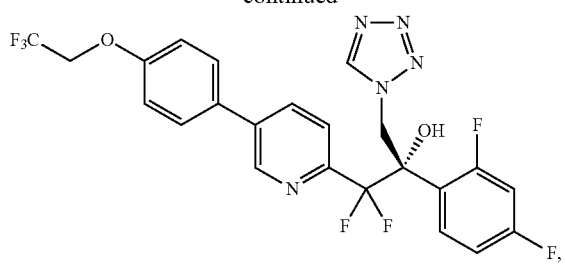

or a mixture thereof, a sulfonic acid

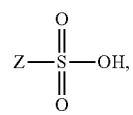

and a crystallization solvent or crystallization solvent mixture;

(ii) diluting the mixture from step (i) with a crystallization co-solvent or crystallization co-solvent mixture; and (iii) isolating a compound of formula IX or IXa, or a mixture thereof;

wherein each Z is independently aryl, substituted aryl, alkyl, or substituted alkyl.

In another aspect, the invention provides a compound of X or Xa, or a mixture thereof:

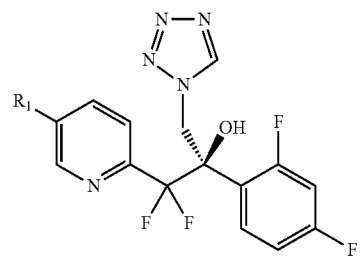

X

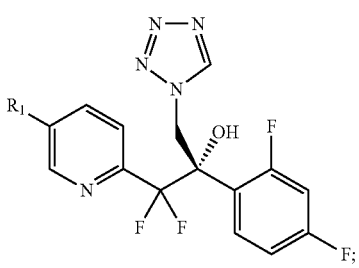

Xa wherein each $R_1$ is independently halo, —O(C═O)-alkyl, —O(C═O)-substituted alkyl, —O(C═O)-aryl, —O(C═O)-substituted aryl, —O(C═O)—O-alkyl, —O(C═O)—O-substituted alkyl, —O(C═O)—O-aryl, —O(C═O)—O-substituted aryl, —O(SO₂)-alkyl, —O(SO₂)-substituted alkyl, —O(SO₂)-aryl, or —O(SO₂)-substituted aryl.

In another aspect, the invention provides a process to prepare compound 1 or 1a, or a mixture thereof, comprising:

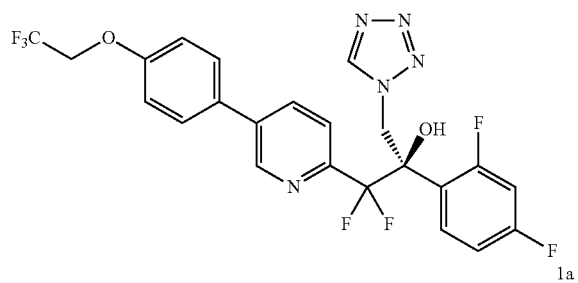
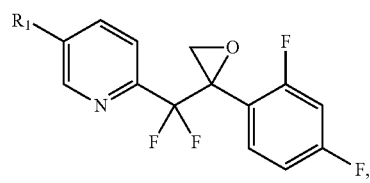
(iii) ring-opening epoxide 4,
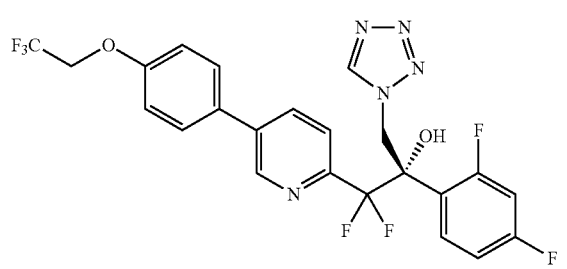
to provide amino-alcohol ±4b,
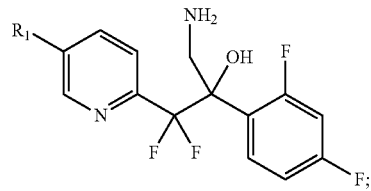
(i) displacing the ester portion of ester 2,
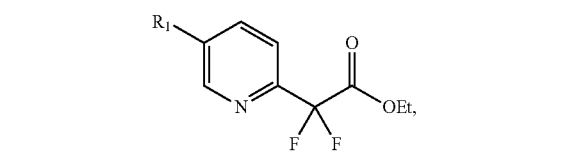
(iv) enriching the enantiomeric purity of amino-alcohol ±4b,
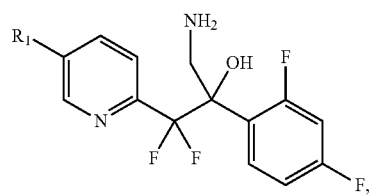
to provide ketone 3,
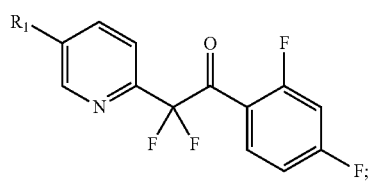
to provide enantio-enriched amino-alcohol 4b or 4c:
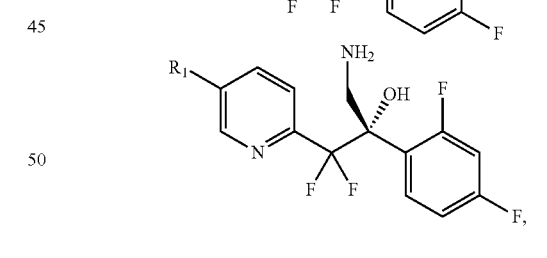
(ii) forming the epoxide of ketone 3,
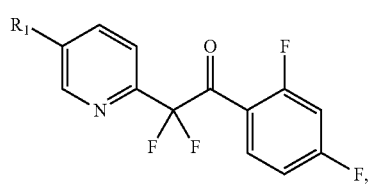
to provide epoxide 4,
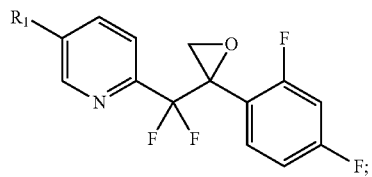
or a mixture thereof;
(v) forming the tetrazole of enantio-enriched amino-alcohol 4b or 4c:
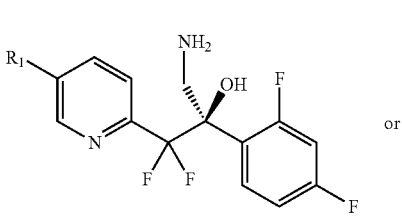

-continued

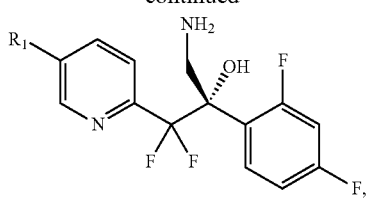

or a mixture thereof, to provide tetrazole 6 or 6a,

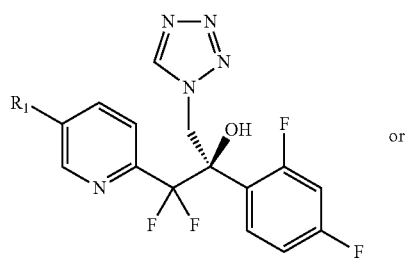

or

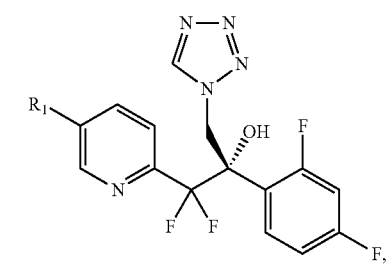

or a mixture thereof; and (vi) arylating tetrazole 6 or 6a,

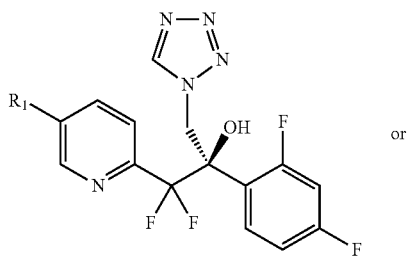

or

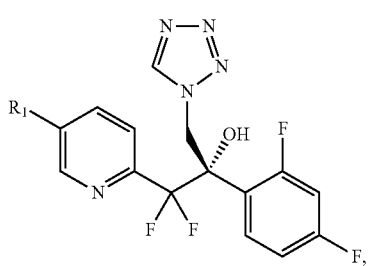

or a mixture thereof, to provide compound 1 or 1a,

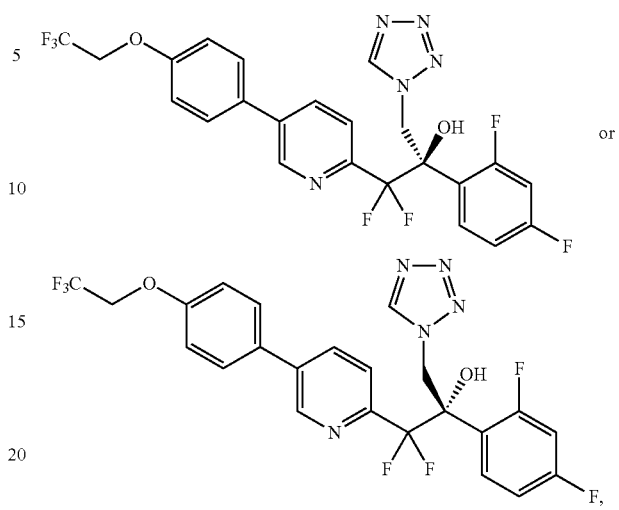

or a mixture thereof;

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare compound 1 or 1a, or a mixture thereof, comprising:

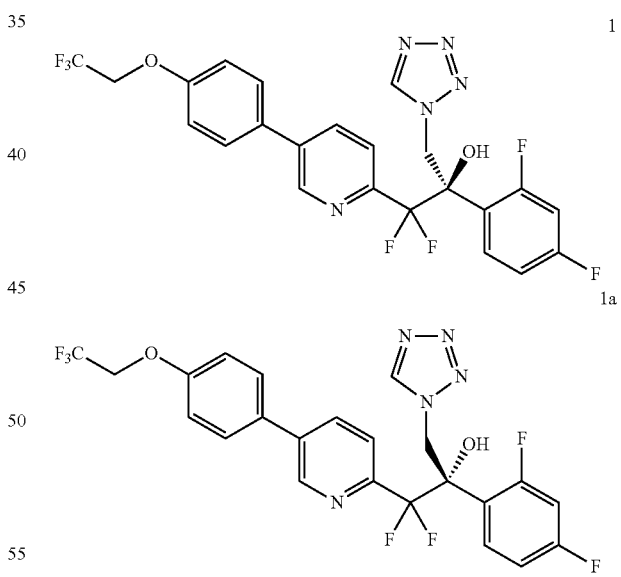

(i) displacing the ester portion of ester 2,

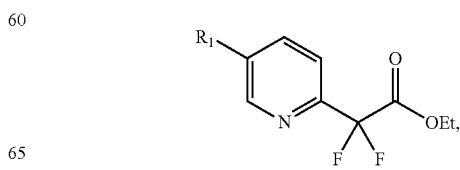

to provide ketone 3,

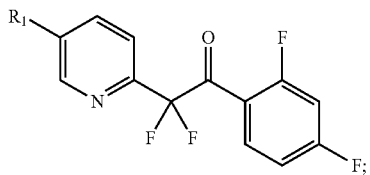

(ii) forming the epoxide of ketone 3,

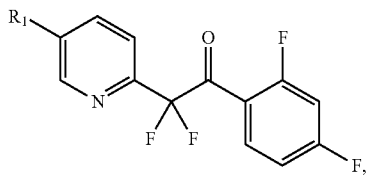

to provide epoxide 4,

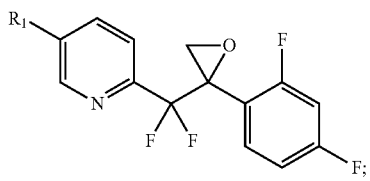

(iii) ring-opening epoxide 4,

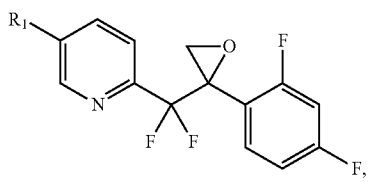

to provide amino-alcohol ±4b,

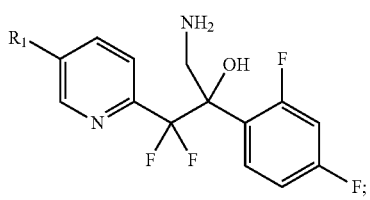

(iv) enriching the enantiomeric purity of amino-alcohol ±4b,

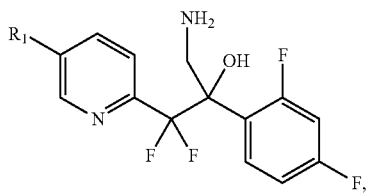

to provide enantio-enriched amino-alcohol 4b or 4c:

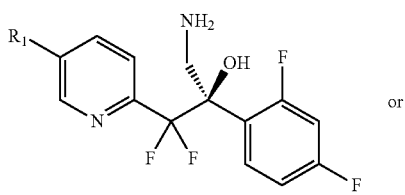

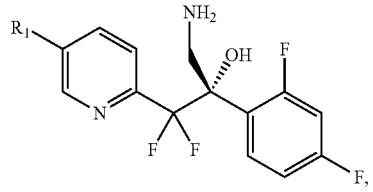

or a mixture thereof;

(v) arylating enantio-enriched amino-alcohol 4b or 4c,

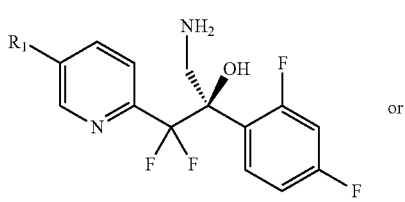

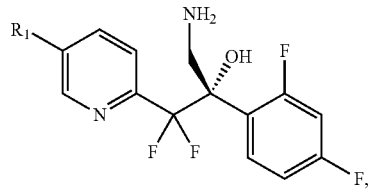

or a mixture thereof, to provide enantio-enriched amino-alcohol 1-6* or 1-7*,

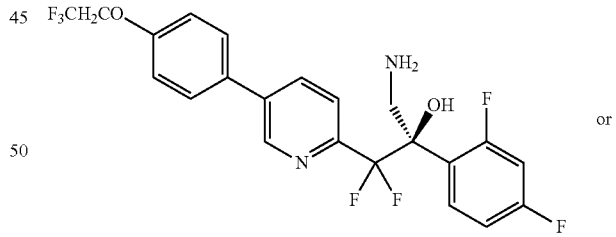

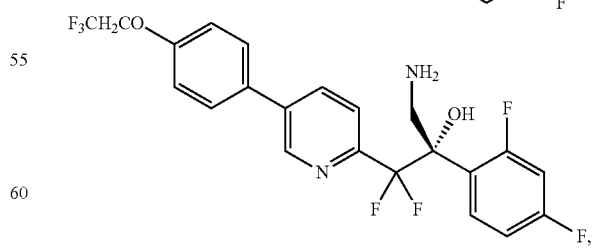

or a mixture thereof; and (vi) forming the tetrazole of enantio-enriched amino-alcohol 1-6* or 1-7*,

51

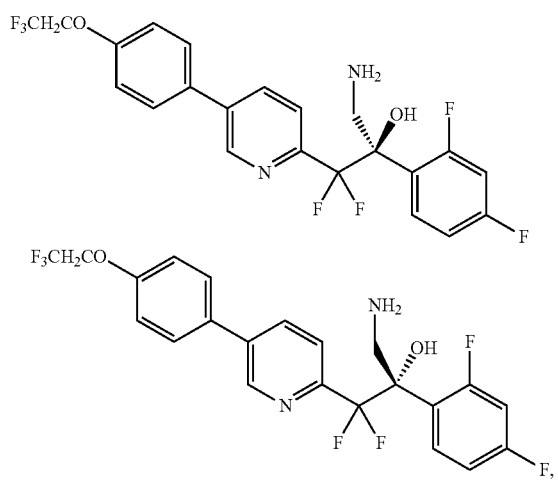

or a mixture thereof, to provide compound 1 or 1a,

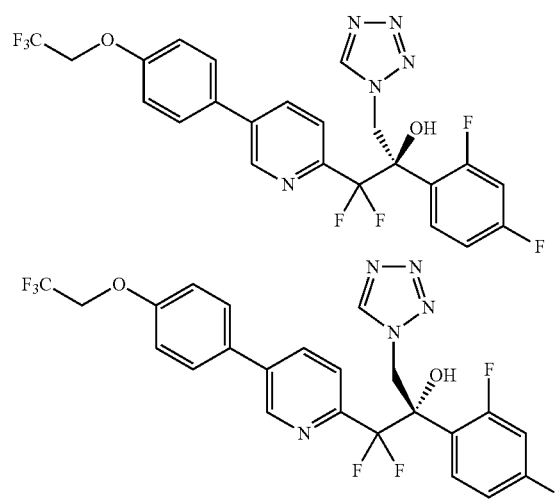

or a mixture thereof;
wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

In another aspect, the invention provides a process to prepare compound 1 or 1a, or a mixture thereof, comprising:

1

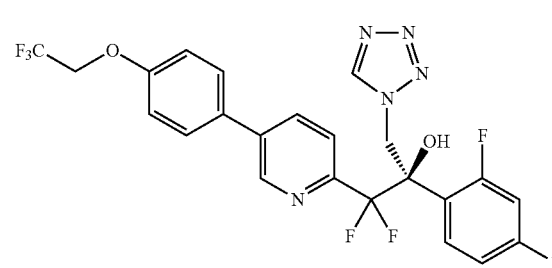

52

-continued

1a

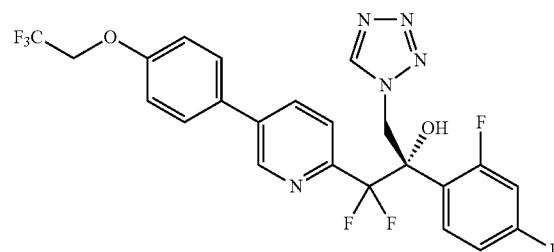

(i) displacing the ester portion of ester 2,

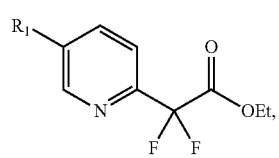

to provide ketone 3,

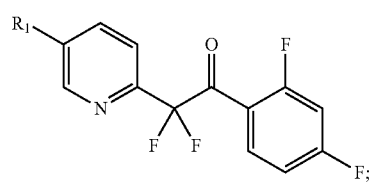

(ii) forming the epoxide of ketone 3,

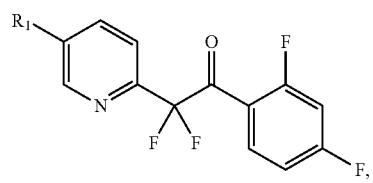

to provide epoxide 4,

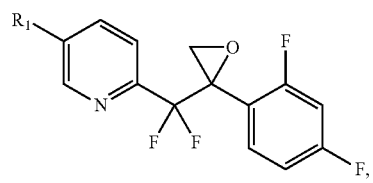

(iii) ring-opening epoxide 4, to provide amino-alcohol ±4b,

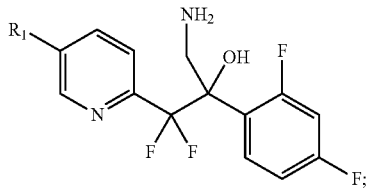

(iv) enriching the enantiomeric purity of amino-alcohol ±4b,

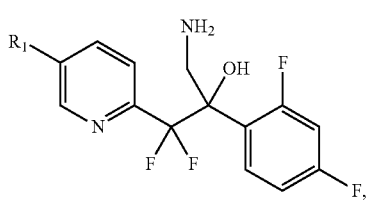

to provide enantio-enriched amino-alcohol 4b or 4c:

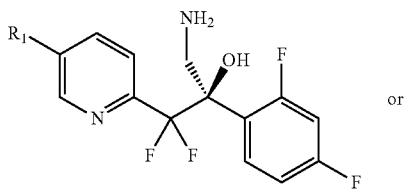

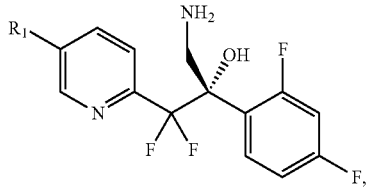

or a mixture thereof;

(v) arylating the enantio-enriched amino-alcohol 4b or 4c,

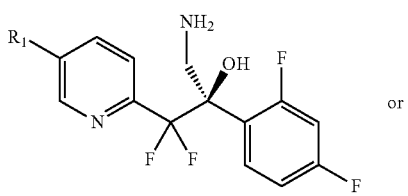

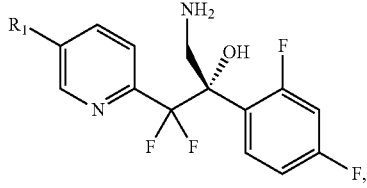

or a mixture thereof, to provide enantio-enriched amino-alcohol 1-6* or 1-7*,

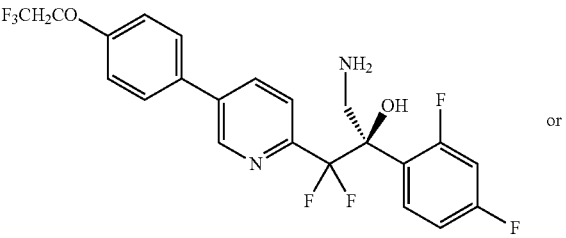

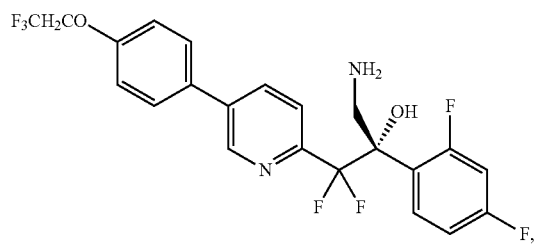

or a mixture thereof;

(vi) forming a salt of enantio-enriched amino-alcohol 1-6* or 1-7*,

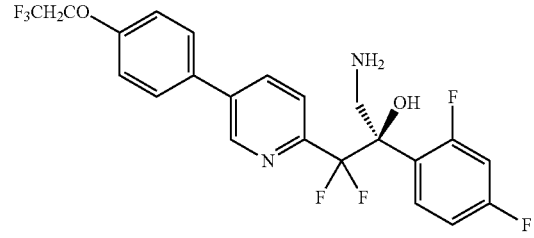

or a mixture thereof to provide XI or XIa,

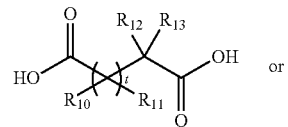

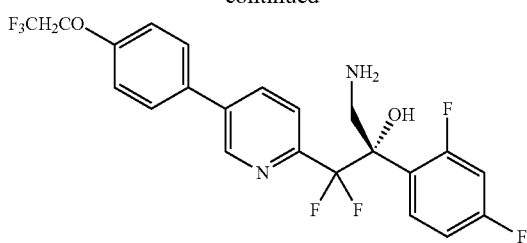

or a mixture thereof; and
(vii) forming the tetrazole of XI or XIa,

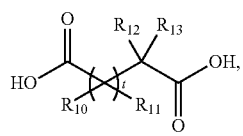

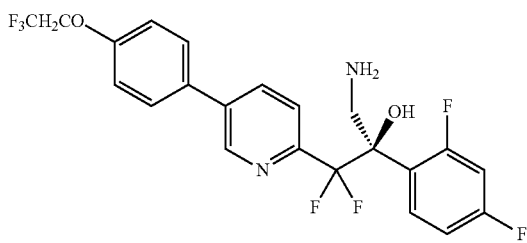

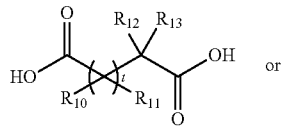

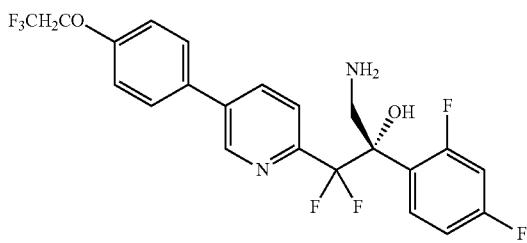

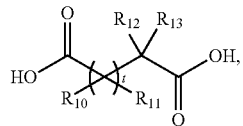

or a mixture thereof, to provide compound 1 or 1a,

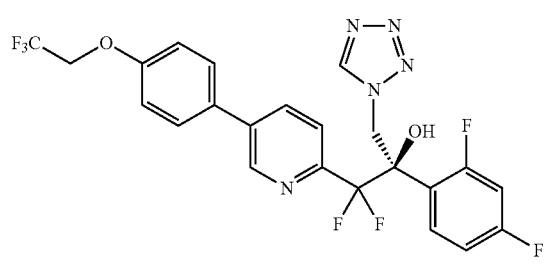

or

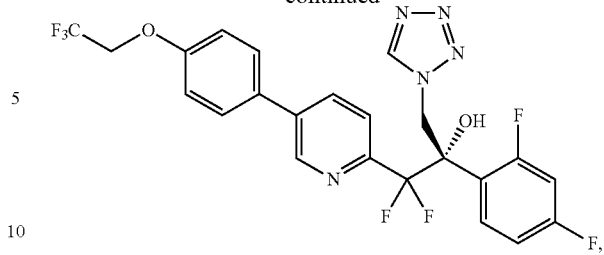

or a mixture thereof;
wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl;

each $R_{10}$ is independently H, optionally substituted alkyl, optionally substituted aryl, optionally substituted heteroaryl, optionally substituted cycloalkyl, optionally substituted heterocyclyl, optionally substituted arylalkyl, or optionally substituted heteroarylalkyl;

each $R_{11}$ is independently H, OH, optionally substituted alkyl, optionally substituted alkoxy, or OC(O)$R_{14}$;

each $R_{12}$ is independently H, optionally substituted alkyl, optionally substituted aryl, optionally substituted heteroaryl, optionally substituted cycloalkyl, optionally substituted heterocyclyl, optionally substituted arylalkyl, or optionally substituted heteroarylalkyl;

each $R_{13}$ is independently H, OH, optionally substituted alkyl, optionally substituted alkoxy, or OC(O)$R_{14}$;

each $R_{14}$ is independently H, optionally substituted alkyl, optionally substituted aryl, optionally substituted heteroaryl, optionally substituted cycloalkyl, optionally substituted heterocyclyl, optionally substituted arylalkyl, or optionally substituted heteroarylalkyl; and each t is independently 0, 1, 2, or 3. In another aspect, the salt of enantio-enriched amino-alcohol 4b or 4c,

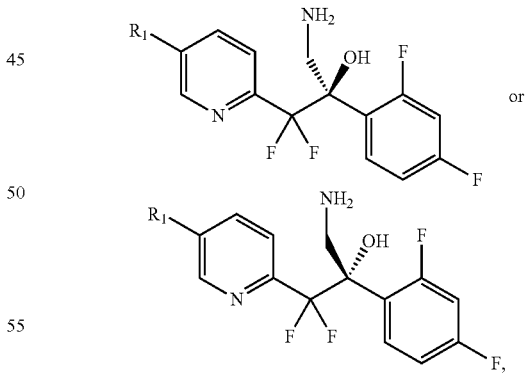

or a mixture thereof, from step (vi) is selected from the group consisting of maleic acid salt, malonic acid salt, succinic acid salt, fumaric acid salt, malic acid salt, tartaric acid salt, dibenzoyltartaric acid salt, di-p-toluoyltartaric acid salt, and mandelic acid salt. In a further aspect the salt is tartaric acid salt, di-p-toluoyltartaric acid salt, or malic acid salt. In another aspect, the salt is L-tartaric acid salt, D-di-p-toluoyltartaric acid salt, or D-malic acid salt. (preferably, L-tartaric acid salt or D-di-p-toluoyltartaric acid salt).

In another aspect, the invention provides a process to prepare compound 1 or 1a, or a mixture thereof, comprising:

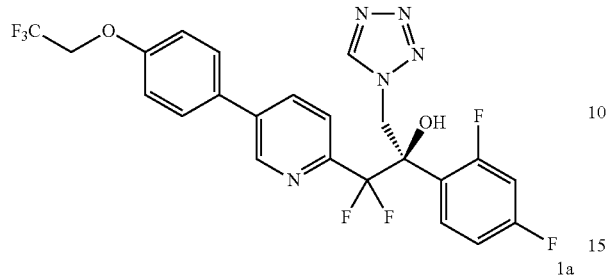
1

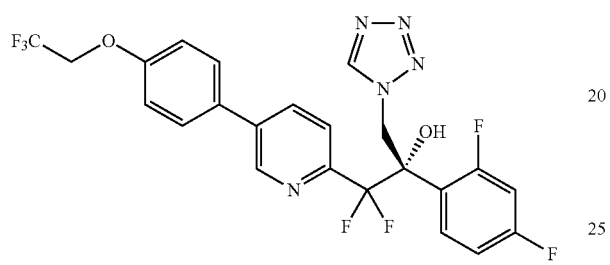
1a (i) displacing the ester portion of ester 2,

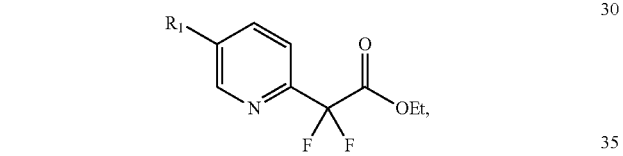

to provide morpholine amide 2b,

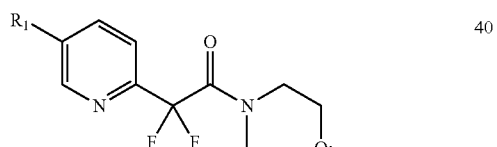

(ii) displacing the morpholino portion of morpholine amide 2b,

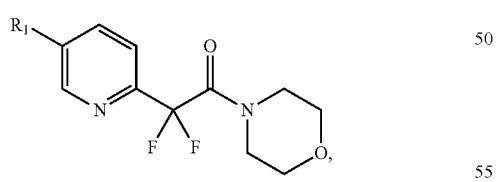

to provide ketone 3,

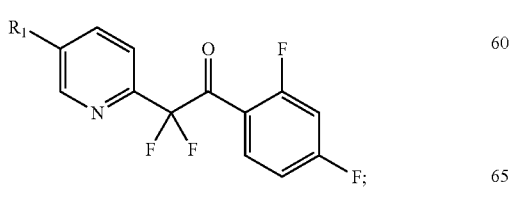

(iii) forming the epoxide of ketone 3,

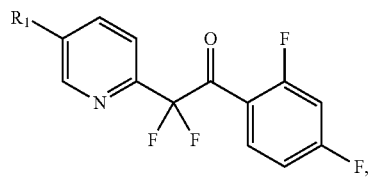

to provide epoxide 4,

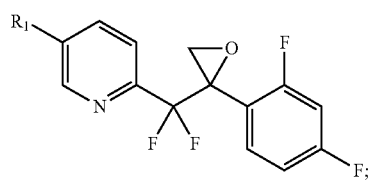

(iv) ring-opening epoxide 4,

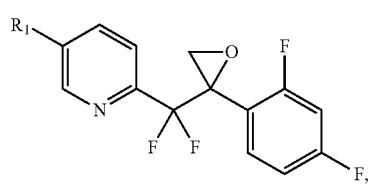

to provide amino-alcohol ±4b,

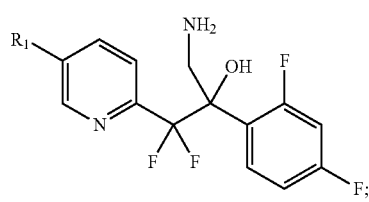

(v) enriching the enantiomeric purity of amino-alcohol ±4b,

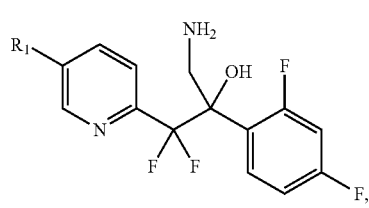

to provide enantio-enriched amino-alcohol 4b or 4c:

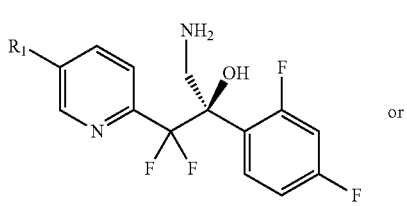 or

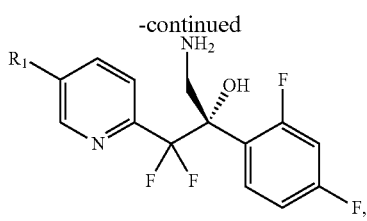
or a mixture thereof;
(vi) arylating the enantio-enriched amino-alcohol 4b or 4c,
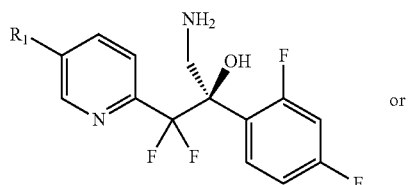
or
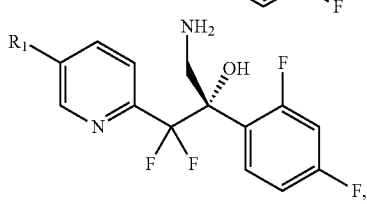
or a mixture thereof, to provide enantio-enriched amino-alcohol 1-6* or 1-7*,
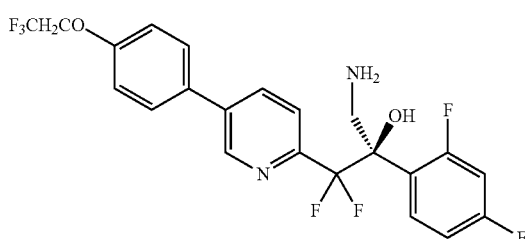
or
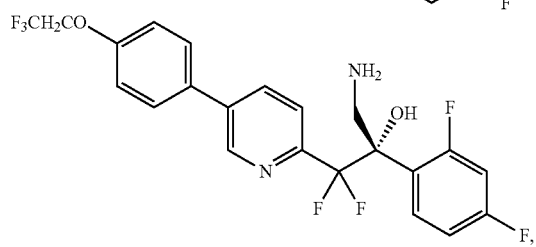
or a mixture thereof;
(vii) forming a salt of enantio-enriched amino-alcohol 1-6* or 1-7*,
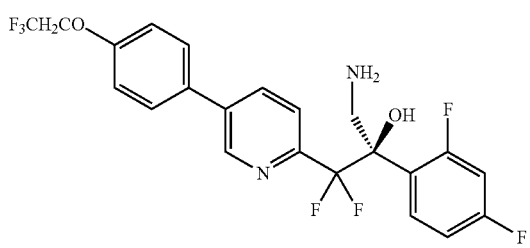
or
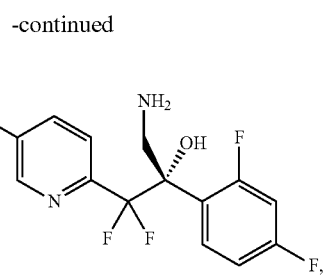
or a mixture thereof to provide XI or XIa,
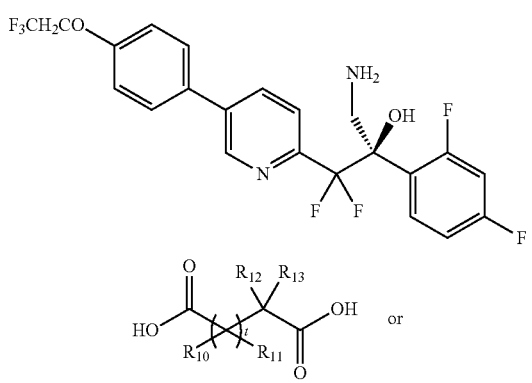
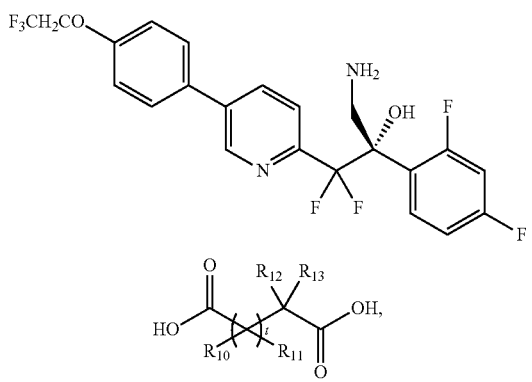
or a mixture thereof; and
(viii) forming the tetrazole of XI or XIa,
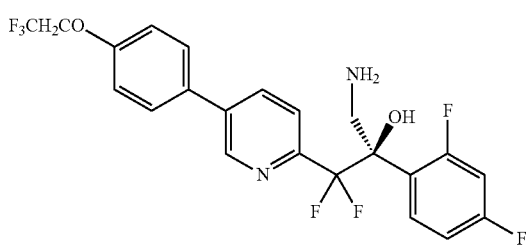
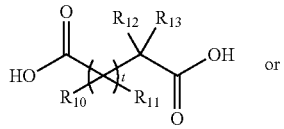 or -continued

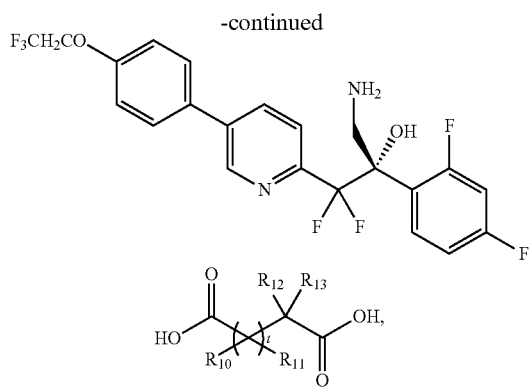

or a mixture thereof, to provide compound 1 or 1a,

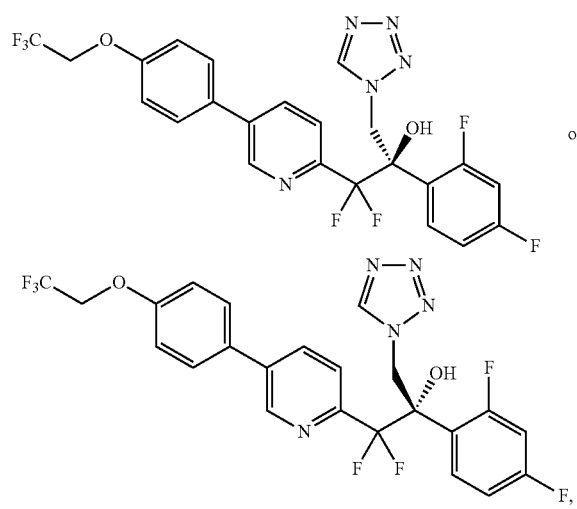

or a mixture thereof;

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl;

each $R_{10}$ is independently H, optionally substituted alkyl, optionally substituted aryl, optionally substituted heteroaryl, optionally substituted cycloalkyl, optionally substituted heterocyclyl, optionally substituted arylalkyl, or optionally substituted heteroarylalkyl;

each $R_{11}$ is independently H, OH, optionally substituted alkyl, optionally substituted alkoxy, or OC(O)$R_{14}$;

each $R_{12}$ is independently H, optionally substituted alkyl, optionally substituted aryl, optionally substituted heteroaryl, optionally substituted cycloalkyl, optionally substituted heterocyclyl, optionally substituted arylalkyl, or optionally substituted heteroarylalkyl;

each $R_{13}$ is independently H, OH, optionally substituted alkyl, optionally substituted alkoxy, or OC(O)$R_{14}$;

each $R_{14}$ is independently H, optionally substituted alkyl, optionally substituted aryl, optionally substituted heteroaryl, optionally substituted cycloalkyl, optionally substituted heterocyclyl, optionally substituted arylalkyl, or optionally substituted heteroarylalkyl; and each t is independently 0, 1, 2, or 3. In another aspect, the salt of enantio-enriched amino-alcohol 4b or 4c,

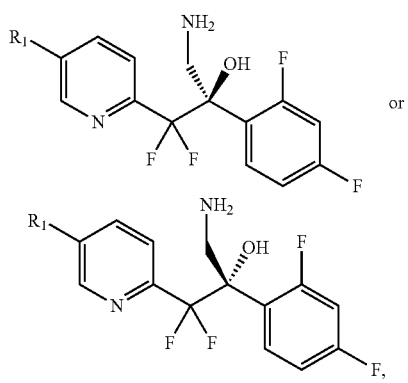

or a mixture thereof, from step (vii) is selected from the group consisting of maleic acid salt, malonic acid salt, succinic acid salt, fumaric acid salt, malic acid salt, tartaric acid salt, dibenzoyltartaric acid salt, di-p-toluoyltartaric acid salt, and mandelic acid salt. In a further aspect the salt is tartaric acid salt, di-p-toluoyltartaric acid salt, or malic acid salt. In another aspect, the salt is L-tartaric acid salt, D-di-p-toluoyltartaric acid salt, or D-malic acid salt. (preferably, L-tartaric acid salt or D-di-p-toluoyltartaric acid salt).

In another aspect, Z from any of the embodiments presented herein is phenyl, p-tolyl, methyl, or ethyl.

In another aspect, the crystallization solvent or crystallization solvent mixture from any of the embodiments presented herein is ethyl acetate, isopropyl acetate, ethanol, methanol, or acetonitrile, or combinations thereof.

In another aspect, the crystallization co-solvent or crystallization co-solvent mixture from any of the embodiments presented herein is pentane, methyl t-butylether, hexane, heptane, or toluene, or combinations thereof.

In another aspect, any of the embodiments presented herein may comprise repeating the enantio-enrichment step(s) until desired level of enantio-enrichment is attained.

In another aspect, Y in any of the embodiments presented herein may be mesylate or tosylate.

In another aspect, any of the embodiments presented herein may comprise substituting morpholine-amide 2b with amide 2c.

In another aspect, any of the embodiments presented herein may comprise substituting ethyl ester 2 with ester 2d.

In other aspects, the invention provides a compound of any of the formulae herein, wherein the compound inhibits (or is identified to inhibit) lanosterol demethylase (CYP51).

In another aspect, the invention provides a pharmaceutical composition comprising a compound of any formulae herein and a pharmaceutically acceptable carrier.

In other aspects, the invention provides a method of modulating metalloenzyme activity in a subject, comprising contacting the subject with a compound of any formulae herein, in an amount and under conditions sufficient to modulate metalloenzyme activity.

In one aspect, the invention provides a method of treating a subject suffering from or susceptible to a metalloenzyme-related disorder or disease, comprising administering to the subject an effective amount of a compound or pharmaceutical composition of any formulae herein.

In another aspect, the invention provides a method of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound or pharmaceutical composition of any formulae herein, such that said subject is treated for said disorder.

In another aspect, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of any formulae herein, such that metalloenzyme activity in said subject is modulated (e.g., down regulated, inhibited). In another aspect, the compounds delineated herein preferentially target cancer cells over nontransformed cells.

DETAILED DESCRIPTION

Definitions

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The sp² or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "haloalkoxy" refers to an —O-alkyl radical that is substituted by one or more halo substituents. Examples of haloalkoxy groups include trifluoromethoxy, and 2,2,2-trifluoroethoxy.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF₃), sulfonates (e.g., mesyl, tosyl), acetamides (e.g., —NHC(O)Me), carbamates (e.g., N(Me)C(O)Ot-Bu), phosphonates (e.g., —OP(O)(OEt)₂), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N"-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, 2ⁿᵈ *Edition*, Carlson R, Ed, 2005; Elsevier Science Ltd.; Jäh- nisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database. The invention includes the intermediate compounds used in making the compounds of the formulae herein as well as methods of making such compounds and intermediates, including without limitation those as specifically described in the examples herein.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Pharmaceutical Compositions

In one aspect, the invention provides a pharmaceutical composition comprising a compound of any formulae herein and a pharmaceutically acceptable carrier.

In another embodiment, the invention provides a pharmaceutical composition further comprising an additional therapeutic agent. In a further embodiment, the additional therapeutic agent is an anti-cancer agent, antifungal agent, cardiovascular agent, antiinflammatory agent, chemotherapeutic agent, an anti-angiogenesis agent, cytotoxic agent, an anti-proliferation agent, metabolic disease agent, opthalmologic disease agent, central nervous system (CNS) disease agent, urologic disease agent, or gastrointestinal disease agent.

In one aspect, the invention provides a kit comprising an effective amount of a compound of any formulae herein, in unit dosage form, together with instructions for administering the compound to a subject suffering from or susceptible to a metalloenzyme-mediated disease or disorder, including cancer, solid tumor, cardiovascular disease, inflammatory disease, infectious disease. In other embodiments the disease, disorder or symptom thereof is metabolic disease, opthalmologic disease, central nervous system (CNS) disease, urologic disease, or gastrointestinal disease.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound (s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease. Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

Agricultural Applications

The compounds and compositions herein can be used in methods of modulating metalloenzyme activity in a microorganism on a plant comprising contacting a compound (or composition) herein with the plant (e.g., seed, seedling, grass, weed, grain). The compounds and compositions herein can be used to treat a plant, field or other agricultural area (e.g., as herbicides, pesticides, growth regulators, etc.) by administering the compound or composition (e.g., contacting, applying, spraying, atomizing, dusting, etc.) to the subject plant, field or other agricultural area. The administration can be either pre- or post-emergence. The administration can be either as a treatment or preventative regimen.

EXAMPLES

The present invention will now be demonstrated using specific examples that are not to be construed as limiting.

General Experimental Procedures

Definitions of variables in the structures in schemes herein are commensurate with those of corresponding positions in the formulae delineated herein.

Synthesis of 1 or 1a

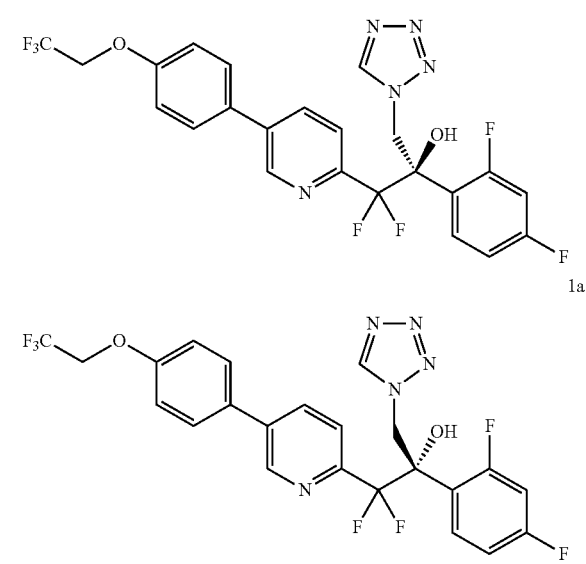

A process to prepare enantiopure compound 1 or 1a is disclosed. Syntheses of 1 or 1a may be accomplished using the example syntheses that are shown below (Schemes 1-4). The preparation of precursor ketone 3-Br is performed starting with reaction of 2,5-dibromo-pyridine with ethyl 2-bromo-difluoroacetate to produce ester 2-Br. This ester can be reacted with morpholine to furnish morpholine amide 2b-Br, followed by arylation to provide ketone 3-Br. Alternatively, ketone 3-Br can be afforded directly from ester 2-Br as shown in Scheme 1.

Scheme 1. Synthesis of ketone 3-Br

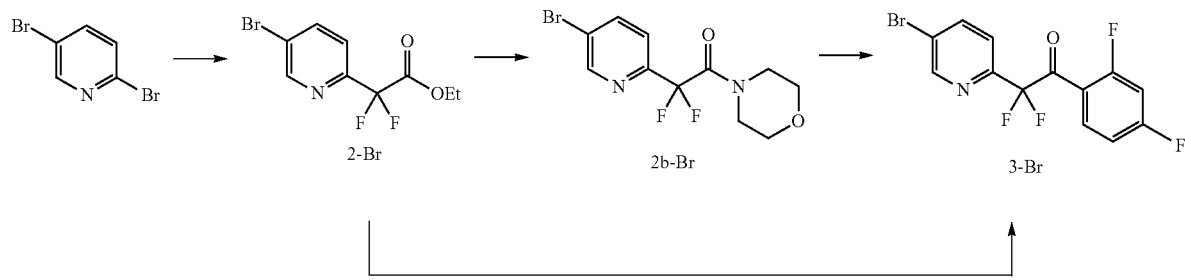

Ketone 3 may be prepared in an analogous fashion as described in Scheme 1 starting from corresponding substituted 2-bromo-pyridines, which can be prepared according to synthetic transformations known in the art and contained in the references cited herein (Scheme 2).

the like) in a suitable solvent (e.g., acetonitrile, isopropanol, EtOH, or mixtures thereof, or a mixture of any of these with water or MeOH; preferably acetonitrile or a mixture of acetonitrile and MeOH or isopropanol, such as 90:10, 85:15, or 80:20 mixture) to afford compounds 4b (or 4c, the Scheme 2. Synthesis of ketone 3

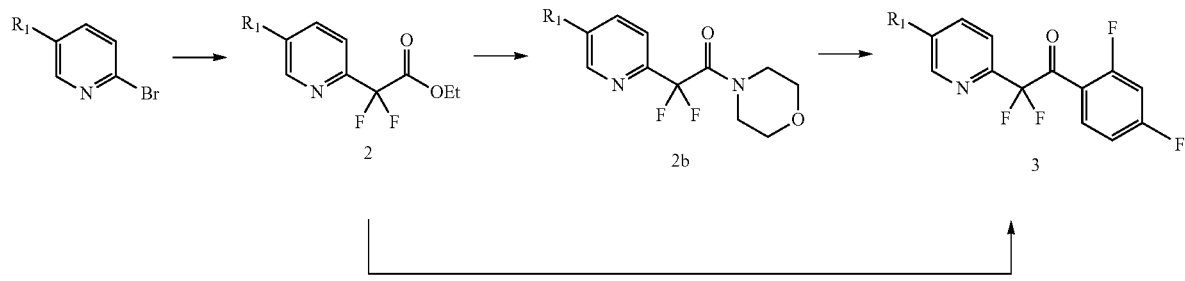

$R_1$ = halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

Alternatively, compound 1 (or 1a, the enantiomer of 1, or mixtures thereof) can be prepared according to Scheme 3 utilizing amino-alcohols ±4b or ±1-6. Epoxides 4 and 5 can be prepared by reacting ketones 3 and 1-4 with trimethylsulfoxonium iodide (TMSI) in the presence of a base (e.g., potassium t-butoxide) in a suitable solvent or a mixture of solvents (e.g., DMSO or THF). Also, as indicated in Scheme 3, any of pyridine compounds, 3, 4, ±4b, 4b, or 6, can be converted to the corresponding 4-CF$_3$CH$_2$O-Ph analogs (e.g., 1-4, 5, ±1-6, 1-6*, or 1 or the corresponding enantiomers, or mixtures thereof) by cross-coupling with 4,4,5,5-tetramethyl-2-(4-(2,2,2-trifluoroethoxy)phenyl)-1,3,2-dioxaborolane (or the corresponding alkyl boronates or boronic acid or the like), in a suitable solvent system (e.g., an organic-aqueous solvent mixture), in the presence of a transition metal catalyst (e.g., (dppf)PdCl$_2$; dppf=1,1'-(diphenylphosphino)ferrocene), and in the presence of a base (e.g., KHCO$_3$, K$_2$CO$_3$, Cs$_2$CO$_3$, or Na$_2$CO$_3$, or the like). Epoxides 4 and 5 can then be converted into amino-alcohols ±4b and ±1-6 through ammonia-mediated epoxide opening using ammonia in a suitable solvent (e.g., MeOH, EtOH, or water). Racemic amino-alcohols ±4b and ±1-6 can then be enantio-enriched by exposure to a chiral acid (e.g., tartaric acid, di-benzoyltartaric acid, or di-p-toluoyltartaric acid or enantiomer of 4b, or mixtures thereof) or 1-6* (or 1-7*, the enantiomer of 1-6*, or mixtures thereof). Subsequent treatment with TMS-azide in the presence of trimethylorthoformate and sodium acetate in acetic acid would yield compounds 6 (or 6a, the enantiomer of 6, or mixtures thereof) or 1 (or 1a, the enantiomer of 1, or mixtures thereof) (U.S. Pat. No. 4,426,531).

Scheme 3. Synthesis of 1 or 1a via TMSI Epoxidation Method

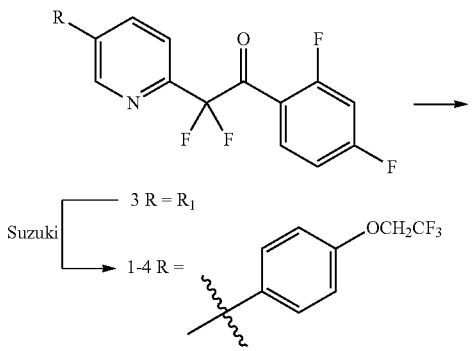

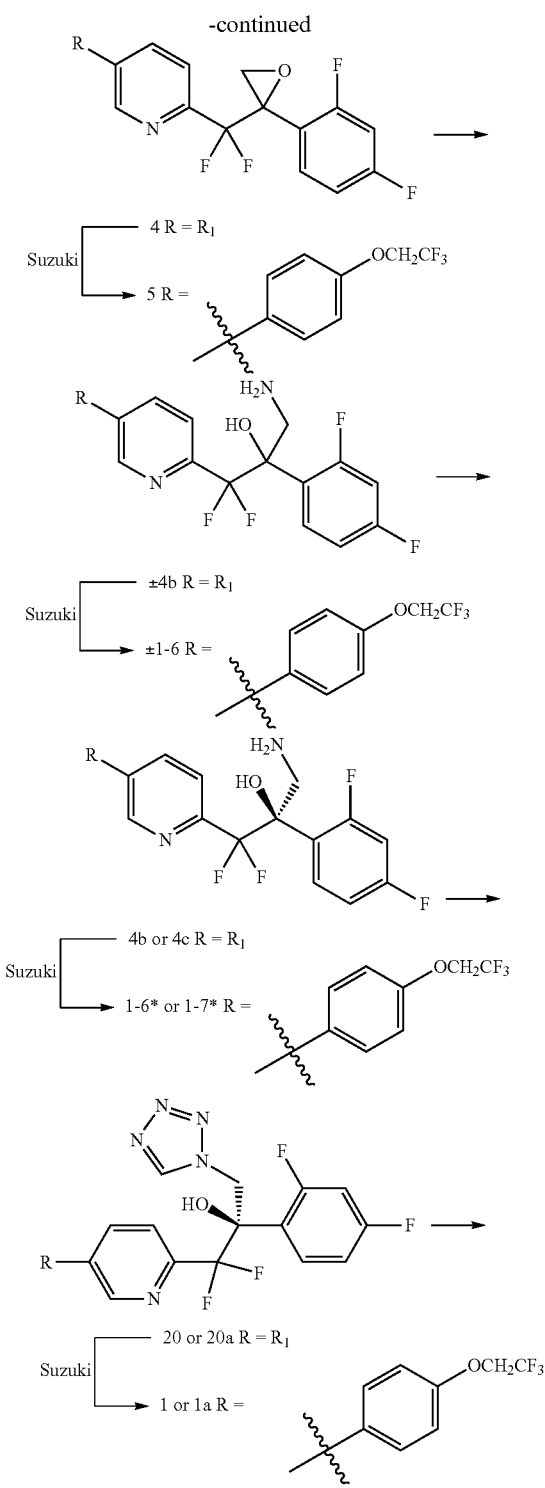

$R_1$ = halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

Compound 1 (or 1a, the enantiomer of 1, or mixtures thereof) prepared by any of the methods presented herein can be converted to a sulfonic salt of formula IX (or IXa, the enantiomer of IX, or mixtures thereof), as shown in Scheme 4. This can be accomplished by a) combining compound 1 (or 1a, the enantiomer of 1, or mixtures thereof), a crystallization solvent or crystallization solvent mixture (e.g., EtOAc, iPrOAc, EtOH, MeOH, or acetonitrile, or combinations thereof), and a sulfonic acid

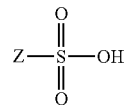

(e.g., Z=Ph, p-tolyl, Me, or Et), b) diluting the mixture with an appropriate crystallization co-solvent or crystallization co-solvent mixture (e.g., pentane, methyl t-butylether, hexane, heptane, or toluene, or combinations thereof), and c) filtering the mixture to obtain a sulfonic acid salt of formula IX (or IXa, the enantiomer of IX, or mixtures thereof).

Scheme 4. Synthesis of a Sulfonic Acid Salt of Compound 1 or 1a

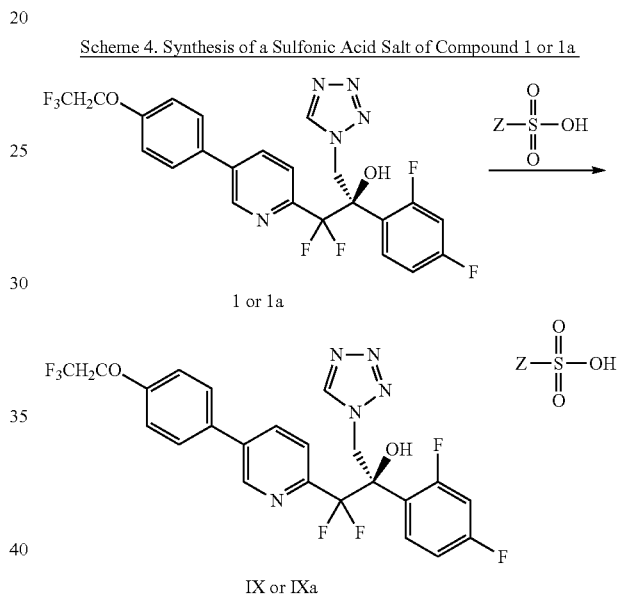

The following describes the HPLC method used in assessing HPLC purity of the examples and intermediates presented below:

Column: Waters XBridge Shield RP18, 4.6×150 mm, 3.5 μm
Mobile Phase: A=0.05% TFA/H₂O, B=0.05% TFA/ACN
Autosampler flush: 1:1 ACN/H₂O
Diluent: 1:1 ACN/H₂O
Flow Rate: 1.0 ml/min
Temperature: 45° C.
Detector: UV 275 nm
Pump Parameters:

| Step | Segment Time | A | B | Curve |
|---|---|---|---|---|
| 0 | 0.5 | 80.0 | 20.0 | 0 |
| 1 | 15.0 | 60.0 | 40.0 | 1 |
| 2 | 10.0 | 15.0 | 85.0 | 1 |
| 3 | 5.0 | 0.0 | 100.0 | 1 |
| 4 | 2.0 | 0.0 | 100.0 | 0 |
| 5 | 8.0 | 80.0 | 20.0 | 0 |

Example 1

Preparation of ethyl 2-(5-bromopyridin-2-yl)-2,2-difluoroacetate (2-Br)

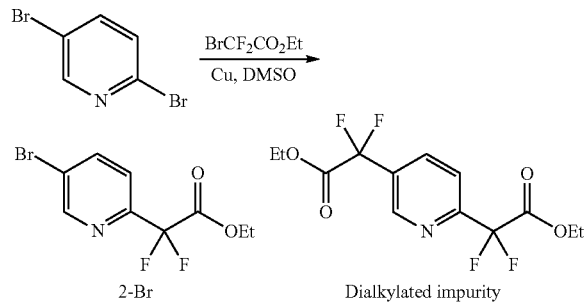

In a clean multi-neck round bottom flask, copper powder (274.7 g, 2.05 eq) was suspended in dimethyl sulfoxide (3.5 L, 7 vol) at 20-35° C. Ethyl bromodifluoroacetate (449 g, 1.05 eq) was slowly added to the reaction mixture at 20-25° C. and stirred for 1-2 h. 2, 5-dibromopyridine (500 g, 1 eq) was added to the reaction mixture and the temperature was increased to 35-40° C. The reaction mixture was maintained at this temperature for 18-24 h and the reaction progress was monitored by GC.

After the completion of the reaction, ethyl acetate (7 L, 14 vol) was added to the reaction mixture and stirring was continued for 60-90 min at 20-35° C. The reaction mixture was filtered through a Celite bed (100 g; 0.2 times w/w Celite and 1 L; 2 vol ethyl acetate). The reactor was washed with ethyl acetate (6 L, 12 vol) and the washings were filtered through a Celite bed. The Celite bed was finally washed with ethyl acetate (1 L, 2 vol) and all the filtered mother liquors were combined. The pooled ethyl acetate solution was cooled to 8-10° C., washed with the buffer solution (5 L, 10 vol) below 15° C. (Note: The addition of buffer solution was exothermic in nature. Controlled addition of buffer was required to maintain the reaction mixture temperature below 15° C.). The ethyl acetate layer was washed again with the buffer solution until (7.5 L; 3×5 vol) the aqueous layer remained colorless. The organic layer was washed with a 1:1 solution of 10% w/w aqueous sodium chloride and the buffer solution (2.5 L; 5 vol). The organic layer was then transferred into a dry reactor and the ethyl acetate was distilled under reduced pressure to get crude 2-Br.

The crude 2-Br was purified by high vacuum fractional distillation and the distilled fractions having 2-Br purity greater than 93% (with the dialkylated not more than 2% and starting material less than 0.5%) were pooled together to afford 2-Br.

Yield after distillation: 47.7% with >93% purity by GC (pale yellow liquid). Another 10% yield was obtained by re-distillation of impure fractions resulting in overall yield of ~55-60%.

$^1$H NMR: δ values with respect to TMS (DMSO-$d_6$; 400 MHz): 8.85 (1H, d, 1.6 Hz), 8.34 (1H, dd, J=2.0 Hz, 6.8 Hz), 7.83 (1H, d, J=6.8 Hz), 4.33 (2H, q, J=6.0 Hz), 1.22 (3H, t, J=6.0 Hz). $^{13}$C NMR: 162.22 (t, —C=O), 150.40 (Ar—C—), 149.35 (t, Ar—C), 140.52 (Ar—C), 123.01 (Ar—C), 122.07 (Ar—C), 111.80 (t, —CF), 63.23 (—OCH$_2$—), 13.45 (—CH$_2$CH$_3$).

Example 2

Preparation of 2-(5-bromopyridin-2-yl)-1-(2,4-difluorophenyl)-2,2-difluoroethanone (3-Br)

A. One-step Method

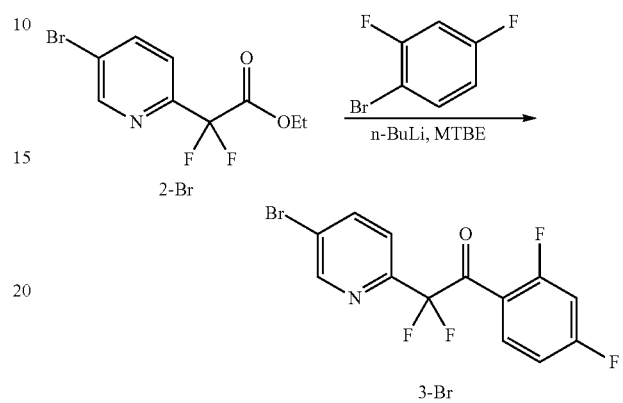

1-Bromo-2,4-difluorobenzene (268.7 g; 1.3 eq) was dissolved in methyl tert butyl ether (MTBE, 3.78 L, 12.6 vol) at 20-35° C. and the reaction mixture was cooled to −70 to −65° C. using acetone/dry ice bath. n-Butyl lithium (689 mL, 1.3 eq; 2.5 M) was then added to the reaction mixture maintaining the reaction temperature below −65° C. (Note: Controlled addition of the n-Butyl Lithium to the reaction mixture was needed to maintain the reaction mixture temperature below −65° C.). After maintaining the reaction mixture at this temperature for 30-45 min, 2-Br (300 g, 1 eq) dissolved in MTBE (900 mL, 3 vol) was added to the reaction mixture below −65° C. The reaction mixture was continued to stir at this temperature for 60-90 min and the reaction progress was monitored by GC.

The reaction was quenched by slow addition of 20% w/w ammonium chloride solution (750 mL, 2.5 vol) below −65° C. The reaction mixture was gradually warmed to 20-35° C. and an additional amount of 20% w/w ammonium chloride solution (750 mL, 2.5 vol) was added. The aqueous layer was separated, the organic layer was washed with a 10% w/w sodium bicarbonate solution (600 mL, 2 vol) followed by a 5% sodium chloride wash (600 mL, 2 vol). The organic layer was dried over sodium sulfate (60 g; 0.2 times w/w), filtered and the sodium sulfate was washed with MTBE (300 mL, 1 vol). The organic layer along with washings was distilled below 45° C. under reduced pressure until no more solvent was collected in the receiver. The distillation temperature was increased to 55-60° C., maintained under vacuum for 3-4 h and cooled to 20-35° C. to afford 275 g (73.6% yield, 72.71% purity by HPLC) of 3-Br as a pale yellow liquid.

$^1$H NMR: δ values with respect to TMS (DMSO-$d_6$; 400 MHz): 8.63 (1H, d, 1.6 Hz), 8.07-8.01 (2H, m, 2×Ar—H), 7.72 (1H, d, J=6.8 Hz, Ar—H), 7.07-6.82 (1H, m, Ar—H), 6.81-6.80 (1H, m, Ar—H). $^{13}$C NMR: 185.60 (t, —C=O), 166.42 (dd, Ar—C—), 162.24 (dd, Ar—C), 150.80 (Ar—C), 150.35 (Ar—C), 140.02 (Ar—C), 133.82 (Ar—C), 123.06 (Ar—C), 1122.33 (Ar—C), 118.44 (Ar—C), 114.07 (—CF$_2$—), 122.07 (Ar—C), 105.09 (Ar—C).

B. Two-step Method via 2b-Br

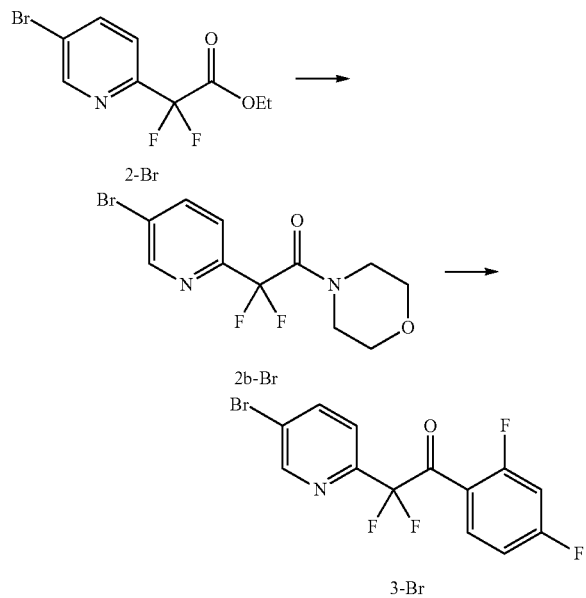

2-Br (147.0 g) was dissolved in n-heptane (1.21 L) and transferred to a 5-L reactor equipped with overhead stirrer, thermocouple, condenser and addition funnel. Morpholine (202 ml) was added. The solution was heated to 60° C. and stirred overnight. The reaction was complete by HPLC analysis (0.2% 2-Br; 94.7% 2b-Br). The reaction was cooled to room temperature and 1.21 L of MTBE was added. The solution was cooled to ~4° C. and quenched by slow addition of 30% citric acid (563 ml) to maintain the internal temperature <15° C. After stirring for one hour the layers were allowed to settle and were separated (Aq. pH=5). The organic layer was washed with 30% citric acid (322 ml) and 9% NaHCO$_3$ (322 ml, aq. pH 7+ after separation). The organic layer was concentrated on the rotary evaporator (Note 1) to 454 g (some precipitation started immediately and increased during concentration). After stirring at room temperature the suspension was filtered and the product cake was washed with n-heptane (200 ml). The solid was dried in a vacuum oven at room temperature to provide 129.2 g (77%) dense powder. The purity was 96.5% by HPLC analysis.

To a 1-L flask equipped with overhead stirring, thermocouple, condenser and addition funnel was added magnesium turnings (14.65 g), THF (580 ml) and 1-bromo-2,4-difluorobenzene (30.2 g, 0.39 equiv). The mixture was stirred until the reaction initiated and self-heating brought the reaction temperature to 44° C. The temperature was controlled with a cooling bath as the remaining 1-bromo-2,4-difluorobenzene (86.1 g, 1.11 equiv) was added over about 30 min. at an internal temperature of 35-40° C. The reaction was stirred for 2 hours while gradually cooling to room temperature. The dark yellow solution was further cooled to 12° C.

During the Grignard formation, a jacketed 2-L flask equipped with overhead stirring, thermocouple, and addition funnel was charged with morpholine amide 2b-Br (129.0 g) and THF (645 ml). The mixture was stirred at room temperature until the solid dissolved, and then the solution was cooled to −8.7° C. The Grignard solution was added via addition funnel over about 30 min. at a temperature of −5 to 0° C. The reaction was stirred at 0° C. for 1 hour and endpointed by HPLC analysis. The reaction mixture was cooled to −5° C. and quenched by slow addition of 2N HCl over 1 hour at ≤10° C. The mixture was stirred for 0.5 h then the layers were allowed to settle and were separated. The aqueous layer was extracted with MTBE (280 ml). The combined organic layers were washed with 9% NaHCO$_3$ (263 g) and 20% NaCl (258 ml). The organic layer was concentrated on the rotary evaporator with THF rinses to transfer all the solution to the distillation flask. Additional THF (100 ml) and toluene (3×100 ml) were added and distilled to remove residual water from the product. After drying under vacuum, the residue was 159.8 g of a dark brown waxy solid (>theory). The purity was approximately 93% by HPLC analysis.

Grignard Formation/Coupling Reaction 2:

Magnesium (0.022 kg, 0.903 mol) 1-bromo-2,4-difluorobenzene (0.027 kg, 0.14 mol) and tetrahydrofuran (THF) (1.4 L) were charged to a 2 L reactor fitted with a nitrogen inlet/outlet, 0.25 L dropping funnel, temperature probe and reflux condenser. After stirring for ca. 40 min at 22° C., the reaction initiated and was allowed to reach 35° C. Cooling was applied and further 1-bromo-2,4-difluorobenzene (0.153 kg, 0.79 mol) was added at 35-40° C. over 0.5 hr. On completion of the addition, the reaction was stirred at 35-40° C. for a further 1 h before cooling solution of the Grignard reagent to 20-25° C. over 1 hr. During the 1 hr cooling period, 2b-Br (0.2 kg, 0.62 mol) and THF (0.8 L) were charged to a 5 L reactor fitted with a nitrogen inlet/outlet, 0.5 L dropping funnel, temperature probe and reflux condenser and stirred at 15-20° C. to give a solution before cooling to −5 to 0° C.

The Grignard reagent was added to the solution of morpholine amide in THF at −3 to 2° C. over 50 min and the solution stirred at approximately 0° C. for 1 hr. A sample of the reaction mixture was submitted for GC analysis. A 1 ml sample was quenched into 2 M hydrochloric acid solution (5 ml) and extracted with MTBE (2 ml). The organic layer was submitted for analysis, which indicated 0.76% morpholine amide remaining.

The reaction was quenched by the addition of 2 M hydrochloric acid solution (1 L) over 0.75 hr at less than 10° C. and stirred for a further 0.5 hr. Stirring was stopped and the phases allowed to separate. The lower aqueous layer was removed and extracted with tert-butylmethyl ether (MTBE) (0.4 L). The combined organic layers were washed with saturated sodium hydrogen carbonate solution (0.4 L) and saturated sodium chloride solution (0.4 L). The solvent was evaporated under vacuum at less than 50° C. and co-distilled with portions of toluene (0.2 L) until the water content by Karl Fischer (KF) analysis was less than 0.1%.

Toluene (0.37 L) and n-heptane (0.37 L) were added to the residue together with SilicaFlash P60 (40-63 micron) (0.11 kg), and the reaction stirred at 20-25° C. for 1 hr. The reaction was filtered and washed with toluene/n-heptane (1:1) (2 L). The solvent was evaporated at <50° C. and solvent swapped in to THF to give an approximately 36 wt % solution of 3-Br. Gravimetric analysis of a sample of the toluene/n-heptane solution prior to evaporation indicated a mass yield of 0.21 kg (98.5%). GC assay of this material was 95.34%, to give a contained yield of 93.9%. GC (AUC) analysis of an evaporated sample was 94.5%, and HPLC (AUC) was 97.1%.

Example 3

Preparation of 5-bromo-2-((2-(2,4-difluorophenyl)oxiran-2-yl)difluoromethyl)pyridine (4-Br)

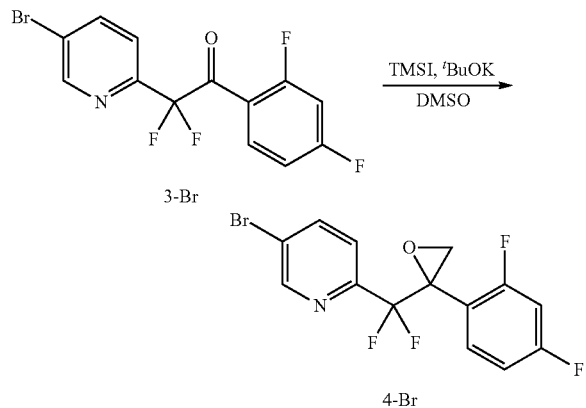

Trimethyl sulfoxonium iodide (TMSI, 37.93 g; 1.2 eq) was added into a mixture of dimethyl sulfoxide (300 mL, 5 vol) and tetrahydrofuran (500 mL, 10 vol) at 20-35° C. (pale yellow suspension was observed). A potassium tert-butoxide solution in THF (172.5 mL, 1.2 eq) was then added into the reaction mixture and stirred for 60-90 min at 20-35° C., resulting in a clear solution. The reaction mixture was then cooled to 0-5° C. and a solution of 3-Br (50 g, 1 eq) in tetrahydrofuran (150 mL, 3 vol) was added maintaining the reaction mixture temperature below 15° C. The reaction progress was monitored by GC. The reaction was quenched by adding 1M hydrochloric acid (500 mL, 10 vol) at 0-15° C. such that the reaction mixture pH was less than 3. The reaction mixture was maintained at this temperature for 10-15 min and then a 10% sodium bicarbonate solution (300 mL, 6 vol) was added to bring the pH of the solution to greater than 7. After maintaining the reaction mixture at 10-15° C. for about 15 min, the reaction mixture was diluted with MTBE (770 mL, 13.5 vol) and brought to 20-30° C. The organic layer was separated, washed twice with water (100 mL, 2 vol) followed by 10% sodium chloride (200 mL, 4 vol). The organic layer was dried over anhydrous sodium sulfate (12.5 g, 0.25 w/w), filtered and the sodium sulfate was washed with MTBE (100 mL, 2 vol). The filtrate and washings were pooled together and the solvent was distilled below 45° C. under reduced pressure to afford 35 g (88% yield, purity >60% by GC) of crude 4-Br.

The crude 4-Br was dissolved in MTBE, adsorbed onto silica gel and purified by silica gel chromatography using 5-10% ethyl acetate in heptane as the mobile phase. Fractions containing 4-Br were pooled together and the solvent was distilled to afford relatively pure 4-Br. The 4-Br was further purified by slurrying in 5% ethyl acetate in heptane solution (4 vol) at room temperature. The pure 4-Br compound was then dried under reduced pressure below 40° C. to afford 15 g (37% yield, >95%) of 4-Br as a pale brown solid.

$^1$H NMR: δ values with respect to TMS (DMSO-$d_6$; 400 MHz): 8.82 (1H, d, J=1.6 Hz, Ar—H), 8.21 (1H, dd, J=6.8 Hz, 1.6 Hz, Ar—H), 7.50 (1H, d, J=6.8 Hz, Ar—H), 7.43-7.38 (1H, m, Ar—H), 7.27-7.23 (1H, m, Ar—H), 7.11-7.07 (1H, m, Ar—H), 3.39 (1H, d, J=3.6 Hz, —OCH$_A$H$_B$—), 3.14 (1H, d, J=2.0 Hz, —OCH$_A$H$_B$—). $^{13}$C NMR: 163.87-159.78 (dd, 2×Ar—C—), 150.19 (Ar—C), 149.45 (t, Ar—C), 140.14 (Ar—C), 132.80 (Ar—C), 123.18 (Ar—C), 122.50 (Ar—C), 117.41 (t, —CF$_2$—), 116.71 (Ar—C), 111.58 (Ar—C), 104.04 (t, Ar—C), 57.03 (—CO—CH$_2$—), 49.57 (—CH$_2$—O—).

Second Example

A 5 L reactor fitted with a nitrogen inlet/outlet, temperature probe and dropping funnel was charged under nitrogen with potassium tert-butoxide (0.061 kg, 0.54 mol; 1.05 eq.), trimethylsulfoxonium iodide (0.125 kg, 0.566 mol; 1.1 eq.), THF (1.56 L) and dimethylsulfoxide (DMSO) (1.03 L). The mixture was stirred at approximately 20° C. for 1 hr (a solution resulted after ca. 0.25 hr) before being cooled to 0° C. A solution of 3-Br in THF (0.18 kg, 0.515 mol contained in 0.53 kg of solution; GC assay of solution 33.6%) was added over 1 hr at 0-2° C. and stirred at this temperature for a further 1 hr. A sample of the reaction mixture was sampled for GC analysis, which indicated >99.5% conversion of the starting material.

The reaction was quenched by the addition of 1 M hydrochloric acid solution (0.29 L) at 0-5° C., and stirring continued for a further 0.5 hr. Stirring was stopped and the phases allowed to seperate. The lower aqueous layer was extracted with MTBE (0.58 L) and the combined organic phases washed with 10% aqueous sodium thiosulfate solution (0.33 kg), saturated sodium hydrogen carbonate solution (0.58 L), and saturated sodium chloride solution (0.58 L). Gravimetric analysis of the solution indicated a quantitative mass yield of 4-Br. GC (AUC) analysis was 89.1% and HPLC (AUC) was 81.5%. The solvent was evaporated under vacuum at <50° C. and solvent swapped to methanol by the addition of 1.4 kg. Further evaporation under vacuum was carried out at <50° C. to afford a solid residue (0.189 kg) which was used in the next reaction.

Example 4

Preparation of 3-amino-1-(5-bromopyridin-2-yl)-2-(2,4-difluorophenyl)-1,1-difluoropropan-2-ol (±4b-Br)

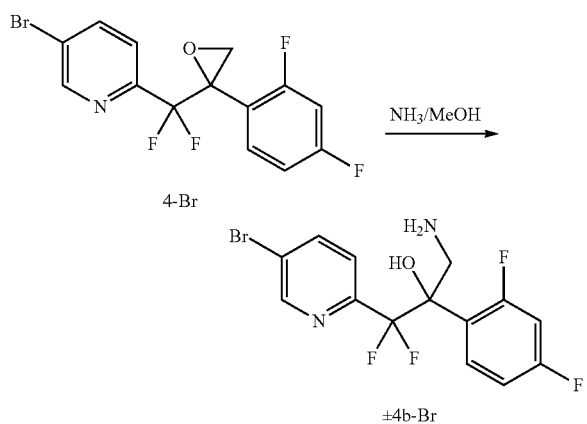

4-Br (200 g, 1 eq) was added into methanolic ammonia (8.0 L; 40 vol; ammonia content: 15-20% w/v) in an autoclave at 10-20° C. The reaction mixture was gradually heated to 60-65° C. and at 3-4 kg/cm² under sealed conditions for 10-12 h. The reaction progress was monitored by GC. After completion of the reaction, the reaction mixture was cooled to 20-30° C. and released the pressure gradually. The solvent was distilled under reduced pressure below 50° C. and the crude obtained was azeotroped with methanol (2×600 mL, 6 vol) followed by with isopropanol (600 mL, 2 vol) to afford 203 g (96.98% yield, purity by HPLC: 94.04%) of ±4b-Br.

Second Example

4-Br solid (0.18 kg, 0.493 mol) and methanol (1.4 kg) were charged to a 5 L reactor equipped with a nitrogen inlet/outlet, temperature probe and condenser. Concentrated ammonia solution (1.62 kg) was added at 20-25° C. and the reaction slowly heated to 45-50° C. (ammonia off-gassing). The reaction mixture gave a solution during the heating period. The solution was heated for a further 18 hr, after which time a sample was submitted for HPLC analysis, which showed conversion of the starting material.

The reaction mixture was concentrated to approximately 5 volumes and MTBE (1.3 L) added. A solution of 20% aqueous potassium carbonate (0.14 kg) was added (pH of solution 11.5-12) and the phases separated. The upper organic layer was washed with saturated sodium chloride solution (0.29 L). Gravimetric analysis of the MTBE solution (1.09 kg) afforded 0.186 kg of a viscous oil containing ±4b-Br. HPLC (AUC) analysis of the oil was 79.5% and HPLC (w/w) assay was 82.3%.

Example 5

Preparation of 3-amino-1-(5-bromopyridin-2-yl)-2-(2,4-difluorophenyl)-1,1-difluoropropan-2-ol (4b-Br or 2c-Br)

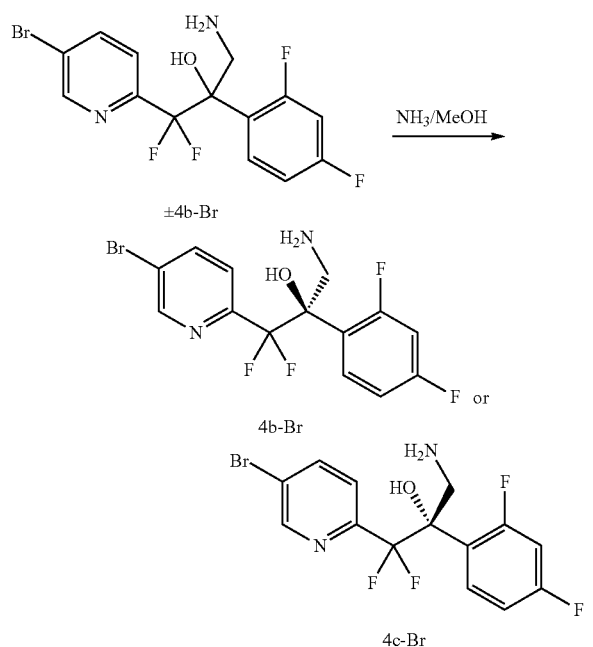

Amino alcohol ±4b-Br (150 g, 1 eq) was dissolved in an isopropanol/acetonitrile mixture (1.5 L, 8:2 ratio, 10 vol) and Di-p-toluoyl-L-tartaric acid (L-DPTTA) (84.05 g, 0.55 eq) was added into the reactor at 20-30° C. The reaction mixture was heated to 45-50° C. for 1-1.5 h (Note: The reaction mixture becomes clear and then became heterogeneous). The reaction mixture was gradually cooled to 20-30° C. and stirred for 16-18 h. The progress of the resolution was monitored by chiral HPLC analysis.

After the completion of the resolution, the reaction mixture was gradually cooled to 20-35° C. The reaction mixture was filtered and the filtered solid was washed with a mixture of acetonitrile and isopropanol (8:2 mixture, 300 mL, 2 vol) and dried to afford 75 g of the L-DPTTA salt (95.37% ee). The L-DPTTA salt obtained was chirally enriched by suspending the salt in methanol/acetonitrile (8:2 mixture; 750 mL, 5 vol) at 45-50° C. for 24-48 h. The chiral enhancement was monitored by chiral HPLC; the solution was gradually cooled to 20-25° C., filtered and washed with an isoporpanol/acetonitrile mixture (8:2 mixture; 1 vol). The purification process was repeated and after filtration, the salt resulted in chiral purity greater than 96% ee. The filtered compound was dried under reduced pressure at 35-40° C. to afford 62 g of the enantio-enriched L-DPPTA salt with 97.12% ee as an off-white solid.

The enantio-enriched L-DPTTA salt (50 g, 1 eq) was dissolved in methanol (150 mL, 3 vol) at 20-30° C. and a potassium carbonate solution (18.05 g $K_2CO_3$ in 150 mL water) was slowly added at 20-30° C. under stirring. The reaction mixture was maintained at this temperature for 2-3 h (pH of the solution at was maintained at 9). Water (600 mL, 12 vol) was added into the reaction mixture through an additional funnel and the reaction mixture was stirred for 2-3 h at 20-30° C. The solids were filtered; washed with water (150 mL, 3 vol) and dried under vacuum at 40-45° C. to afford 26.5 g of amino alcohol 4b-Br or 4c-Br with 99.54% chemical purity, 99.28% ee as an off-white solid. (Water content of the chiral amino alcohol is below 0.10% w/w).

$^1$H NMR: δ values with respect to TMS (DMSO-$d_6$; 400 MHz): 8.68 (1H, d, J=2.0 Hz, Ar—H), 8.16 (1H, dd, J=8.0 Hz, 2.0 Hz, Ar—H), 7.49-7.43 (1H, m, Ar—H), 7.40 (1H, d, J=8 Hz, Ar—H), 7.16-7.11 (1H, m, Ar—H), 7.11-6.99 (1H, m, Ar—H), 3.39-3.36 (1H, m, —OCH$_A$H$_B$—), 3.25-3.22 (1H, m, —OCH$_A$H$_B$—). $^{13}$C NMR: 163.87-158.52 (dd, 2×Ar—C—), 150.88 (Ar—C), 149.16 (Ar—C), 139.21 (Ar—C), 132.39 (Ar—C), 124.49 (Ar—C), 122.17 (Ar—C), 121.87 (d, Ar—C), 119.91 (t, —CF$_2$—), 110.68 (Ar—C), 103.97 (t, Ar—C), 77.41 (t, —C—OH), 44.17 (—CH$_2$—NH$_2$).

Second Example

Di-p-toluoyl-L-tartaric acid (0.069 kg, 0.178 ml; 0.3 eq.) was charged under nitrogen to a 5 L reactor equipped with a nitrogen inlet/outlet. A solution of ±4b-Br in IPA (1.718 kg; contained mass 0.225 kg, 0.59 mol; 1 eq.) was added, followed by acetonitrile (0.35 kg). The reaction mixture was stirred at approximately 20° C. and a solution resulted. The reaction was heated to 50-55° C. (target 52° C.) and stirred at this temperature for 4 hr, during which time a precipitate resulted. An in-process chiral HPLC sample of the reaction was taken by hot filtration of the sample and washing with IPA/acetonitrile (4:1). This indicated a chiral purity of >99%.

The reaction was allowed to cool and stir at 20-25° C. over 16 hr. A second sample was submitted for chiral HPLC analysis, which was 99.5%. The reaction mixture was filtered and washed with a mixture of IPA/acetonitrile (4:1) (0.84 L). The resulting solid was dried under vacuum at 50° C. to give 4b-Br hemi L-DTTA salt (0.113 kg) as a white solid. The mass yield was 33.2%, which is 66.35% of the desired isomer. Chiral HPLC was 99.6%, and achiral HPLC was 99.7%.

Example 6

Preparation of 1-(5-bromopyridin-2-yl)-2-(2,4-difluorophenyl)-1,1-difluoro-3-(1H-tetrazol-1-yl)propan-2-ol (1-6*-Br or 1-7*-Br)

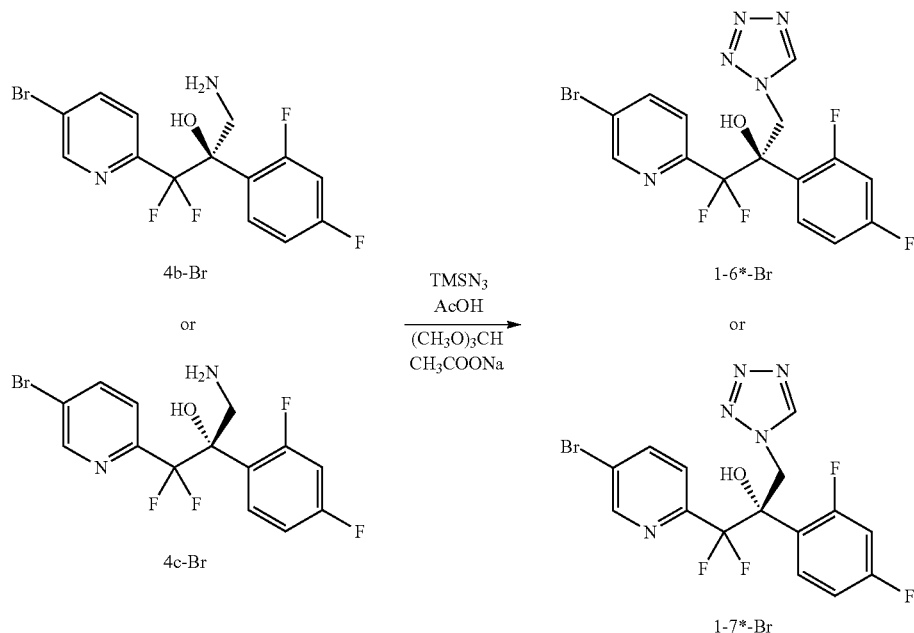 [SMILES: NC[C@](O)(c1ccc(F)cc1F)C(F)(F)c1ccc(Br)cn1 ; O[C@@](Cn1cnnn1)(c1ccc(F)cc1F)C(F)(F)c1ccc(Br)cn1 ; NC[C@@](O)(c1ccc(F)cc1F)C(F)(F)c1ccc(Br)cn1 ; O[C@](Cn1cnnn1)(c1ccc(F)cc1F)C(F)(F)c1ccc(Br)cn1]

4b-Br or 4c-Br (20.0 g, 1 eq.) was added to acetic acid (50 mL, 2.5 vol) at 25-35° C. followed by the addition of anhydrous sodium acetate (4.32 g, 1 eq), trimethyl orthoformate (15.08 g, 2.7 eq). The reaction mixture was stirred for 15-20 min at this temperature and trimethylsilyl azide (12.74 g, 2.1 eq) was added to the reaction mixture (Chilled water was circulated through the condenser to minimize the loss of trimethylsilyl azide from the reaction mixture by evaporation). The reaction mixture was then heated to 70-75° C. and maintained at this temperature for 2-3 h. The reaction progress was monitored by HPLC. Once the reaction was complete, the reaction mixture was cooled to 25-35° C. and water (200 mL, 10 vol) was added. The reaction mixture was extracted with ethyl acetate (400 mL, 20 vol) and the aqueous layer was back extracted with ethyl acetate (100 mL, 5 vol). The combined organic layers were washed with 10% potassium carbonate solution (3×200 mL; 3×10 vol) followed by a 10% NaCl wash (1×200 mL, 10 vol). The organic layer was distilled under reduced pressure below 45° C. The crude obtained was azeotroped with heptanes (3×200 mL) to get 21.5 g (94% yield, 99.26 5 purity) of tetrazole 1-6* or 1-7* compound as pale brown solid (low melting solid).

$^1$H NMR: δ values with respect to TMS (DMSO-$d_6$; 400 MHz NMR instrument): 9.13 (1H, Ar—H), 8.74 (1H, Ar—H), 8.22-8.20 (1H, m, Ar—H), 7.44 (1H, d, J=7.2 Hz, Ar—H), 7.29 (1H—Ar—H), 7.23-7.17 (1H, m, Ar—H), 6.92-6.88 (1H, Ar—H), 5.61 (1H, d, J=11.2 Hz, —OCH$_A$H$_B$—), 5.08 (1H, d, J=5.6 Hz, —OCH$_A$H$_B$—). $^{13}$C NMR: 163.67-161.59 (dd, Ar—C—), 160.60-158.50 (dd, Ar—C—), 149.65 (Ar—C), 144.99 (Ar—C), 139.75 (Ar—C), 131.65 (Ar—C), 124.26 (Ar—C), 122.32 (d, Ar—C), 119.16 (t, —CF$_2$—), 118.70 (d, Ar—C), 111.05 (d, Ar—C) 104.29 (t, Ar—C), 76.79 (t, —C—OH), 59.72 (Ar—C), 50.23 (—OCH$_2$N—).

Example 7

Preparation of 2-(2,4-difluorophenyl)-1,1-difluoro-3-(1H-tetrazol-1-yl)-1-(5-(4-(2,2,2-trifluoroethoxy)phenyl)pyridin-2-yl)propan-2-ol (1 or 1a)

A. Preparation of 1 or 1a Via 1-6*-Br or 1-7*-Br

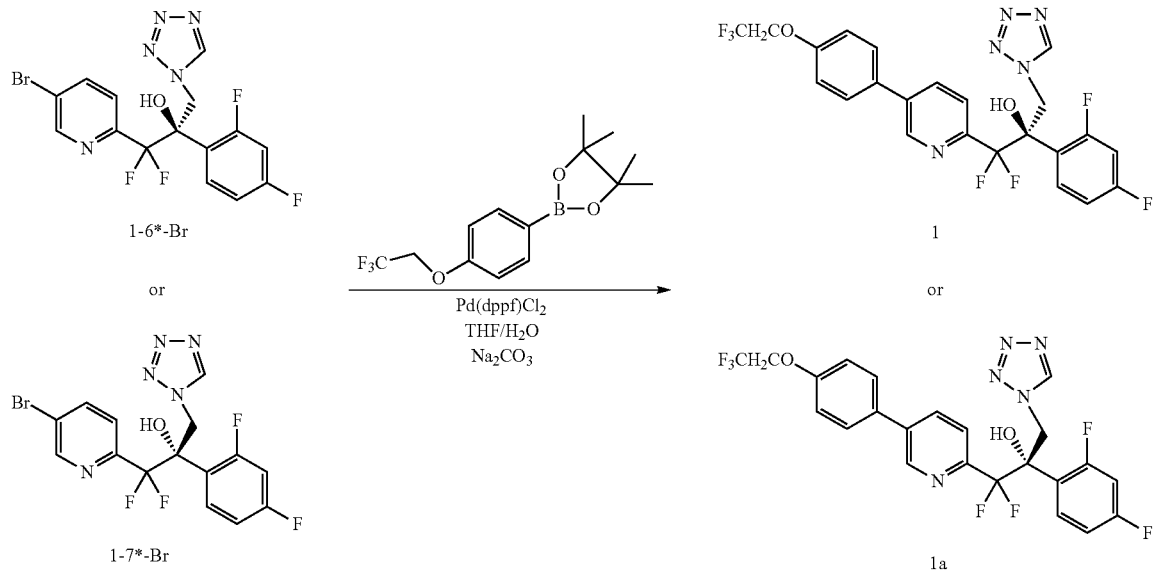

Synthesis of 4,4,5,5-tetramethyl-2-(4-(2,2,2-trifluoroethoxy)phenyl)-1,3,2-dioxaborolane Potassium carbonate (59.7 g, 2.2 eq.) was added to a slurry of DMF (190 mL, 3.8 Vol.), 4-Bromo phenol (37.4 g, 1.1 eq.) and 2,2,2-trifluoroethyl tosylate (50.0 g, 1.0 eq.) at 20-35° C. under an inert atmosphere. The reaction mixture was heated to 115-120° C. and maintained at this temperature for 15-18 h. The reaction progress was monitored by GC. The reaction mixture was then cooled to 20-35° C., toluene (200 mL, 4.0 vol.) and water (365 mL, 7.3 vol.) were added at the same temperature, stirred for 10-15 minutes and separated the layers. The aqueous layer was extracted with toluene (200 mL, 4.0 vol.). The organic layers were combined and washed with a 2M sodium hydroxide solution (175 mL, 3.5 vol.) followed by a 20% sodium chloride solution (175 mL, 3.5 vol.). The organic layer was then dried over anhydrous sodium sulfate and filtered. The toluene layer was transferred into clean reactor, spurged with argon gas for not less than 1 h. Bis(Pinacolato) diborane (47 g, 1.1 eq.), potassium acetate (49.6 g, 3.0 eq.) and 1,4-dioxane (430 mL, 10 vol.) were added at 20-35° C., and spurged the reaction mixture with argon gas for at least 1 h. Pd(dppf)Cl$_2$ (6.88 g, 0.05 eq) was added to the reaction mixture and continued the argon spurging for 10-15 minutes. The reaction mixture temperature was increased to 70-75° C., maintained the temperature under argon atmosphere for 15-35 h and monitored the reaction progress by GC. The reaction mixture was cooled to 20-35° C., filtered the reaction mixture through a Celite pad, and washed with ethyl acetate (86 mL, 2 vol.). The filtrate was washed with water (430 mL, 10 vol.). The aqueous layer was extracted with ethyl acetate (258 mL, 6 vol.) and washed the combined organic layers with a 10% sodium chloride solution (215 mL, 5 vol.). The organic layer was dried over anhydrous sodium sulfate (43 g, 1 time w/w), filtered and concentrated under reduced pressure below 45° C. to afford crude 4,4,5,5-tetramethyl-2-(4-(2,2,2-trifluoroethoxy)phenyl)-1,3,2-dioxaborolane (65 g; 71% yield with the purity of 85.18% by GC). The crude 4,4,5,5-tetramethyl-2-(4-(2,2,2-trifluoroethoxy)phenyl)-1,3,2-dioxaborolane (65 g, 1 eq.) was dissolved in 10% ethyl acetate-n-Heptane (455 mL, 7 vol.) and stirred for 30-50 minutes at 20-35° C. The solution was filtered through a Celite bed and washed with 10% ethyl acetate in n-Heptane (195 mL, 3 vol.). The filtrate and washings were pooled together, concentrated under vacuum below 45° C. to afford 4,4,5,5-tetramethyl-2-(4-(2,2,2-trifluoroethoxy)phenyl)-1,3,2-dioxaborolane as a thick syrup (45.5 g; 70% recovery). This was then dissolved in 3% ethyl acetate-n-heptane (4 vol.) and adsorbed on 100-200 M silica gel (2 times), eluted through silica (4 times) using 3% ethyl acetate-n-heptane. The product rich fractions were pooled together and concentrated under vacuum. The column purified fractions (>85% pure) were transferred into a round bottom flask equipped with a distillation set-up. The compound was distilled under high vacuum below 180° C. and collected into multiple fractions. The purity of fractions was analyzed by GC (should be >98% with single max impurity <1.0%). The less pure fractions (>85% and <98% pure fraction) were pooled together and the distillation was repeated to get 19 g (32% yield) of 4,4,5,5-tetramethyl-2-(4-(2,2,2-trifluoroethoxy)phenyl)-1,3,2-dioxaborolane as a pale yellow liquid.

$^1$H NMR: δ values with respect to TMS (DMSO-d$^6$; 400 MHz): 7.64 (2H, d, 6.8 Hz), 7.06 (2H, d, J=6.4 Hz), 4.79 (2H, q, J=6.8 Hz), 1.28 (12H, s).

$^{13}$C NMR: 159.46 (Ar—C—O—), 136.24 (2×Ar—C—), 127.77-120.9 (q, —CF$_3$), 122.0 (Ar—C—B), 114.22 (2×Ar—C—), 64.75 (q, J=27.5 Hz).

Synthesis of 2-(2,4-difluorophenyl)-1,1-difluoro-3-(1H-tetrazol-1-yl)-1-(5-(4-(2,2,2-trifluoroethoxy)phenyl)pyridin-2-yl)propan-2-ol (1 or 1a)

1-6*-Br or 1-7*-Br (14 g, 0.03 mol, 1 eq) was added to tetrahydrofuran (168 mL, 12 vol) at 25-35° C. and the resulting solution was heated to 40-45° C. The reaction mixture was maintained at this temperature for 20-30 min under argon bubbling. Sodium carbonate (8.59 g, 0.08 mol, 2.5 eq) and water (21 mL, 1.5 vol) were added into the reaction mixture and the bubbling of argon was continued for another 20-30 min. 4,4,5,5-tetramethyl-2-(4-(2,2,2-trifluoroethoxy)phenyl)-1,3,2-dioxaborolane (10.76 g, 1.1 eq) dissolved in tetrahydrofuran (42 mL, 3 vol) was added into the reaction mixture and argon bubbling was continued for 20-30 min. Pd(dppf)Cl$_2$ (2.65 g, 0.1 eq) was added to the reaction mixture under argon bubbling and stirred for 20-30 min (Reaction mixture turned into dark red color). The reaction mixture was heated to 65-70° C. and maintained at this temperature for 3-4 h. The reaction progress was monitored by HPLC. The reaction mixture was cooled to 40-45° C. and the solvent was distilled under reduced pressure. Toluene (350 mL, 25 vol.) was added to the reaction mixture and stirred for 10-15 min followed by the addition of water (140 mL, 10 vol). The reaction mixture was filtered through Hyflo (42 g, 3 times), the layers were separated and the organic layer was washed with water (70 mL, 5 vol) and a 20% w/w sodium chloride solution (140 mL, 10 vol). The organic layer was treated with charcoal (5.6 g, 0.4 times, neutral chalrcoal), filtered through Hyflo. (1S)-10-Camphor sulfonic acid (7.2 g, 1 eq.) was added to the toluene layer and the resulting mixture was heated to 70-75° C. for 2-3 h. The reaction mixture was gradually cooled to 25-35° C. and stirred for 1-2 h. The solids were filtered, washed with toluene (2×5 vol.) and then dried under vacuum below 45° C. to afford 18.0 g of an off white solid. The solids (13.5 g, 1 eq.) were suspended in toluene (135 mL, 10 vol) and neutralized by adding 1M NaOH solution (1.48 vol, 1.1 eq) at 25-35° C. and stirred for 20-30 min. Water (67.5 mL, 5 vol) was added to the reaction mixture and stirred for 10-15 min, and then the layers were separated. The organic layer was washed with water (67.5 mL, 5 vol) to remove the traces of CSA. The toluene was removed under reduced pressure below 45° C. to afford crude 1 or 1a. Traces of toluene were removed by azeotroping with ethanol (3×10 vol), after which light brown solid of crude 1 or 1a (7.5 g, 80% yield) was obtained.

The crude 1 or 1a (5 g) was dissolved in ethanol (90 mL, 18 vol.) at 20-35° C., and heated to 40-45° C. Water (14 vol) was added to the solution at 40-45° C., the solution was maintained at this temperature for 30-45 min and then gradually cooled to 20-35° C. The resulting suspension was continued to stir for 16-18 h at 20-35° C., an additional amount of water (4 vol.) was added and the stirring continued for 3-4 h. The solids were filtered to afford 4.0 g (80% recovery) of 1 or 1a (HPLC purity >98%) as an off-white solid.

$^1$H NMR: δ values with respect to TMS (DMSO-d$_6$; 400 MHz): 9.15 (1H, s, Ar—H), 8.93 (1H, d, J=0.8 Hz, Ar—H), 0.8.22-8.20 (1H, m, Ar—H), 7.80 (2H, d, J=6.8 Hz, Ar—H), 7.52 (1H, d, J=6.8 Hz, Ar—H), 7.29 (1H, d, J=3.2 Hz, Ar—H), 7.27-7.21 (1H, m, Ar—H), 7.23-7.21 (2H, d, J=6.8 Hz, Ar—H), 7.19 (1H, d, J=6.8 Hz, Ar—H), 6.93-6.89 (1H, m, Ar—H), 5.68 (1H, J=12 Hz, —CH$_A$H$_B$), 5.12 (2H, d, J=11.6 Hz, —CH$_A$H$_B$), 4.85 (2H, q, J=7.6 Hz).

$^{13}$C NMR: 163.93-158.33 (m, 2×Ar—C), 157.56 (Ar—C), 149.32 (t, Ar—C), 146.40 (Ar—C), 145.02 (Ar—C), 136.20 (Ar—C), 134.26 (2×Ar—C), 131.88-131.74 (m, AR—C), 129.72 (Ar—C), 128.47 (2×Ar—C), 123.97 (q, —CF$_2$—), 122.41 (Ar—C), 119.30 (—CF$_3$), 118.99 (Ar—C), 115.65 (2×Ar—C), 110.99 (d, Ar—C), 104.22 (t, Ar—C), 77.41-76.80 (m, Ar—C), 64.72 (q, —OCH$_2$—CF$_3$), 50.54 (—CH$_2$—N—).

B. Preparation of 1 or 1a Via 4b-Br or 4c-Br

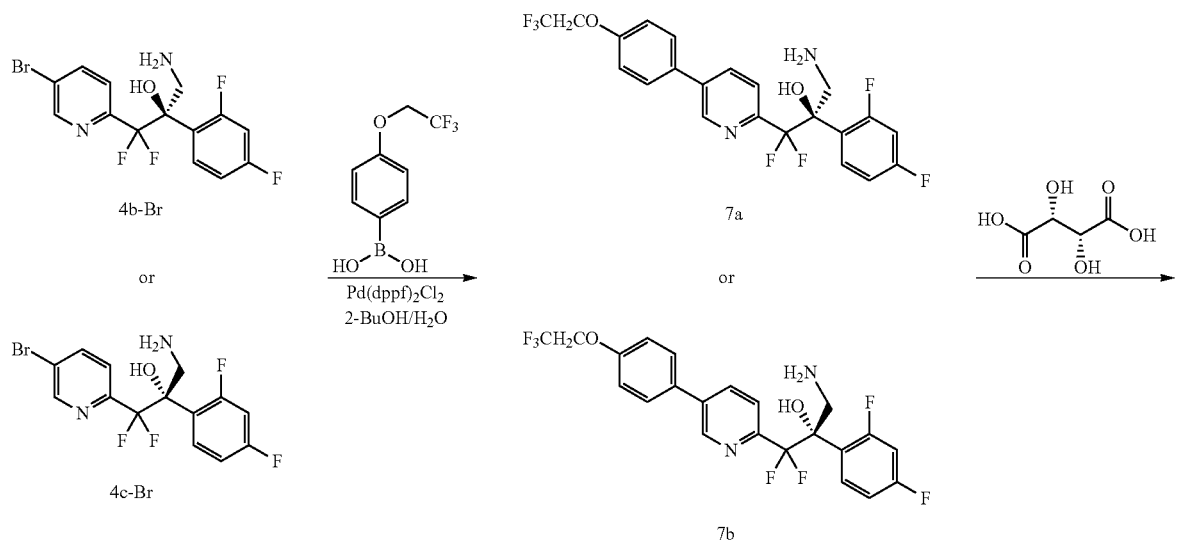

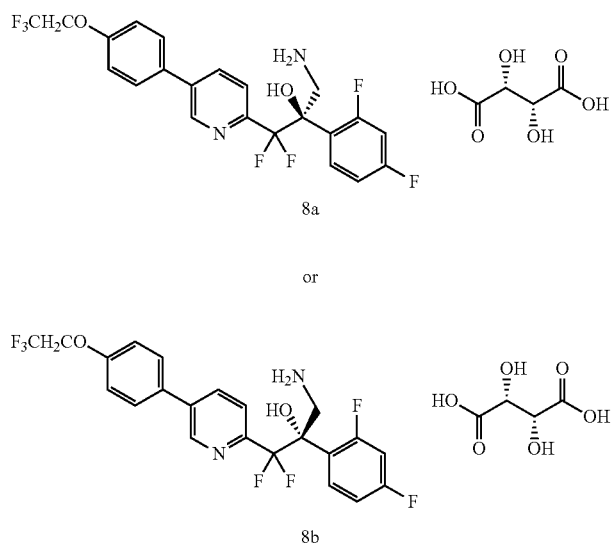

8a or

8b

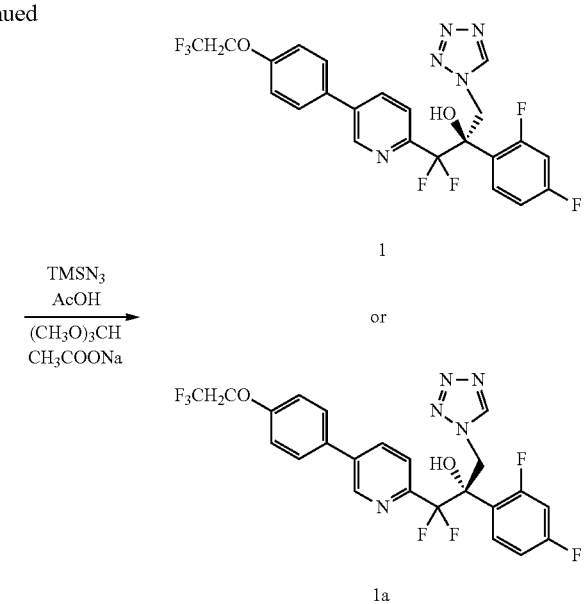

1 or

1a

TMSN₃
AcOH
(CH₃O)₃CH
CH₃COONa

Synthesis of 3-amino-2-(2,4-difluorophenyl)-1,1-difluoro-1-(5-(4-(2,2,2-trifluoroethoxy)phenyl)pyridin-2-yl)propan-2-ol (8a or 8b)

Potassium carbonate (30.4 g) and water (53.3 g) were charged to a 1-L flask equipped with overhead stirring, thermocouple, and nitrogen/vacuum inlet valve, and stirred until dissolved. The boronic acid (19.37 g), a solution of 4b-Br or 4c-Br in 2-butanol (103.5 g, 27.8 g theoretical 4b-Br or 4c-Br)) and 2-BuOH (147.1 g) were added and stirred to form a clear mixture. The flask was evacuated and refilled with nitrogen 3 times. Pd(dppf)$_2$Cl$_2$ (0.30 g) was added and stirred to form a light orange solution. The flask was evacuated and refilled with nitrogen 4 times. The mixture was heated to 85° C. and stirred overnight and endpointed by HPLC analysis. The reaction mixture was cooled to 60° C. and the layers were allowed to settle. The aqueous layer was separated. The organic layer was washed with 5% NaCl solution (5×100 ml) at 30-40° C. The organic layer was filtered and transferred to a clean flask with rinses of 2-BuOH. The combined solution was 309.7 g, water content 13.6 wt % by KF analysis. The solution was diluted with 2-BuOH (189 g) and water (10 g). Theoretically the solution contained 34.8 g product, 522 ml (15 volumes) of 2-BuOH, and 52.2 ml (1.5 volumes) of water. L-Tartaric acid (13.25 g) was added and the mixture was heated to a target temperature of 70-75° C. During the heat-up, a thick suspension formed. After about 15 minutes at 70-72° C. the suspension became fluid and easily stirred. The suspension was cooled at a rate of 10° C./hour to 25° C. then stirred at 25° C. for about 10 hours. The product was collected on a vacuum filter and washed with 10:1 (v/v) 2-BuOH/water (50 ml) and 2-butanol (40 ml). The salt was dried in a vacuum oven at 60° C. with a nitrogen purge for 2 days. The yield was 40.08 g of 8a or 8b as a fluffy, grayish-white solid. The water content was 0.13 wt % by KF analysis. The yield was 87.3% with an HPLC purity of 99.48%.

Synthesis of 2-(2,4-difluorophenyl)-1,1-difluoro-3-(1H-tetrazol-1-yl)-1-(5-(4-(2,2,2-trifluoroethoxy)phenyl)pyridin-2-yl)propan-2-ol (1 or 1a)

To a 350 ml pressure bottle were charged acetic acid (73 ml), 8a or 8b (34.8 g), sodium acetate (4.58 g) and trimethylorthoformate (16.0 g). The mixture was stirred for 18 min. at room temperature until a uniform suspension was obtained. Azidotrimethylsilane (8.88 g) was added and the bottle was sealed. The bottle was immersed in an oil bath and magnetically stirred. The oil bath was at 52° C. initially, and was warmed to 62-64° C. over about ½ hour. The suspension was stirred at 62-64° C. overnight. After 20.5 hours the suspension was cooled to room temperature and sampled. The reaction was complete by HPLC analysis. The reaction was combined with three other reactions that used the same raw material lots and general procedure (total of 3.0 g additional starting material). The combined reactions were diluted with ethyl acetate (370 ml) and water (368 ml) and stirred for about ½ hour at room temperature. The layers were settled and separated. The organic layer was washed with 10% K$_2$CO$_3$ solution (370 ml/397 g) and 20% NaCl solution (370 ml/424 g). The organic layer (319 g) was concentrated, diluted with ethanol (202 g) and filtered, rinsed with ethanol (83 g). The combined filtrate was concentrated to 74 g of amber solution.

The crude 1 or 1a solution in ethanol (74 g solution, containing theoretically 31.9 g 1 or 1a) was transferred to a 2-L flask equipped with overhead stirring, thermocouple, and addition funnel. Ethanol (335 g) was added including that used to complete the transfer of the 1 or 1a solution. The solution was heated to nominally 50° C. and water (392 g) was added over 12 minutes. The resulting hazy solution was seeded with 1 or 1a crystals and stirred at 50° C. After about ½ hour the mixture was allowed to cool to 40° C. over about ½ hour during which time crystallization started. Some darker colored chunky solid separated out from the main suspension. The pH of the crystallizing mixture was adjusted from 4.5 to 6 using 41% KOH (1.7 g). After about 1 hour a good suspension had formed. Additional water (191 g) was added slowly over ½ hour. The suspension was heated to 50° C. and cooled at 5° C./min to room temperature. After stirring overnight the suspension was cooled in a water bath to 16° C. and filtered after 1 hour. The wet cake was washed with 55:45 (v/v) water/ethanol (2×50 ml) and air-dried on the vacuum filter funnel overnight. Further drying at 40° C. in a vacuum oven with a nitrogen bleed resulted in no additional weight loss. The yield was 30.2 g of off-white fine powder plus some darker granular material. By in-process HPLC analysis there was no difference in the chemical purity of the darker and lighter materials. The purity was 99.4%. The water content was 2.16 wt % by KF analysis. The residual ethanol was 1.7 wt % estimated by $^1$H NMR analysis. The corrected yield was 29.0 g, 91.0% overall yield for tetrazole formation and crystallization. The melting point was 65° C. by DSC analysis.

C. Alternate Preparation of 1 or 1a Via 4b-Br or 4c-Br

A 5 L reactor equipped with a nitrogen inlet/outlet was charged under nitrogen with 4b-Br hemi L-DTTA salt (0.145 kg, 0.253 mol) and MTBE (0.725 L). The suspension was stirred and a solution of potassium carbonate (0.105 kg, 0.759 mol; 3 eq.) in water (0.945 kg) added. The reaction was stirred for 0.25 hr during which time a solution resulted. Stirring was stopped and the phases allowed to separate. The lower aqueous layer (pH 10) was removed and extracted with MTBE (0.725 L). The combined organic layers were evaporated under vacuum at <50° C. to give an oil (0.105 kg). 2-Butanol (0.276 kg) was added and distilled to remove residual MTBE. 2-Butanol (0.39 kg) was added. The weight of the 4b-Br (−) solution (0.502 kg) was assumed to contain theoretical free base (0.096 kg) and 2-butanol (0.406 kg).

A solution of potassium carbonate (0.104 kg, 0.759 mol; 3 eq.) in water (0.184 kg) was prepared and charged to the reactor together with 4-(trifluoroethoxy)phenyl boronic acid (0.067 kg. 0.304 mol; 1.2 eq.) The 4b-Br (−) solution in 2-butanol was added, followed by a further charge of 2-butanol (0.364 kg). The clear solution was sparged with nitrogen for 0.5 hr before adding the Pd(dppf)C12 catalyst (1.03 g, 0.5 mol %) and continuing the nitrogen sparge for a further 0.5 hr. The reaction was heated to 85° C. and maintained for 18 hr, after which time the HPLC IPC analysis indicated consumption of the starting material.

The reaction mixture was cooled to 60° C. and the lower aqueous phase separated (salts precipitate at low temperatures). The organic phase was washed with 5% sodium chloride solution (5×0.334 kg) at 30-40° C., with a small interface layer removed with the final aqueous wash. The organic phase was filtered through a glass fibre filter and washed through with 2-butanol (0.065 L). The total solution weight (0.921 kg) was 15.7% by KF analysis (0.145 kg contained), with assumed theoretical Suzuki free base 7a (0.120 kg) and 2-butanol (0.656 kg). Further 2-butanol (0.793 kg) and water (0.036 kg) were added. The theoretical reaction composition was 0.120 kg of product, 15 volumes of 2-butanol and 1.5 volumes of water.

L-Tartaric acid (0.046 kg, 0.304 mol; 1.2 eq.) was added and the reaction was heated to 70-75° C. During the heating period the suspension thickened, but thinned out when at temperature. Heating was maintained for 1 hr before being cooled to 20-25° C. at approximately 10° C./h and stirred for approximately 16 hr. The product was isolated by filtration and washed with 10:1 (v/v) 2-butanol/water (0.17 L) and 2-butanol (0.14 L). The solid was dried under vacuum at 60° C. to give 8a tartrate (0.132 kg, 83%) as an off-white/grey solid. The water content was 2.75% by KF analysis, and HPLC was 99.5%.

A 1 L reactor equipped with condenser, temperature probe and a nitrogen inlet/outlet was charged under nitrogen with 8a tartrate (0.13 kg, 0.208 mol), sodium acetate (0.017 kg, 0.208 mol) and acetic acid (0.273 L). Trimethyl orthoformate (0.132 kg, 1.248 mol; 6 eq.) was added and the suspension stirred at 20-25° C. for 1.25 hr. Azidotrimethylsilane (0.033 kg, 0.287 mol; 1.4 eq.) was added and the suspension heated to 60-65° C. and maintained at this temperature for 16 hr. A sample submitted for HPLC IPC analysis indicated 0.2% of the starting material and 2.9% of the formamide impurity.

The reaction mixture was cooled to 20-25° C. and charged to a 5 L reactor with ethyl acetate (1.38 L) and purified water (1.38 L). The two phase solution was stirred for 0.5 h and the aqueous phase (pH 4-5) was removed. A small interphase layer was retained with the organics. The organic phase was washed with 10% aqueous potassium carbonate solution (2.2 kg) and separated (aqueous pH 9.3). The organic phase was washed with 20% sodium chloride solution (1.625 kg) and a small interphase layer was removed with the aqueous.

The organic phase was charged to a 2 L reactor under nitrogen with SiliaMetS Thiol palladium scavenger (9.2 g). The reaction heated to 50-55° C. and maintained at this temperature for 16 hr before being cooled to 20-25° C. The scavenger was removed by filtration through a 0.7 micron filter and washed with ethyl acetate, and the filtrate/wash evaporated under vacuum at <50° C. to 100 mL. Ethanol (100%, 755 g) was added and the solution further evaporated to 377 g (ca. 440 mL). The solution (theoretical composition 109 g 1 and 267 g ethanol) was diluted with further ethanol (1.031 kg) and transferred to a 5 L reactor). The solution was heated to 50° C. and purified water (1.34 kg) was added at 45-50° C. over 0.25 hr to give a hazy solution. This was stirred for 0.5 hr and adjusted to pH 6 with 40% potassium carbonate solution (one drop). Stirring was continued for a further 1 hr at 40-42° C. and a second addition of purified water (0.65 kg) added at this temperature over 0.5 hr. The temperature was increased to 50° C. and maintained for 0.5 hr before cooling at 10° C./hr to 20° C. The solid was isolated by filtration and washed with ethanol/water (45:55) (2×0.17 L) and dried under vacuum at 45-50° C. to give 1 X-hydrate (0.0937 kg, 85.3%) as an off-white solid. HPLC (AUC) analysis was 99.62%, with 0.27% formamide and 0.11% RRT 0.98.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A process to prepare compound 1 or 1a, salts thereof, or a mixture thereof:

1

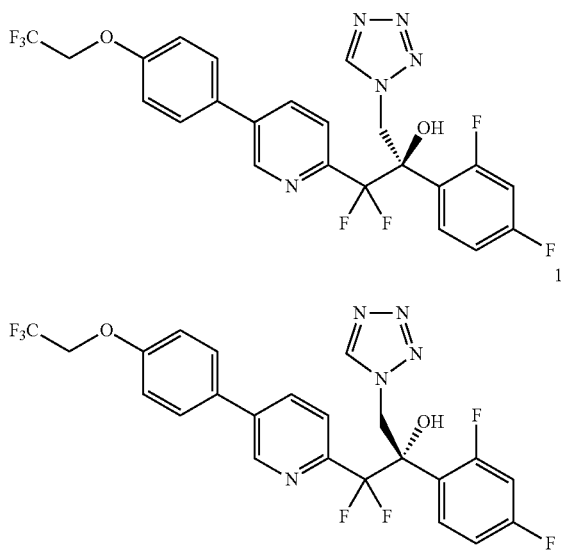

1a comprising performing a chemical reaction with morpholine amide 2b:

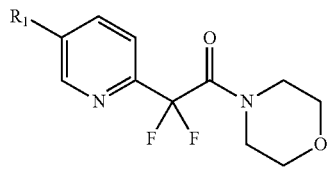

as a reactant, wherein the reaction results in a product compound 1 or 1a, or mixtures thereof;
wherein $R_1$ is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

2. The process of claim 1, comprising reacting morpholine amide 2b:

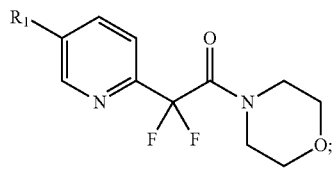

with

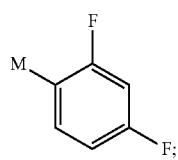

wherein M is Mg or MgX, Li, AlX$_2$; and X is halogen, alkyl, or aryl;
wherein the reaction results in a product compound 1 or 1a, or a mixture thereof:

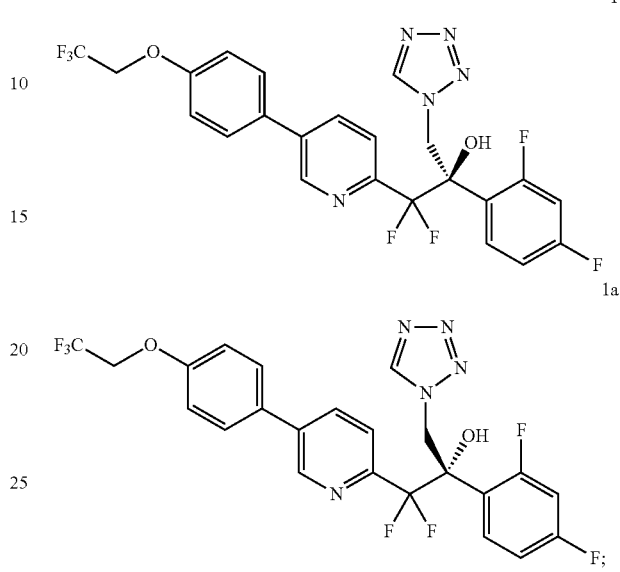

wherein $R_1$ is halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

3. The process of claim 2, wherein M is Mg or MgX, and X is halogen.

4. The process of claim 1, further comprising performing a reaction to form an amidation product of ester 2:

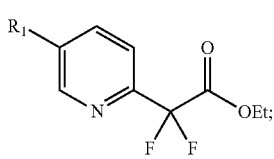

wherein the reaction results in product morpholine amide 2b:

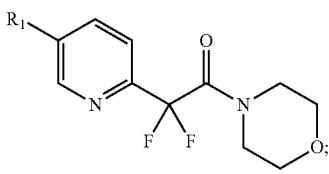

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

5. The process of claim 4, comprising reacting ester 2:

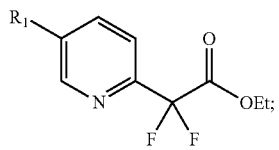

with morpholine, wherein the reaction results in a product morpholine amide 2b:

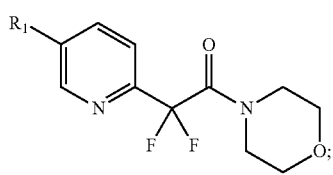

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

6. The process of claim 1, further comprising:
(i) performing a reaction to displace the morpholino portion of morpholine amide 2b,

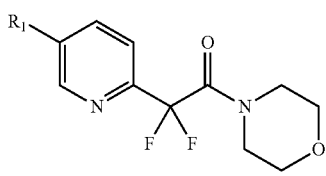

to
wherein the reaction of (i) results in a product ketone 3,

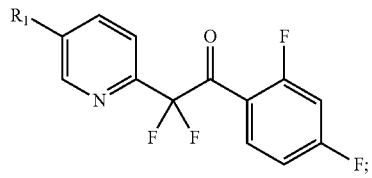

(ii) performing a reaction to arylate ketone 3,

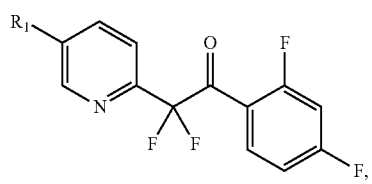

to wherein the reaction of (ii) results in a product aryl-pyridine 1-4,

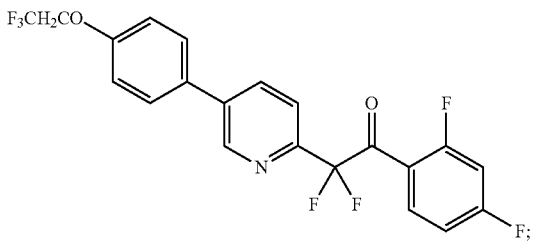

(iii) performing a reaction to form an epoxide of aryl-pyridine 1-4,

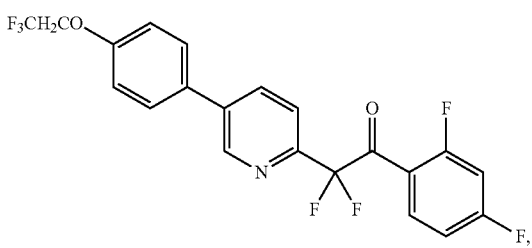

wherein the reaction of (iii) results in a product epoxide 5,

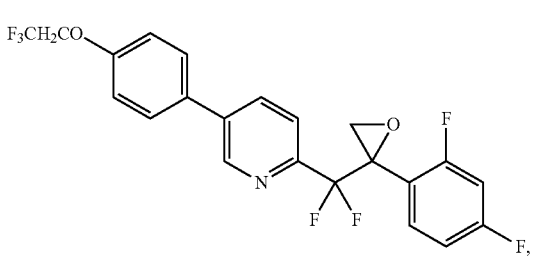

(iv) performing a ring-opening reaction to open the ring of epoxide 5, wherein the reaction of (iv) results in a product amino-alcohol ±1-6,

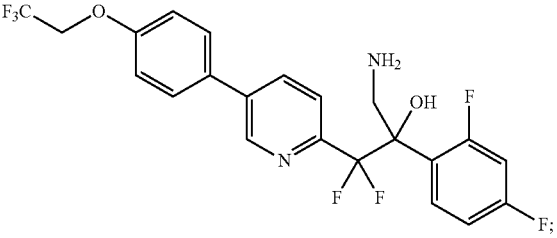 [SMILES: NCC(O)(c1ccc(F)cc1F)C(F)(F)c1ccc(-c2ccc(OCC(F)(F)F)cc2)cn1]

(v) enriching the enantiomeric purity of amino-alcohol ±1-6,

101

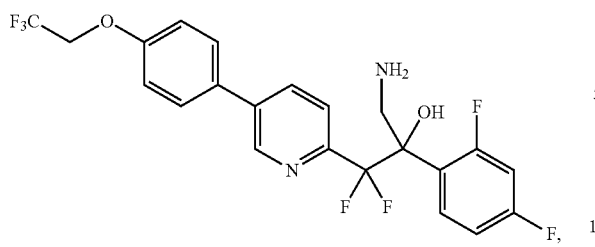

wherein the enrichment of (v) results in an enantio-enriched amino-alcohol 1-6* or 1-7*,

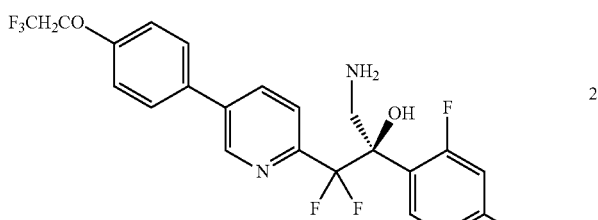 or

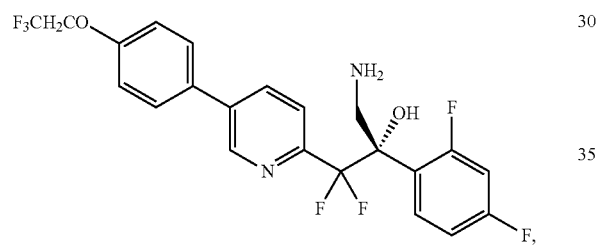

or a mixture thereof; and (vi) performing a reaction to form the tetrazole of enantio-enriched amino-alcohol 1-6* or 1-7*,

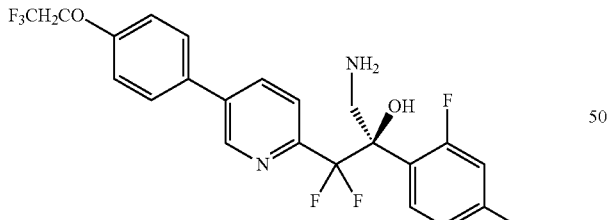 or

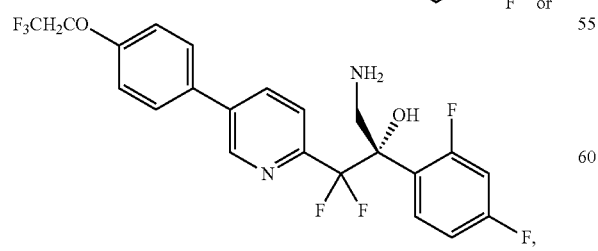

or a mixture thereof, wherein the reaction of (vi) results in a product compound 1 or 1a,

102

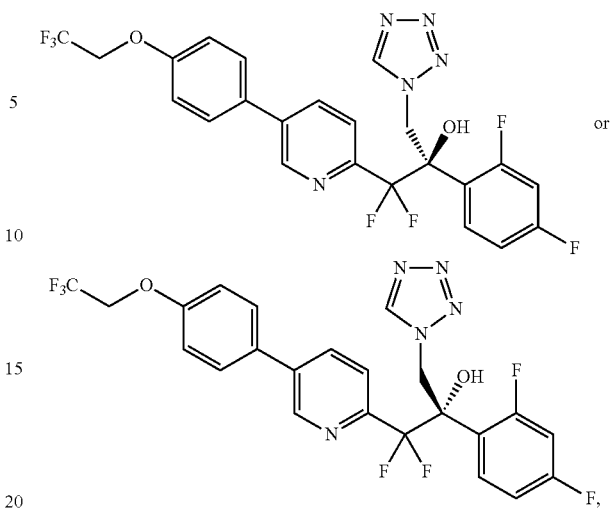

or a mixture thereof;

wherein each $R_1$ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO$_2$)-alkyl, —O(SO$_2$)-substituted alkyl, —O(SO$_2$)-aryl, or —O(SO$_2$)-substituted aryl.

7. The process of claim 1, further comprising:

(i) performing a reaction to displace the morpholino portion of morpholine amide 2b,

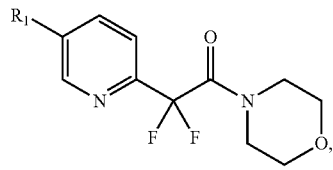

wherein the reaction of (i) results in a product ketone 3, (ii) performing a reaction to form an epoxide of ketone 3,

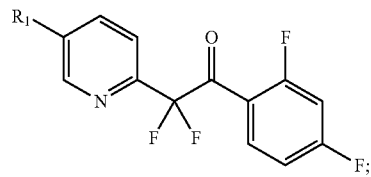

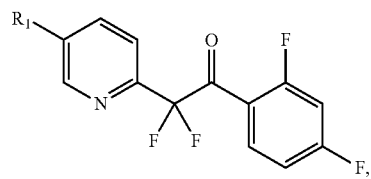

wherein the reaction of (ii) results in a product epoxide 4,

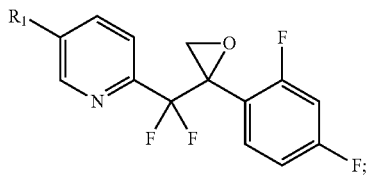

(iii) performing a ring-opening reaction to open the ring of epoxide

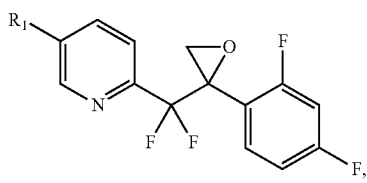

wherein the reaction of (iii) results in a product amino-alcohol ±4b,

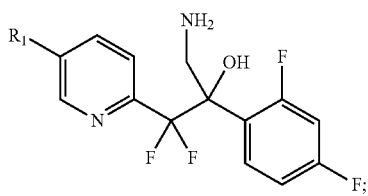

(iv) enriching the enantiomeric purity of amino-alcohol ±4b,

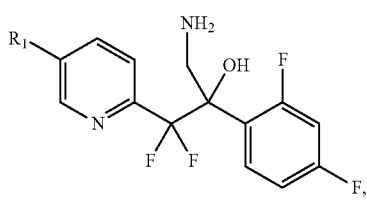

wherein the enrichment of (iv) results in an enantio-enriched amino-alcohol 4b or 4c:

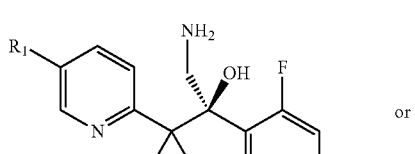

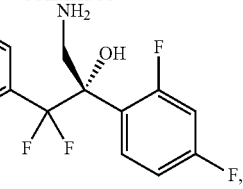

or a mixture thereof;

(v) performing a reaction to form the tetrazole of enantio-enriched amino-alcohol 4b or 4c:

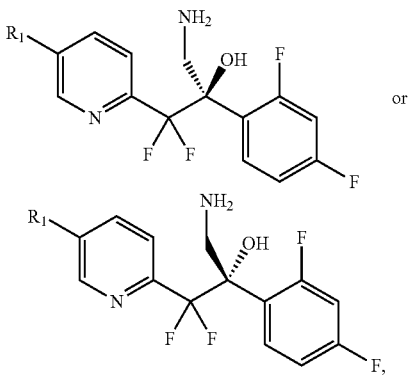

or a mixture thereof, wherein the reaction of (v) results in a product tetrazole 6 or 6a,

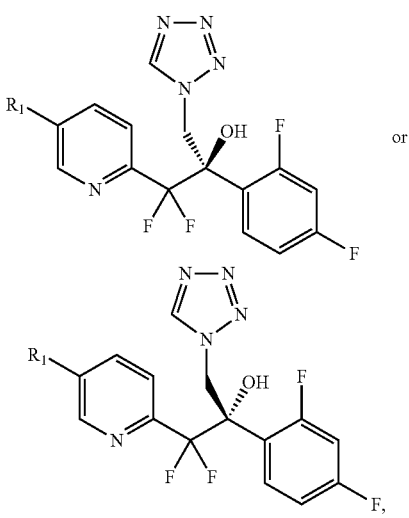

or a mixture thereof; and (vi) performing a reaction to arylate tetrazole 6 or 6a,

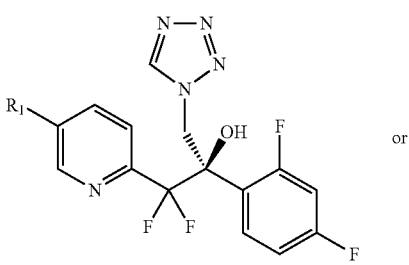

-continued

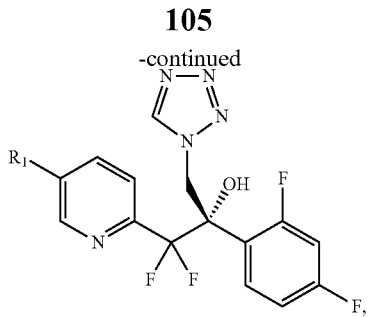

or a mixture thereof, wherein the reaction of (vi) results in a product compound 1 or 1a,

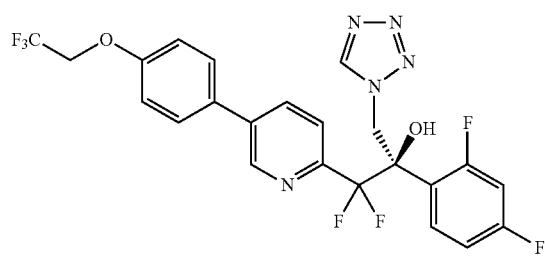

or

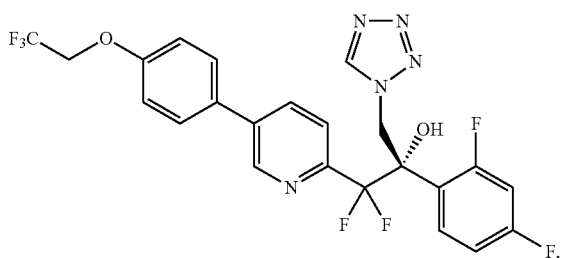

or a mixture thereof;

wherein each R₁ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

8. The process of claim 7, further comprising:

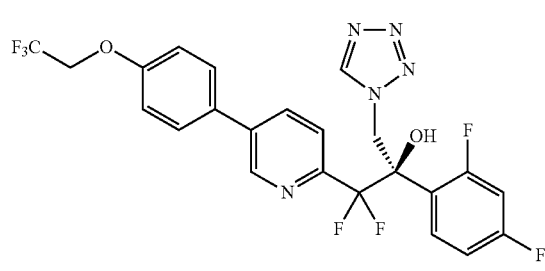

or

-continued

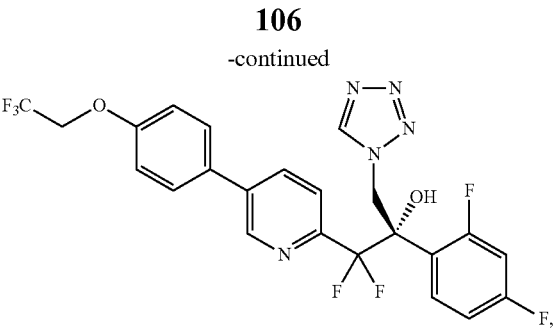

(i) combining compound 1 or 1a, or a mixture thereof, a sulfonic acid

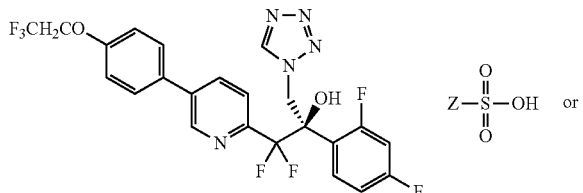

and a crystallization solvent or crystallization solvent mixture;

(ii) diluting the mixture from step (i) with a crystallization co-solvent or crystallization co-solvent mixture; and (iii) isolating a compound of formula IX or IXa,

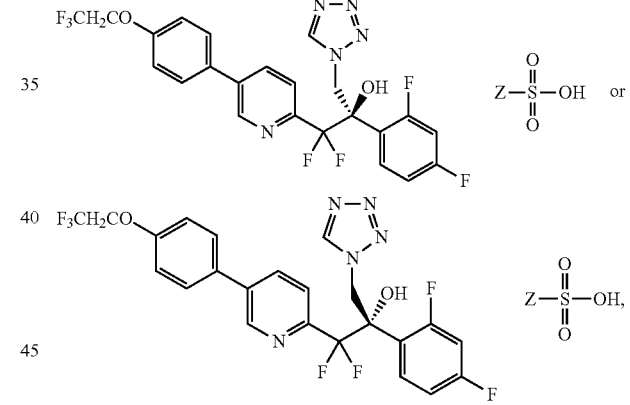

or a mixture thereof;

wherein each Z is independently aryl, substituted aryl, alkyl, or substituted alkyl.

9. The process of claim 8, wherein Z is phenyl, p-tolyl, methyl, or ethyl.

10. The process of claim 8, wherein the crystallization solvent or crystallization solvent mixture is ethyl acetate, isopropyl acetate, ethanol, methanol, or acetonitrile, or combinations thereof.

11. The process of claim 8, wherein the crystallization co-solvent or crystallization co-solvent mixture is pentane, methyl tert-butylether, hexane, heptane, or toluene, or combinations thereof.

12. The process of claim 1, further comprising:

(i) performing a reaction to displace the ester portion of ester 2,

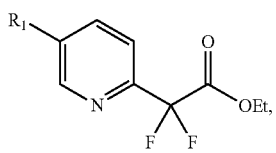

wherein the reaction of (i) results in a product morpholine amide 2b,

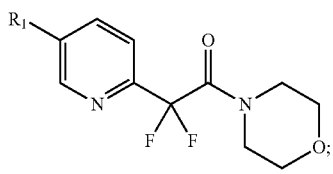

(ii) performing a reaction to displace the morpholino portion of morpholine amide 2b,

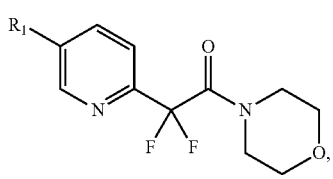

wherein the reaction of (ii) results in a product ketone 3,

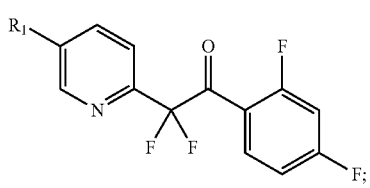

(iii) performing a reaction to form an epoxide of ketone 3,

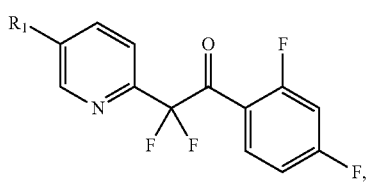

wherein the reaction of (iii) results in a product epoxide 4,

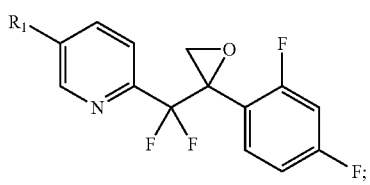

(iv) performing a ring-opening reaction to open the ring of epoxide 4,

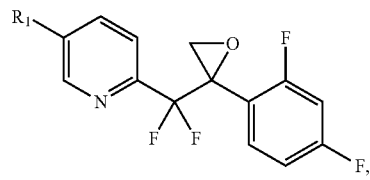

wherein the reaction of (iv) results in amino-alcohol ±4b,

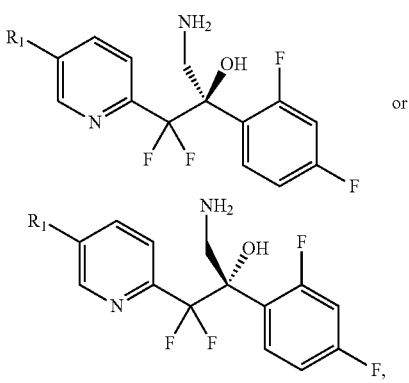

(v) enriching the enantiomeric purity of amino-alcohol ±4b, wherein the enrichment of (v) results in an enantio-enriched amino-alcohol 4b or 4c:

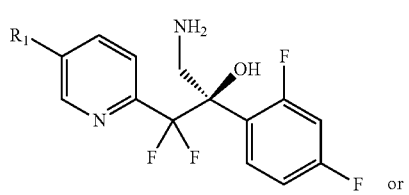

or a mixture thereof;

(vi) performing a reaction to arylate the enantio-enriched amino-alcohol 4b or 4c, -continued

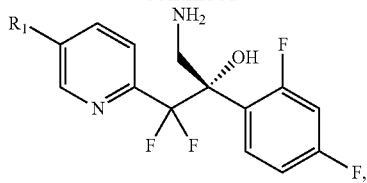

or a mixture thereof, wherein the reaction of (vi) results in a product enantio-enriched amino-alcohol 1-6* or 1-7*,

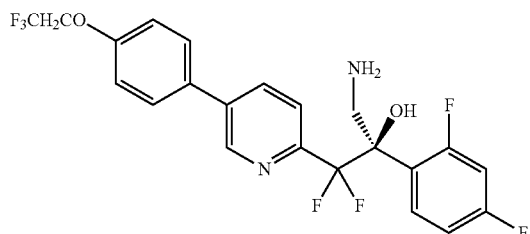

or

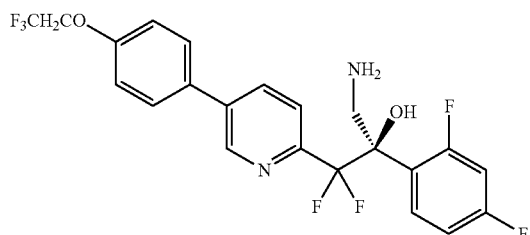

or a mixture thereof;

(vii) performing a reaction to form a salt of enantio-enriched amino-alcohol 1-6* or 1-7*,

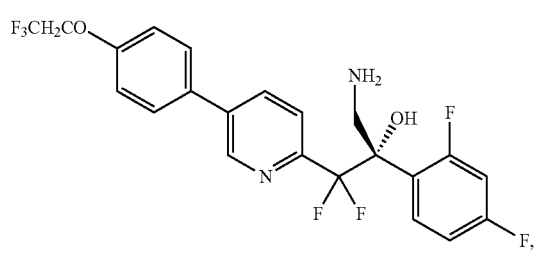

or a mixture thereof, wherein reaction of (vii) results in a product XI or XIa,

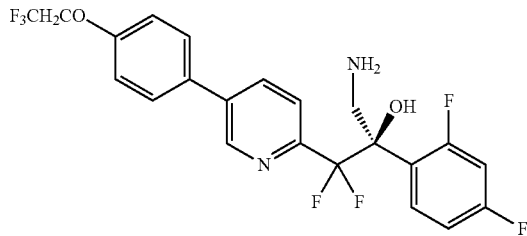

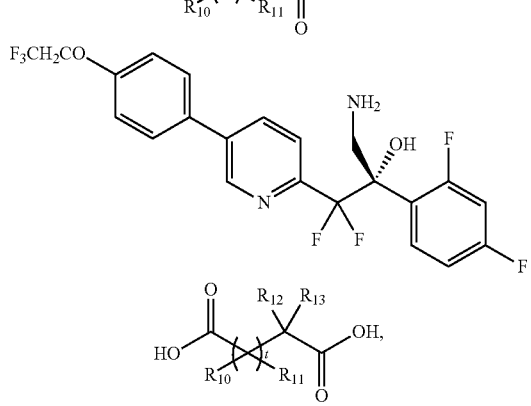

or a mixture thereof; and (viii) performing a reaction to form the tetrazole of XI or XIa,

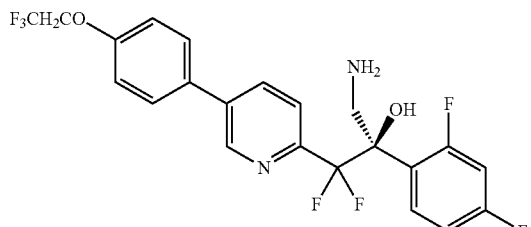

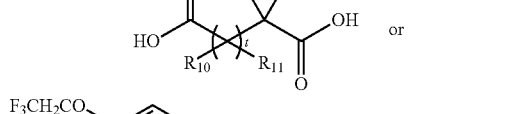

or

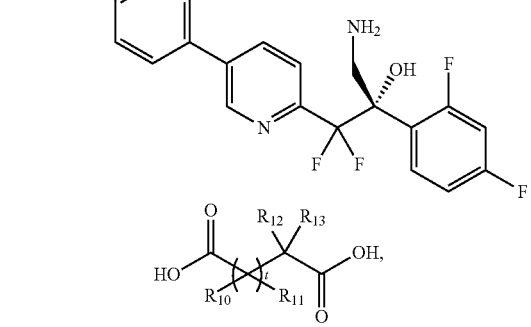

or a mixture thereof, wherein the reaction of (viii) results in a product compound 1 or 1a,

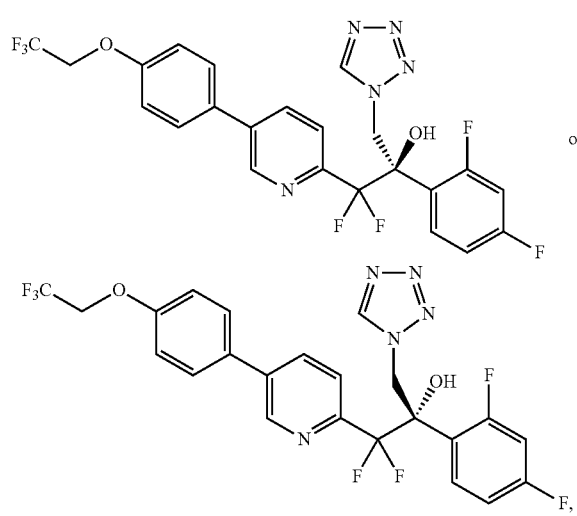

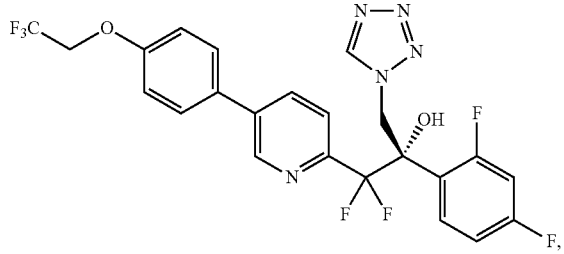

or a mixture thereof;

wherein each R₁ is independently halo, —O(C=O)-alkyl, —O(C=O)-substituted alkyl, —O(C=O)-aryl, —O(C=O)-substituted aryl, —O(C=O)—O-alkyl, —O(C=O)—O-substituted alkyl, —O(C=O)—O-aryl, —O(C=O)—O-substituted aryl, —O(SO₂)-alkyl, —O(SO₂)-substituted alkyl, —O(SO₂)-aryl, or —O(SO₂)-substituted aryl.

13. The process of claim 12, wherein the salt is selected from the group consisting of maleic acid salt, malonic acid salt, succinic acid salt, fumaric acid salt, malic acid salt, tartaric acid salt, dibenzoyltartaric acid salt, di-p-toluoyltartaric acid salt, and mandelic acid salt.

14. The process of claim 12, wherein the salt is tartaric acid salt, di-p-toluoyltartaric acid salt, or malic acid salt.

15. The process of claim 12, wherein the salt is L-tartaric acid salt or D-malic acid salt.

16. The process of claim 12, wherein the salt is L-tartaric acid salt.

* * * * *